(12) United States Patent
Hansen et al.

(10) Patent No.: US 8,435,731 B2
(45) Date of Patent: May 7, 2013

(54) MARKERS FOR VIRAL INFECTIONS AND OTHER INFLAMMATORY RESPONSES

(75) Inventors: Thomas R. Hansen, Fort Collins, CO (US); Natalia P. Smirnova, Fort Collins, CO (US); Kathleen J. Austin, Laramie, WY (US); Alberto van Olphen, Tampa, FL (US)

(73) Assignees: Colorado State University Research Foundation, Fort Collins, CO (US); The University of Wyoming, Laramie, WY (US)

( * ) Notice: Subject to any disclaimer, the term of this patent is extended or adjusted under 35 U.S.C. 154(b) by 292 days.

(21) Appl. No.: 12/337,217

(22) Filed: Dec. 17, 2008

(65) Prior Publication Data

US 2009/0191540 A1 Jul. 30, 2009

Related U.S. Application Data

(63) Continuation-in-part of application No. 11/622,124, filed on Jan. 11, 2007, now abandoned.

(60) Provisional application No. 61/014,172, filed on Dec. 17, 2007, provisional application No. 60/757,965, filed on Jan. 11, 2006.

(51) Int. Cl.
*C12Q 1/70* (2006.01)
*C07H 21/00* (2006.01)
*A61K 39/12* (2006.01)

(52) U.S. Cl.
USPC .................. 435/5; 536/23.72; 424/218.1

(58) Field of Classification Search .......... None
See application file for complete search history.

(56) References Cited

U.S. PATENT DOCUMENTS
2007/0196823 A1  8/2007  Hansen et al.

FOREIGN PATENT DOCUMENTS
WO   2004/028467   4/2004
WO   2007/082259   7/2007

OTHER PUBLICATIONS

Genbank Accession No. NM_174301, accessed from www.ncbi.nlm.nih.gov/nuccore/76253706 on Dec. 20, 2010.*
Werling et al., Veterinary Immunology and Immunopathology, 2005, 108(1-2):157-164.*
Rimland et al., Molecular Pharmacology, 1991, 40(6):869-875.*
GenBank Sequence Revision History for NM_174301, 2 pages, accessed on May 10, 2011, from http://www.ncbi.nlm.nih.gov/sviewer/girevhist.cgi?val=NM_174301.3&log$=seqview.*
GenBank Accession No. NM_174301.2, Sep. 2005, Bos taurus chemokine (C-X-C motif) receptor 4 (CXCR4) mRNA, 2 pages.*
Avalos-Ramirez, R., et al., "Evidence for the presence of two novel pestivirus species," Virology, 286:456-465 (2001).
Vassilev, V.B., et al., "Authentic and chimeric full-length genomic cDNA clones of bovine viral diarrhea virus that yield infectious transcripts," J. Virol., 71(1):471-478, (Jan. 1997).
Behrens, S-E., et al., "Characterization of an autonomous subgenomic pestivirus RNA replicon," J. Virol., 72 (3):2364-2372, (Mar. 1998).
Meyer, C. et al., "Recovery of virulent and RNase-negative attenuated type 2 bovine viral diarrhea viruses from infectious cDNA clones," J. Virol., 76(16):8494-8503, (Aug. 2002).
Jones, L.R. et al., "Quasispecies in the 5' untranslated genomic region of bovine viral diarrhoea virus from a single individual," J. Gen. Virol., 83:2161-2168, (2002).
Aoki, H., et al., "Method for detection of extraneous active bovine viral diarrhoea virus and classical swine fever virus in animal viral vaccines by RT-PCR, which amplify negative-strand viral RNA in infected cells," Biologicals, 30:27-35, (2002).
Sandvik, T., et al., "Detection and identification of ruminant and procine pestiviruses by nested amplification of 5' untranslated cDNA regions," J. Virol. Methods 64:43-56, (1997).
Werling, D., et al. "Ability to differentiate between cp and ncp BVDV by microarrays: Towards an application in clinical veterinary medicine?" Veterinary Immunology and Immunopathy, 108:1-2, 157-164 (Oct. 18, 2005), abstract only provided.

* cited by examiner

*Primary Examiner* — Stacy B. Chen
(74) *Attorney, Agent, or Firm* — Dann, Dorfman, Herrell & Skillman; Kathleen D. Rigaut

(57) ABSTRACT

Compositions and methods for the detection, diagnosis and treatment of BVDV are provided.

16 Claims, 11 Drawing Sheets

Figure 1

*In utero* infection with non-cytopathic BVDV

*Before 150 days of gestation*

*After 150 days of gestation*

In utero infection before 150d of gestation with non-cytophatic BVDV may result in persistent infection of the fetus. The cow becomes immune, and the fetus immunotolerant The nursing calf is persistently infected for life, viremic and releasing virus in all bodily secretion, but seronegative to the infecting genotype.

Persistently infected heifer will always produce a PI calf and if superinfected with an homologous cp virus may develop mucosal disease, a fatal condition.

Infection of a pregnant cow after 150d of gestation results in acute infection of the fetus. The cow and fetus clear the virus and become immune The surviving calf is immunocompetent and clears the virus. The long-term effects of acute fetal infection are unknown Generation of persistent and acute BVDV infections.

Figure 7
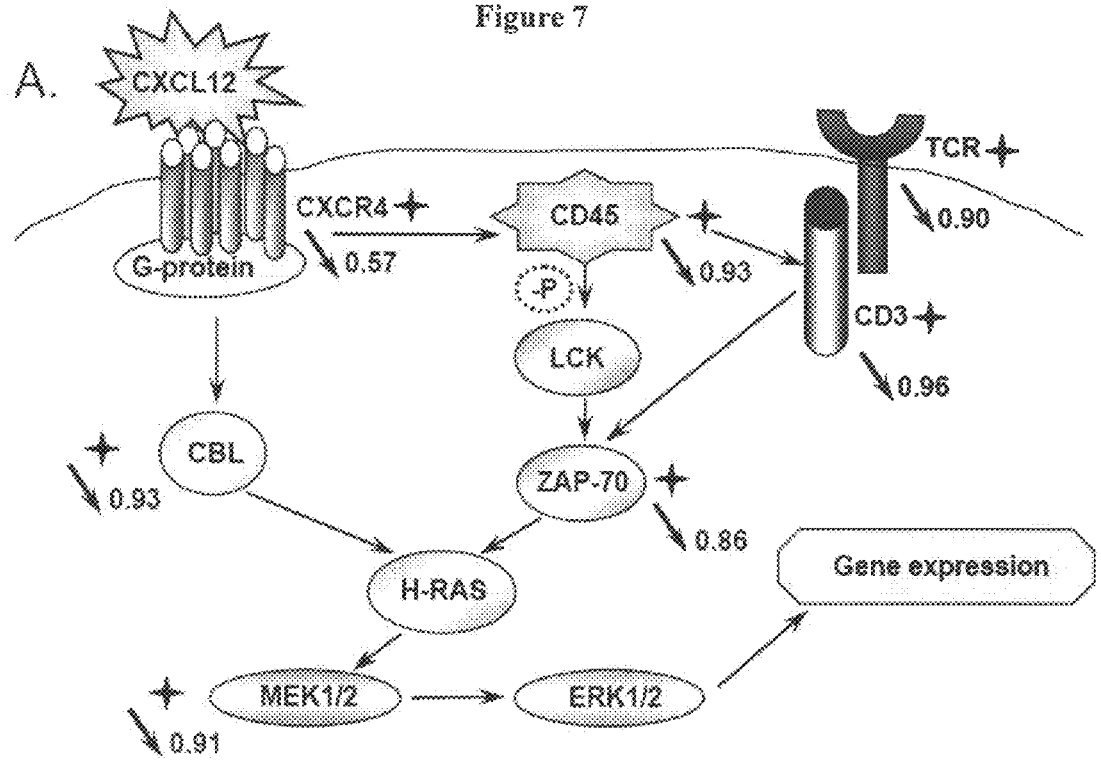
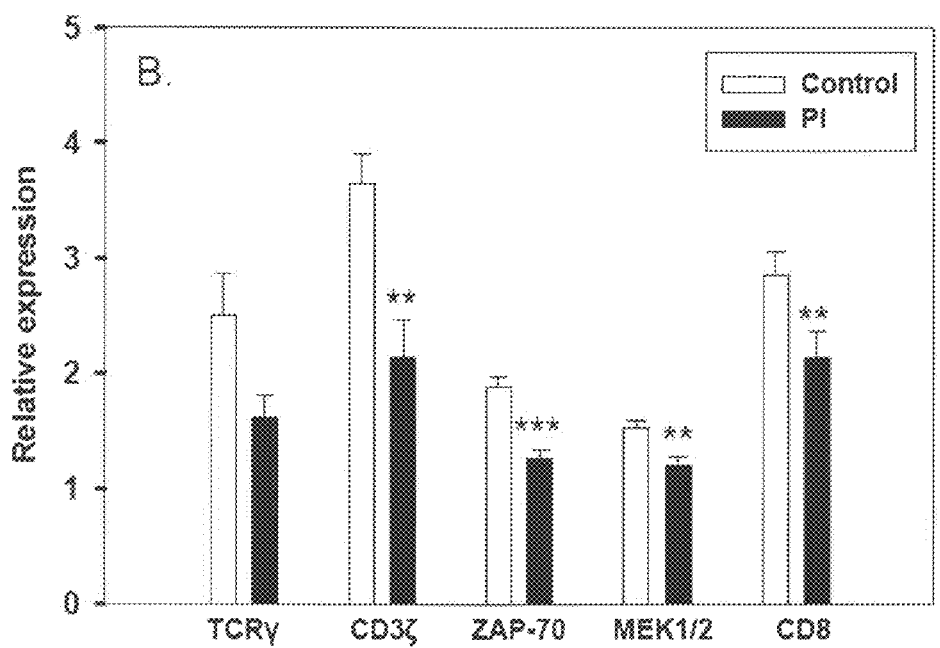

US 8,435,731 B2

```
                          SEQUENCE LISTING

<160> NUMBER OF SEQ ID NOS: 76

<210> SEQ ID NO 1
<211> LENGTH: 19
<212> TYPE: DNA
<213> ORGANISM: Artificial Sequence
<220> FEATURE:
<223> OTHER INFORMATION: primer

<400> SEQUENCE: 1
cgggtcacat acacatcaa                                                  19

<210> SEQ ID NO 2
<211> LENGTH: 20
<212> TYPE: DNA
<213> ORGANISM: Artificial Sequence
<220> FEATURE:
<223> OTHER INFORMATION: primer

<400> SEQUENCE: 2
aggaggcggt tgtcatacac                                                 20

<210> SEQ ID NO 3
<211> LENGTH: 19
<212> TYPE: DNA
<213> ORGANISM: Artificial Sequence
<220> FEATURE:
<223> OTHER INFORMATION: primer

<400> SEQUENCE: 3
acggagatca ggatcaaac                                                  19

<210> SEQ ID NO 4
<211> LENGTH: 20
<212> TYPE: DNA
<213> ORGANISM: Artificial Sequence
<220> FEATURE:
<223> OTHER INFORMATION: primer

<400> SEQUENCE: 4
agtctcatcc ctgggacctt                                                 20

<210> SEQ ID NO 5
<211> LENGTH: 18
<212> TYPE: DNA
<213> ORGANISM: Artificial Sequence
<220> FEATURE:
<223> OTHER INFORMATION: primer

<400> SEQUENCE: 5
aaggctcaga agcgcaag                                                   18

<210> SEQ ID NO 6
<211> LENGTH: 20
```

```
<212> TYPE: DNA
<213> ORGANISM: Artificial Sequence
<220> FEATURE:
<223> OTHER INFORMATION: primer

<400> SEQUENCE: 6
gagtcgatgc tgatcccaat                                               20

<210> SEQ ID NO 7
<211> LENGTH: 20
<212> TYPE: DNA
<213> ORGANISM: Artificial Sequence
<220> FEATURE:
<223> OTHER INFORMATION: primer

<400> SEQUENCE: 7
tgaccccttc attgaccttc                                               20

<210> SEQ ID NO 8
<211> LENGTH: 20
<212> TYPE: DNA
<213> ORGANISM: Artificial Sequence
<220> FEATURE:
<223> OTHER INFORMATION: primer

<400> SEQUENCE: 8
cgttctctgc cttgactgtg                                               20

<210> SEQ ID NO 9
<211> LENGTH: 20
<212> TYPE: DNA
<213> ORGANISM: Artificial Sequence
<220> FEATURE:
<223> OTHER INFORMATION: primer

<400> SEQUENCE: 9
aaagagcttc ctcccgtagc                                               20

<210> SEQ ID NO 10
<211> LENGTH: 20
<212> TYPE: DNA
<213> ORGANISM: Artificial Sequence
<220> FEATURE:
<223> OTHER INFORMATION: primer

<400> SEQUENCE: 10
ggatggcctt gtcttcacac                                               20

<210> SEQ ID NO 11
<211> LENGTH: 20
<212> TYPE: DNA
<213> ORGANISM: Artificial Sequence
<220> FEATURE:
<223> OTHER INFORMATION: primer

<400> SEQUENCE: 11
tgggactaac agcttcacca                                               20

<210> SEQ ID NO 12
<211> LENGTH: 20
<212> TYPE: DNA
<213> ORGANISM: Artificial Sequence
<220> FEATURE:
<223> OTHER INFORMATION: primer

<400> SEQUENCE: 12
actgcatcaa gattggcaca                                               20
```

```
<210> SEQ ID NO 13
<211> LENGTH: 20
<212> TYPE: DNA
<213> ORGANISM: Artificial Sequence
<220> FEATURE:
<223> OTHER INFORMATION: primer

<400> SEQUENCE: 13
aagggtggct cctcaggcaa                                              20

<210> SEQ ID NO 14
<211> LENGTH: 20
<212> TYPE: DNA
<213> ORGANISM: Artificial Sequence
<220> FEATURE:
<223> OTHER INFORMATION: primer

<400> SEQUENCE: 14
gtcaactgac ccagggcatc                                              20

<210> SEQ ID NO 15
<211> LENGTH: 20
<212> TYPE: DNA
<213> ORGANISM: Artificial Sequence
<220> FEATURE:
<223> OTHER INFORMATION: primer

<400> SEQUENCE: 15
acgtggcaga acaaatcaga                                              20

<210> SEQ ID NO 16
<211> LENGTH: 20
<212> TYPE: DNA
<213> ORGANISM: Artificial Sequence
<220> FEATURE:
<223> OTHER INFORMATION: primer

<400> SEQUENCE: 16
tctggttgaa ccctgactga                                              20

<210> SEQ ID NO 17
<211> LENGTH: 19
<212> TYPE: DNA
<213> ORGANISM: Artificial Sequence
<220> FEATURE:
<223> OTHER INFORMATION: primer

<400> SEQUENCE: 17
ctgcaaagat tgacagcag                                               19

<210> SEQ ID NO 18
<211> LENGTH: 20
<212> TYPE: DNA
<213> ORGANISM: Artificial Sequence
<220> FEATURE:
<223> OTHER INFORMATION: primer

<400> SEQUENCE: 18
agtggctgca caaaatgaca                                              20

<210> SEQ ID NO 19
<211> LENGTH: 20
<212> TYPE: DNA
<213> ORGANISM: Artificial Sequence
<220> FEATURE:
<223> OTHER INFORMATION: primer
```

```
<400> SEQUENCE: 19
gaggagcaga acaggaccaa                                              20

<210> SEQ ID NO 20
<211> LENGTH: 20
<212> TYPE: DNA
<213> ORGANISM: Artificial Sequence
<220> FEATURE:
<223> OTHER INFORMATION: primer

<400> SEQUENCE: 20
gacaggaccc cttgctgata                                              20

<210> SEQ ID NO 21
<211> LENGTH: 20
<212> TYPE: DNA
<213> ORGANISM: Artificial Sequence
<220> FEATURE:
<223> OTHER INFORMATION: primer

<400> SEQUENCE: 21
tagacggtgc cctaaaatgg                                              20

<210> SEQ ID NO 22
<211> LENGTH: 20
<212> TYPE: DNA
<213> ORGANISM: Artificial Sequence
<220> FEATURE:
<223> OTHER INFORMATION: primer

<400> SEQUENCE: 22
aactgtttgc ccagtggttt                                              20

<210> SEQ ID NO 23
<211> LENGTH: 20
<212> TYPE: DNA
<213> ORGANISM: Artificial Sequence
<220> FEATURE:
<223> OTHER INFORMATION: primer

<400> SEQUENCE: 23
acatagcggt gtcattgcag                                              20

<210> SEQ ID NO 24
<211> LENGTH: 20
<212> TYPE: DNA
<213> ORGANISM: Artificial Sequence
<220> FEATURE:
<223> OTHER INFORMATION: primer

<400> SEQUENCE: 24
ctcattccat gaggtgagca                                              20

<210> SEQ ID NO 25
<211> LENGTH: 22
<212> TYPE: DNA
<213> ORGANISM: Artificial Sequence
<220> FEATURE:
<223> OTHER INFORMATION: primer

<400> SEQUENCE: 25
gcatgctttg ctgctataaa aa                                           22

<210> SEQ ID NO 26
<211> LENGTH: 21
```

<212> TYPE: DNA
<213> ORGANISM: Artificial Sequence
<220> FEATURE:
<223> OTHER INFORMATION: primer

<400> SEQUENCE: 26
aagggctctg gctagatttt g    21

<210> SEQ ID NO 27
<211> LENGTH: 20
<212> TYPE: DNA
<213> ORGANISM: Artificial Sequence
<220> FEATURE:
<223> OTHER INFORMATION: primer

<400> SEQUENCE: 27
tgagcaacct gacctctgaa    20

<210> SEQ ID NO 28
<211> LENGTH: 20
<212> TYPE: DNA
<213> ORGANISM: Artificial Sequence
<220> FEATURE:
<223> OTHER INFORMATION: primer

<400> SEQUENCE: 28
ggtggcctct cctctttcat    20

<210> SEQ ID NO 29
<211> LENGTH: 1077
<212> TYPE: DNA
<213> ORGANISM: Bos Taurus

<400> SEQUENCE: 29
atggggccgc gaaccctcct cctgctgctc tcggggtcc tggtcctgac cgagaccctg    60
gcgggctccc actccctgag gtatttcagc accgccgtgt cccggcccgg cctcggggag    120
ccccgcttca tcgccgtcgg ctacgtggac gacacgcagt tcacacggtt cgacagcgac    180
gccccgaatc aagggaaga accgcgggtg ccgtggatgg agcaggaggg gctggagtat    240
tgggatcgaa acacgagaat ctacaaggac accgcacaga ctttccgagt gtacctgaac    300
gccctgcgcg gctactacaa ccagagcgag gccgggtctc acaccctcca gtggatgtcc    360
ggctgcgacg tggggccgga tgggcgcctc ctccgcgggt tttggcagtt cggctacgac    420
ggcagaaatt acatcgccct gaacgaggac ctgcgctcct ggaccgcggc ggacacggcg    480
gctcagatca ccaagcgcaa gtgggaggcg gcaggtgctg cggagggcga gaggaactac    540
gtggagggcc ggtgcgtgga ggggctccgc agatacctgg aaaacgggaa ggacgcgctg    600
ctgcgcgcag accctccaaa ggcacatgtg acccatcacc ccatctctga gcgtgaggtc    660
accctgaggt gctgggccct gggcttctac cctgaggaga tctcactgac ctggcagcgc    720
gaggggagg accagaccca ggacatggag cttgtggaga ccaggccttc agggggatgga    780
accttccaga gtgggcggc cctggtggtg ccttctggag aggagcagag atacacgtgc    840
cgtgtgcagc atgaggggct tcaggagccc ctcacccctg atgggaacc tcctcagacc    900
tccttcctca ccatgggcat cattgttggc ctggttctcc tcgtagtagc tgtggtggct    960
ggagctgtga tctggaggaa gaagcgctca ggtgaaaaag gacggatcta cacccaggct    1020
gcaagcagtg acagtaccca gggctctgat atgtctctca cagttcctaa agtttga    1077

<210> SEQ ID NO 30
<211> LENGTH: 1177

```
<212> TYPE: DNA
<213> ORGANISM: Bos Taurus

<400> SEQUENCE: 30
gagttcagcc ctcaccattg ctctgcaact cagaacagtt actactgaga ctaccctgag    60
aagaggatgg tcctaaacag agctctgatt ctggggccc tcaccctgac caccatgaca   120
agcctctgtg gaggtgaaga cattgtggct gaccacattg gcacctacgg tgcagacttc   180
taccaatctc atggtccctc tggccagtac atccatgaat tgatggaga tgagttgttt    240
tatgtggacc tggggaagaa ggagactgtc tggcagctgc ctatgtttgg tgaattaaca   300
agttttgaag cacaagatgc gctgaatgaa atagctaaag caaaacacac cttggatgtc   360
ctgactaaac gctccaactt taccctgtt atcaatgagg ttcctgaggt gactgtgttt    420
tccaagtctc ccatgatgct gggtcagccc aacaccctca tctgccacgt ggacaacatt   480
tttccccctg tgatcaacat cacatggttg aggaatgggc atgcagtcac agagggtgtt   540
tctgagacca gcttcctccc caaaagtgat tattccttcc tcaagattgg ttatcttacc   600
ttcctccctt ctgatgatga tgtttacgac tgcaaagtgg agcactgggg cctggatgag   660
ccacttctga aacactggga gcctgagatt ccagccccta tgtcagagct gacagagact   720
gtggtctgtg ccctggggtt gactgtgggc ctcgtgggca tcgtggtggg cactgtcctc   780
atcatccgag gtctgcgctc aggtggagcc tccagacacc aagggccctt gtgagtcaca   840
ctccagtagg aaggtgcact gtccatctac aagaacagaa aaatggacat attagatgac   900
ctggaactat tttctggcca agttcatcat gtacctttc tccttctgcc ctcctctgct    960
cacctcttct ctgggaaatc ggatgctgta tcacctcaga gttcacatgt acctcagagt  1020
tcttgccctg actatgtgat atttctttct cttctcatta gttgcatacc atggaattgc  1080
tacggtattc cacccaatta cctaatctct agtgaccctg attccatgtc accacagaag  1140
caataaatcc ttcttttatc gaaaaaaaaa aaaaaaa                           1177

<210> SEQ ID NO 31
<211> LENGTH: 1125
<212> TYPE: DNA
<213> ORGANISM: Bos Taurus

<400> SEQUENCE: 31
atggctcacc tggactcaga gagtgaaacc agccccagca tcttcccgct gagccttggg    60
aacaacgacc cagccgggca ggtggtcatc ggctgcctgg tccagggctt cttcccgtcg   120
gcacccctga gcgtgacctg aaccagaat ggcgacagcg tgtccgtcag gaacttccct    180
gccgtgctgg ccgggagcct gtacaccatg agcagccagc tgaccttgcc ggccagcctg   240
tgcccaaaag gccagtccgt gacctgccaa gtgcagcacc tctccaaagc cagcaagacc   300
gtggccgtgc cctgcataat tcaagactca agttcatgtt gcgtgccgaa ctgcgagccc   360
agcctgtccg tgcagccacc agccctcgag gacctgctcc tgggctccaa cgccagcctc   420
acgtgcacac tgagtggcct gaaaagcgcc gagggcgcca gcttcacctg gaacccgaca   480
ggtgggaaga ccgccgtcca ggggtcgccc aagcgtgact cctgtggctg ctacagcgtg   540
tccagcgtcc tgccgggctg tgccgatccc tggaacagtg gacagacttt ctcctgctct   600
gtcacccacc ccgagtccaa gagttcactg accgccacca tcaagaaaga cttagggaac   660
acgttccggc ctcaggtcca cctgctgccg ccgcgtcgg aggagctggc cctcaacgag   720
ctggtgacgc tgacgtgcct ggtgcgggga ttcagcccca aggaggtgct ggtgcgttgg   780
ctgcagggca atcaagagct gccccgcgag aagtatctga cctggggccc cctgcccgag   840
```

```
gctggccaga gcgtcaccac cttcgccgtg accagcgtgc tacgcgtgga cgccgaggtc    900
tggaagcagg gggacacctt ctcctgcatg gtgggccacg aggccctgcc cctggccttc    960
acccagaaga ccatcgaccg cctggcggaa catcagccct ggctggtgct ggacctgatg   1020
cagagcagcc ccgaggagga cagcccagag gccagcctgt ggcccacgac cgtcaccctg   1080
ctcaccctct cctgctgag cctcttctac agcacagcac tgact                    1125
```

<210> SEQ ID NO 32
<211> LENGTH: 1513
<212> TYPE: DNA
<213> ORGANISM: Bos Taurus

<400> SEQUENCE: 32

```
cactgagacc cgtcacccgg actctacgtg agacccacca cccggactca ccatgcgtga     60
atgcatctca gtccatgtgg ggcaggcagg tgtccagatg ggcaatgcct gctgggagct    120
ctactgtctg gaacatggaa ttcagccgga tggacagatg cccagtgaca agaccatcgg    180
tggaggggac gactccttca ccaccttctt ctgtgaaacc ggtgccggaa agcatgtgcc    240
ccgggcagtt tttgtggatt tggagcctac cgtaattgat gagatccgaa acggcccata    300
ccggcaactc ttccaccccg agcagctcat cactgggaaa gaggatgcgg cgaacaacta    360
tgctcgtggt cactacacca ttggcaagga aatcattgac ccagtcctgg accggatccg    420
caagctgtct gatcagtgca caggacttca gggcttcctg gtgttccaca gctttggagg    480
gggcactggc tctggcttca cctcactgct gatggagcgg ctctctgttg actatggcaa    540
gaaatccaag ctggagttct ccatctaccc agccccccag gtgtccacgg ccgtggttga    600
gccctacaac tccatcctga ccactcacac cactctggag cactcagatt gcgccttcat    660
ggtggacaac gaggccatct atgacatctg tcgccgcaac ctggacatcg agcgtccaac    720
ttacaccaac ctcaaccgcc tcatcagcca gatcgtctcc tccatcacag cctccctgcg    780 cttttgacggc gccctcaacg tggacctgac cgagttccag accaacctgg tgccctaccc    840
tcgcatccac tttccccctgg ccacctatgc caccagtcatc tctgcagaga aggcctacca    900
cgagcagctg tcggtggcag agatcaccaa cgcctgcttc gagcctgcca ccagatggt    960 gaagtgtgat ccccgccacg gcaagtacat ggcctgctgc ctgctgtacc gtggagatgt   1020
ggtgcccaag gacgtcaacg ctgccattgc tgccatcaag accaagcgca gtattcagtt   1080
cgtggactgg tgccccacgg gcttcaaggt cggtatcaac taccagcccc ccactgtggt   1140 gccccggggga gacctggcca aggtgcagcg tgccgtgtgc atgctgagca acacgaccgc   1200
catcgctgag gcctgggccc gcctggacca caagttcgac ctgatgtatg ccaagagggc   1260
gtttgtgcac tggtacgtgg gcgagggcat ggaggagggt gagttctccg aggcccggga   1320
ggatatggct gccctggaga aggattacga ggaagtgggc atcgactcct atgaggatga   1380
ggatgaggga gaagaataga atctctgcct ggagcccact cactatgttt attgcaaaat   1440
cctttcgaaa taaacagtct ccttgcacgg ttaaaaaaaa aaaaaaaaa aaaaaaaaaaa   1500 aaaaaaaaaa aaa                                                      1513
```

<210> SEQ ID NO 33
<211> LENGTH: 906
<212> TYPE: DNA
<213> ORGANISM: Bos Taurus

<400> SEQUENCE: 33

```
gaaaagcaca gtcaaccccc agctttcccc aggagccctc cttgcaaggc catgaagatg     60
```

-continued

| | |
|---|---|
| agccggctct gcctctccat agcccttctg gtcctcctgg gcaccctggc ggccagcact | 120 |
| ccagggtgtg acaccagcaa ccaggccaaa gcccagcggc ctgacttctg cctagagcct | 180 |
| ccatatacgg gtccctgcaa ggccaaaatg atcagatact tctacaacgc caaggctggg | 240 |
| ttctgcgaga cctttgtata tggtggctgc aaagctaaga gcaacaattt caggagcgca | 300 |
| gaggactgca tgaggacctg tggtggtgct attgggcccc gggagaacct gtgaactgtg | 360 |
| ctcccctgag atgctgaagt atgaggagga cccacccaag gctggcctct atctgcttct | 420 |
| gaaaaatttc agcctccttt tatttcttct caaccctccc ctcctcagca gaaatctgtc | 480 |
| tctttccttc ctccacaggt ccacttactt tagccctatc tcatccagtt tgctctaagc | 540 |
| accatgaaag caaatcttcc ctttgtccct cacacttccc acaatttctg gcacaaagga | 600 |
| gaaggtccag aaatattgga ggaaggaagg aatgaagttc cccatgactg gagcatctgt | 660 |
| agagtctgag atttaaatct ggattcttgt cctaatcttc ctcctcacgg catccttacc | 720 |
| ttcatcctcc accccaccat cactgctctc cctctactgg cgaaagtaga atttccatca | 780 |
| tcgagttttc agctcagtgg tgggagaggt cttttcatga cgaagcctcc tcctcacatt | 840 |
| gatttgaagg tctgtggctt caaagagtct ggccttatct ttaaataaat tcatatttta | 900 |
| attaaa | 906 |

<210> SEQ ID NO 34
<211> LENGTH: 1414
<212> TYPE: DNA
<213> ORGANISM: Bos Taurus

<400> SEQUENCE: 34

| | |
|---|---|
| ccgggtgaga ctagagagca gagggagatg tgaggaggaa ggcgaatgtc cctaccaggt | 60 |
| gaacctgccc ccgctgacta ttcagctccc caagcagttc agcaggatcg aggaggtgtt | 120 |
| caaagaagtt cagaatctca aggaaattgt aaatagcctg aagaagactt gccaagactg | 180 |
| caaactgcag gctgatgaca gtcgagaccc aggaagaaat ggattgctgt taccaggcac | 240 |
| aggagcccca ggagaaactg gggacaacag agtgagagaa ttagagggcg aggttaacaa | 300 |
| actgtcctct gaccttaaga atgccaagga ggagatcgat gtgcttcagg tcgcctgga | 360 |
| gaagctgaat cttgtaaata tgaacaacat agaacagtat gttgatagca aagtggcaaa | 420 |
| cctcacattt gttgtcaata gtttggatgg caaatgttca tctaagtgtc ccaggcaaga | 480 |
| acaaatacaa tcactcccag ttcaacaaca tcttatatat aaagattgct ctgaatacta | 540 |
| cacaataggc aaaagaagca gtgagctcta tagagttaca ccggagccca gaaacagtag | 600 |
| cttcgaagtt ttctgtgaca tggagaccat ggcaggaggc tggacggtgc tgcaagcacg | 660 |
| tgttgatgga agcaccaact tcaccagaac atggcaagac tacaaagtag gctttggaaa | 720 |
| cctcagaaga gaattttggc tggggaatga taaaatccac cttctgacta agagtaagga | 780 |
| catgattcta agaatagacc ttgaagactt taatggtatc aaactctatg ccttgtatga | 840 |
| tcacttttat gtggccaacg agtttctcaa ataccgtcta cacattggta actataatgg | 900 |
| cacagctgga gatgccttac gtttcagtaa acattacaac catgacctga gttttttcac | 960 |
| caccccggat agagacaatg atcgataccc ctctgggaac tgtgggctct actacagttc | 1020 |
| aggctggtgg tttgatgcct gtcttttctgc aaacttaaat ggcaaatatt atcaccaaaa | 1080 |
| atacagaggt gtccgaaatg ggattttctg gggtacctgg cctggcataa gtgaggcaca | 1140 |
| acctggtggt tacaagtcct ccttcaaaga agtcaaaatg atgatcagac ccaagcactt | 1200 |
| taagccgtaa atcactaatg ctaacaattc tgggtattca ttacccaata gggcaattaa | 1260 |

```
ttccttcagc actttggaat atgtttcaaa ctccttttcc acggcttaaa atttatctct   1320
gagcaatggg ttcttatgcc acatagcatt tgaaataaag ctgaaaaata tgccttttaa   1380
aaaaaaaaaa aaaaaaaaaa aaaaaaaaaa aaaa                                1414
```

<210> SEQ ID NO 35
<211> LENGTH: 817
<212> TYPE: DNA
<213> ORGANISM: Bos Taurus

<400> SEQUENCE: 35

```
gactctctga attatactcc ccaggagacg ggggcccatg aacaggtgg cagttagggc     60 tgattctttg atactttagg tggtatccta tgtccttctc ccctattcta tccacaaata   120
agaacattca ccgtgggtca aacagagcag cagacccggg atagtagccc ttgtctaaac   180
cattaatgag gaaggaggag acagtggaag cgtggggctg gggaggcgct gctctagacc   240
tcccttgtct cctgaaggtg aacgtagttt ggtaaaatga ctaagctgga agatcacctg   300
gagggaatca tcaacatctt ccaccagtac tccgttcggg tggggcattt cgacaccctc   360
aacaagcgtg agctgaagca gctgatcaca aaggaacttc ccaaaaccct ccagaacacc   420
aaagatcaac ctaccattga caaaatattc caagacctgg atgccgataa agacggagcc   480
gtcagctttg aggaattcgt agtcctggtg tccagggtgc tgaaaacagc ccacatagat   540
atccacaaag agtaggaagc tctttccagc aatgtcccca agaagactta cccttctcct   600
ccctgaggct gccttacccg agggaagaga gaattaataa acgtactttg gcaaagttct   660
tagcagaaaa aaaaaaaaaa aaaaaaaaaa aaaaaaaaaa aaaaaaaaaa aaaaaaaaaa   720
aaaaaaaaaa aaaaaaaaaa aaaaaaaaaa aaaaaaaaaa aaaaaaaaaa aaaaaaaaaa   780
aaaaaaaaaa aaaaaaaaaa taaaaaaaaa aaaaaaa                             817
```

<210> SEQ ID NO 36
<211> LENGTH: 470
<212> TYPE: DNA
<213> ORGANISM: Bos Taurus
<220> FEATURE:
<221> NAME/KEY: misc_feature
<222> LOCATION: 5, 261
<223> OTHER INFORMATION: n = a, c, t, or g

<400> SEQUENCE: 36

```
acttnccagg agtggtgact ctcatcttct ccaagatgaa cccactgtgg accctcctct    60
ttgtgctgtc agcccccaga ggggtcctgt cccaaagtca gctgcgggag tcgggcccca   120
gcctggtgag gccctcacag accctctccc tcacctgcac ggtctctgga ttttcactga   180
acagccatgc gttagaatgg gtccgccagg ctccaggaa ggcgctggag tggcttgcta    240
tgattaataa tggtggatac ncatactata attcagccct gaaatcccgg ctcagcatca   300
ccaaggacac cgccaagagc caagtctctc tgtcactgag cagagtgact cctgaggaca   360
cggccacata ctactgtcta gtgtgttttg gtgattgggg tggtggttgg agttgttctt   420
ggaatgatgt tcctgcctgg ggccaaggag tcctggtcac agtctcctca                470
```

<210> SEQ ID NO 37
<211> LENGTH: 635
<212> TYPE: DNA
<213> ORGANISM: Bos Taurus

<400> SEQUENCE: 37

```
gacgagtctg cggagctcca gccctgcagc ccctgcgctg gctctcggct ccggctggca    60
```

-continued

```
ctcctgagcg cgatgaacca ggcagtcgta ccccgcgcct cccgcccgcg gtccagcccg      120
gggctgctgc tcctggggct gctgcttctg ccggccatcg ccctggccca agagtcgtca      180
ttccctgcca ccttcgtccc gctcccagcg gactctgaag gtggagagtc tgaggacctc      240
caatgcgtgt gcctgaagac cacttcgggg attaacccca ggcacatctc cagcctggaa      300
gtgatcgggg ccgggctcca ctgccccagc ccccaactga tagctacgct gaagacggga      360
aggaaaattt gcctggacca gcagaatcct ctgtataaga aaataatcaa gaggcttttg      420
aagagttagt tgcctaaatc tctacttttg ctatagaaaa tgtttcttct tcttcttttt      480
aaaattttca atctacttgt ggaaaacaaa tcatctaatg tttttattgt ccttgaaact      540
ctacataaat aaaagaaatg aagtttaaaa aaaaaaaaa aaaaaaaaaa aaaaaaaaa       600 aaaaaaaaaa aaaaaaaaaa aaaaaaaaaa aaaaa                               635
```

<210> SEQ ID NO 38
<211> LENGTH: 935
<212> TYPE: DNA
<213> ORGANISM: Bos Taurus

<400> SEQUENCE: 38

```
ggatgctctg ctcagctgtg gggccacaga cagcaggaca ccctgaccat gtccaccatg      60
gcctggtccc ctctgctcct caccctggtc gctctgtgca caggatcctg ggcccaggct     120
gtgctgactc agccgtcctc cgtgtccggc tccctgggcc agagggtctc catcacctgc     180
tctggaagca gcagcaacat cggtagagat aatgtgggct ggtaccaaca ggtcccagga     240
tcgggcctca gaaccatcat ctatagtagt agcagtcgac cctcgggggt ccccgaccga     300
ttctccggct ccaagtctgg caacacagcc accctgacca tcagctccct ccaggctgag     360
gacgaggcgg attatttctg tgtagcttat gacagtagta gtagtactgt tttcggcagc     420
gggaccacac tgaccgtcct gggtcagccc aagtccccac cctcggtcac cctgttcccg     480
ccctccacgg aggagctcaa cggcaacaag gccaccctgg tgtgtctcat cagcgacttc     540
tacccgggta gcgtgaccgt ggtctggaag gcagacggca gcaccatcac ccgcaacgtg     600
gagaccaccc gggcctccaa acagagcaac agcaagtacg cggccagcag ctacctgagc     660
ctgacgagca gcgactggaa atcgaaaggc agttacagct gcgaggtcac gcacgagggg     720
agcaccgtga cgaagacagt gaagccctca gagtgttctt agggccctgg accccaccc      780 tcggggccc tctggcccac accccctccc ccacctctcc atggaccct gagccctac       840 ccaggtcgcc tcacaccagg ggcctctcct cctcccctgt tcctgcttct cctgaataaa      900
gaccttctca tttatcagca aaaaaaaaaa aaaaa                               935
```

<210> SEQ ID NO 39
<211> LENGTH: 652
<212> TYPE: DNA
<213> ORGANISM: Bos Taurus

<400> SEQUENCE: 39

```
gaaacccttc tgcgaggctt ctcggcttgg taggagggtc caaggaagct tgacagtctt      60
ctaagcaccc aactccgttg ctcaaacaga aggcgggaaa atggaggaca aaatgtcaca     120
aatggaaagc agcatagaaa ccatcatcaa catcttccac cagtactctg tacggctagg     180
gcactatgac accctgatcc agaaagaatt caaacagctg gtgcaaaaag agctgccaaa     240 cttttctcaag aagcagaaga gaatgaagc tgctatcaat gagatcatgg aggatctgga     300
cacaaatgta gacaagcagc tgagcttcga ggagttcatt atgctggtgg ccaggctgac     360
```

```
ggtagcctcc cacgaggaga tgcacaacac cgcaccccca ggacaaggcc acaggcacgg    420
gccaggctac gggaagggca gccctgacca gggcagccac gacctgggca gccacggcca    480
cggccacggc cacagccatg gaggtcacgg ccacagccac ggcggtcatg gccacagcca    540
ctaatcagga ggccagccac tgcccaccta gggcctcagg gctgccttcg ctgtgggca    600 gggtgatggg ggtgaaataa agtcttcctc cgagtcaaaa aaaaaaaaa aa           652
```

<210> SEQ ID NO 40
<211> LENGTH: 1077
<212> TYPE: DNA
<213> ORGANISM: Bos Taurus

<400> SEQUENCE: 40

```
atggggccgc gaaccctcct cctgctgctc tcggggtgtcc tggtcctgac cgagaccctg    60
gcgggctccc actccctgag gtatttcagc accgccgtgt cccggcccgg cctcggggag   120
ccccgcttca tcgccgtcgg ctacgtggac gacacgcagt tcacggtt cgacagcgac    180 gccccgaatc caagggaaga accgcgggtg ccgtggatgg agcaggaggg gctggagtat   240
tgggatcgaa acacgagaat ctacaaggac accgcacaga cttccgagt gtacctgaac   300 gccctgcgcg gctactacaa ccagagcgag gccgggtctc acaccctcca gtggatgtcc   360
ggctgcgacg tggggccgga tgggcgcctc ctccgcgggt tttggcagtt cggctacgac   420
ggcagaaatt acatcgccct gaacgaggac ctgcgctcct ggaccgcggc ggacacggcg   480
gctcagatca ccaagcgcaa gtgggaggcg gcaggtgctg cggagggcga ggaactac    540 gtggagggcc ggtgcgtgga ggggctccgc agatacctgg aaaacgggaa ggacgcgctg   600
ctgcgcgcag accctccaaa ggcacatgtg acccatcacc ccatctctga gcgtgaggtc   660
accctgaggt gctgggccct gggcttctac cctgaggaga tctcactgac ctggcagcgc   720 gaggggggagg accagaccca ggacatggag cttgtggaga ccaggccttc agggatgga   780 accttccaga gtgggcggc cctggtggtg ccttctggag aggagcagag atacacgtgc   840
cgtgtgcagc atgaggggct tcaggagccc ctcaccctga gtgggaacc tcctcagacc   900 tccttcctca ccatgggcat cattgttggc ctggttctcc tcgtagtagc tgtggtggct   960
ggagctgtga tctggaggaa gaagcgctca ggtgaaaaag gacggatcta cacccaggct   1020
gcaagcagtg acagtaccca gggctctgat atgtctctca cagttcctaa agtttga      1077
```

<210> SEQ ID NO 41
<211> LENGTH: 670
<212> TYPE: DNA
<213> ORGANISM: Bos Taurus

<400> SEQUENCE: 41

```
gctagcagcc cacaggcaga atctttacca tgccctcttc ctggcttctc ctcctgggca    60
tcactgcctg gcacttgcct tcctccttct acctttcctg tgctcccct caggactttt   120 cattctgcac ggtgattgcc ccattctcct tgttgggaaa cttgaggctg tagcaacact   180
ggaagggagt agctgcctct gagtggcccg aggccctggg cagctggcca atcctggctg   240
ctataaaagg gagccgacac tgagccctgc atgtcttttg caactctgt tttggggaga   300 cctggtgggg caaatccttg acaccatgc tgacggatct ggagtgtgcc attaactccc   360
tgattgacgt ctaccacaag tactccctga aaaagggaa ttaccacgcc gtctatagg   420 atgacttgaa gcaactgtta gagacagagt gtcctaaatt tatgaagaaa aaggatgcgg   480
acacttggtt caaagagttg gacatcaatc aggatggtgg aattaacttc gaggagttcc   540
```

```
tcgtgctggt gataaaggtg ggcctggaag cccatgaaga aattcacaaa gaatagcaga    600
gctattgggc ctggggctag gcccctggac ttgtgcctgc agagtaataa aatagttgat    660
acctcaggtc                                                           670

<210> SEQ ID NO 42
<211> LENGTH: 1485
<212> TYPE: DNA
<213> ORGANISM: Bos Taurus

<400> SEQUENCE: 42
atgatctgtg ttcacaggag acccacaggc ggagtcaagt ctgagaagcg ctgttacttg     60
gtatttggcc ccagcgacca gaaacacgaa tgcctgatca caccccctcag ccaggatatt   120 aaaagctcca tccatcctca gcatcctcag gagccctcct gcgagtccac gaagatgaac   180
cgactctgcc tctctgcagc ccttctcttc ctcctggtta tcctagtgga tggcatctca   240
gaggatatta caagagcca tgaccacggt tatgagatga cttacggaag actaaatgag   300
aagcattcag cagcttctaa gcctgccttc tgcctgaagc ctaaatcaat aggtccctgc   360
aagggcagga agatcaggta cttctacaat gccaagacca ggcaatgcca acgcttttc    420 tacggtggct gcaaagggaa cttgaataac ttctacacca tggcgctgtg catgaacacc   480
tgcggtcatg tggaatggtc ctggagaaga cacgggaaga gtcatgctcc aaaactctga   540
agtccgagga ggacccatga agtctgggc tgctcctgaa acagttcagt ctccttgcat    600
ttcttctctc ccctaccttc ctcagcagag cctgcctatt tcctttcctc tatgatgctg   660
agagacttcc ctggtggcac agatggtaaa agcgtctgac tacaatgtgg gagacccggg   720
ttcaatccct gggtcaggaa gatctcctgg agaaggaaat agcaacccac tccagtgttc   780
ttgcctggaa atcccatgg acagaggagc ctggtaggct acagtccatg ggtcgcaaa    840 gagtaggaca ctactgagca acttcacttc acttatgat gctggggaag attgagagca    900
ggaggagaag gggacagcag aagatgagat ggttgggtgg catcaccaac ttaatgggca   960
tgagtttgag caagctctga acacagtaa agacagggaa gtctggcatg ctgaagccca    1020
ttgggtcaca agagttgga cacgacttgg tgactgaaca acatgcgtct atacaccta    1080 gttcagtctt atccagttgg ctctaagcac catgacagca tgtcttccct ttatcttgag   1140
cacttagcac agttcctggc atgaaggaag cagttcataa ttatgtgagg aaggaaagag    1200
tgcaggagga gcacattcct ctcgaccaga gtaactatag agcctgaggt ttgacaccag   1260
gattgttgcc tcaacccaca tactcatggc atcctcacca tgccatcact gatctccttg   1320
tgtgaggcct tggtggaatt tctggcatcc atttctcagc atcagtaatg agagaagtct   1380
ttgcaataaa aaagctcccc ctttcccta aagatgttgc agttttcctt tctgtatttt    1440
caaacactgt ggcttatatt tcaataaatg catattcaaa actaa                   1485

<210> SEQ ID NO 43
<211> LENGTH: 759
<212> TYPE: DNA
<213> ORGANISM: Bos Taurus

<400> SEQUENCE: 43
ggcacgagcg gcgacgcgcg ggcggcaaga tggaagacta ccaggccgcc gaggagactg     60
cttttgttgt tgatgaagtg agcaacatcg taaagagggc catagaaagc gccatcggtg    120
gcaacgccta tcagcacagc aaagtcaatc agtggaccac aaacgtagtg agcagacct    180 taagccaact caccaagctg gggaagccat ttaagtacat cgtgacctgt gtgatcatgc    240
```

-continued

```
agaagaatgg agcgggcctg cacacggcaa gctcgtgctt ctgggacagc tccaccgatg    300
ggagctgcac cgtgcgatgg gagaacaaga ccatgtactg catcgtcagc gccttcggcc    360
tgtccatctg acagccgccc cgcccgacct ctctccttcc accacatccc ttctctccca    420
tcttctaaca ccgaccggct atacagcgat ctcctttctc atccaaagtg tgttttttgtg  480 gcactctcaa catgtagaga aaaaaacaaa taaccacact gctcctctgt gacctgcaca    540
ccaagtcaga ggcgtcgtca ccgcaggtag caggagcctg tcctgccgct tgtcttaact    600
ctgaatgttt cttctcaaag gtgctaaaag ccgaaatctg ctagtgtgaa acttctctcta  660 ctctctgaaa cgaatcaaat acactaattt tccatacttt gtacttttg ttagaataat    720 aaattattaa gatttaaaaa aaaaaaaaaa aaaaaaaaa                           759
```

<210> SEQ ID NO 44
<211> LENGTH: 914
<212> TYPE: DNA
<213> ORGANISM: Bos Taurus

<400> SEQUENCE: 44

```
ggtgctgtcg ccgcccggga gccttccggc ccagtcagtg gagcccgtca gcttctctgc     60
gcgggtcagc ccaccccctt cccacccctc cggtgtcccg ggagctggct cggtgcggaa    120
gccgcgcgcc atccattcgg gcatgccccg ctacgagctg gctttgatct tgaaagccat    180
gcagcggcct gagactgctg cggccttgaa gcggacgctg gaagccctga tggacagagg    240
ggcggtggtg aggagcctgg agaacctggg cgagcgcacg cttccctata agatgtcggc    300
ccacagtcag cggcacacca ggggagggta cttcttggtg gactttatatg caccaacaac   360 aactgttgca agcataatgg agcacttgtc tagagacatt gacgtgatta gaccaaatgt    420
tgtaaaacac cctctgaccc aggaagtgaa agaatgtgaa gggatcgtcc cggtgccact    480
tgaagaaaag ctgtattcca ccaagaagag gaagtgagaa ggcaccacac tttagcctcc    540
tgtttaattc tctcacttgt gagcgccacg gatagataat gtacaggctt aatctttata    600
tctgagggtg ctgttggcgc tgttggatttt tccagaggta cttttagctc ttggtcctct   660
ttgctgtgag aactgggggc tgacttcctt agggccactt ggtaatcttt ggcaccagca    720
cgtcctcctt gctttcactt catgagtata atttgtcagt gaggacttcc tgcccaacag    780
caacactaac cccagtttga agagcaaagc tcataaaaac tactttggat tgcatggtca    840
ttattcacac tgtatacacc catgcaaaat aaaattttaa gaccactgta aaaaaaaaa     900 aaaaaaaaa aaaa                                                       914
```

<210> SEQ ID NO 45
<211> LENGTH: 745
<212> TYPE: DNA
<213> ORGANISM: Bos Taurus

<400> SEQUENCE: 45

```
aggacctgac caaaagggca ggagttttaa gatcctggga cgctagggtg agctggcgtg     60
gggggatctc gtccgggcgc tggggaccgc cgctgggaga ggcggtcacc ttctgcgcgg   120
gcggggcgcg caggcagcac agttagttcg ggacgcgccc tggtttgcgg cacttgcagc   180
cgctccactt ccagagctgt ccctgagccc agttctaggg cgaaaatgcc ggctcttcac    240
atcgaagatc tgccagaaaa ggaaaagctg aagatggaag ttgagcaact tcgcaaagaa   300
gttaagttgc agagacagca ggtgtctaaa tgttcagaag aaataaagaa ctatattgaa    360
gaacgttcta gagaggatcc tctggtgaaa ggaattccag aagacaagaa tcccttaaa    420
```

| | |
|---|---|
| gaaaaaggca gctgcattat ttcatgaata actggggaga cacttcctcc tcagtggaag | 480 |
| aggtcgtttg ttgtcgtttt ccaaaataaa accaaccccc ttttaaagga gtaacaatga | 540 |
| aatttaaatg agactttctt aagcgctcac ctagatgtgg tcttgtctga agctgtatg | 600 |
| cctctcatcc ctgtgcacca cacacccctt taagaggac agagagcatc tgatgtgcga | 660 |
| ttatgggaat aaggacacca cttgtgcatg acacacctct ttcagtatat tgcttgacgc | 720 |
| ctcaaataaa gttttatctc tgcag | 745 |

<210> SEQ ID NO 46
<211> LENGTH: 2580
<212> TYPE: DNA
<213> ORGANISM: Bos Taurus

<400> SEQUENCE: 46

| | |
|---|---|
| ctttgagtca gcaaactccg ccacccgctg gcccgctggc cctgctctgc ccggctctgc | 60 |
| ctggaggtgc cgcccgtaag tgacaggcga tctgccggga aggcctccct cgcgccgccg | 120 |
| gattgatcgt gttctgtgtt gaagatgttt ccagaacagc agaaagagga atttgtaagt | 180 |
| gtctgggttc gagatcctag gattcagaag gaggacttct ggcactctta tatcgactat | 240 |
| gagatatgta ttcataccaa tagcatgtgt tttacaatga aaacatcctg tgtgagaaga | 300 |
| aggtacagag aatttgtgtg gctgaggcag agactccaaa gtaatgcatt actggtacaa | 360 |
| ctgccagaac ttccatctaa aaacctattt tcaacatga caatcgcca gcatgtagat | 420 |
| cagcgccgtc agggtttgga ggatttcctc agaaaggttc tacagaatgc acttctgctt | 480 |
| tcagatagca gccttcacct cttcctgcaa agtcatctaa attcagaaga catcgaggca | 540 |
| tgtgtttctg ggcagactaa gtactctgta gaagaagcaa ttcacaagtt tgccttgatg | 600 |
| aacagacgtt tccctgaaga agaggaagga aaaaagaaa acgatataga ttatgattca | 660 |
| gaaagttcat cctctgggtt tggacatagt agtgatgaca gcagttcgca cggatgtaaa | 720 |
| atgagcacag ctccgcagga atcctgaaaa ataattctaa tgttaccatt ttaggaatag | 780 |
| caaattgtgt ccagtcatag agaataaagc ttgcaaataa tatattctta cctaaagctc | 840 |
| actgtcatat taagtatttg aattcgtaaa gatgttgtgt tgtttattag tggtattttt | 900 |
| atgttgtctg attttggcta agcttctgtg aaaagctaaa agcctgtgaa tgcagcactc | 960 |
| tccttgatca gcgcacgcta ttggtaaaat gagatcctgc cctcagatga aatgatttgt | 1020 |
| atgtttaaac aaaatctagt tggctttatt gcattttaaa agataggtaa ataggtagca | 1080 |
| cttcaaatcc agatggagca tttcttcttg tattactggg gcagtgttag cataaacaca | 1140 |
| gcaggtatgt gtatgactta cggcacagac cagaatgcct ctctcagaca ggcagctgga | 1200 |
| attttgtggg tacctcctct gcactggaaa aacactgagc tttggaatgg ttgattgaaa | 1260 |
| tattttaaga gtgtttaacc tttccattat tctatttcac acttagatgg aaaacgtatc | 1320 |
| ttatgaatag agacatgtta aaataatgtt tacatcttta aaaataaaaa gcccagaaat | 1380 |
| agcgctagtc attttgctta tatttgcaat atatagaggg cttccctggt ggcttagcag | 1440 |
| taagaatctg caatatatag attcagaaat acattttcat tgttcaaaat cagctttaac | 1500 |
| acatggtttc tgggaacaaa ccatttgttt tcattatctg tgtgtaatta gaattacagg | 1560 |
| ttcatgattt attttctgac ttaatgtgca atttcttagc actagataac tttcagtatc | 1620 |
| tgtgacggtt gcttgttact ttaagttaaa agtaggatct tataaaaatt aataaaattt | 1680 |
| gccagtaaat attcccataa tatagaagag gatatgaact tgctaatttc agaattaatt | 1740 |
| attcattttt aaaaagtcct ttcttttaag gcatctgcct aaggagtggt ataatttaac | 1800 |

```
aaaatgtctc tttttatagt ggtcaaagat aaaatatctt agataaacta cattgaactt    1860
caaatttcag ataagacagc attttcttga gataactgtt catatttctt ccttgttgaa    1920
tggtatgaaa tatctctgaa attaacaaga agatatcttt atataagggg gataaacttgt   1980 tgctttaatt aaatgttacc tcaccctcat tttaactagg agtttattaa aagttactgt    2040
attattttta aaagtctttg aaatgctgt aactgagact caacagaaaa aattaaattt     2100
agaatatgaa tgatttcctt aattttgcct ttttgttttc tgtttggtct aaaatgttat    2160 tgaactttt gtaaatattt tgatttaatg tatcttggat cttactactt tatcatctaa     2220
gactcattat tttaatactg gaggaaaaaa gatttagcag tttctttta ttttgctgac     2280 atgtgaagtt tgccattcag tcatttcagt gtggtcacca gctccttggc aatatgtatt    2340
tgtattcatg ttctgtttta cagtagtttt gaaaagcata tatcgtgcca ccaattgtaa    2400
ttcttagatg atgaaactat agccgtcaaa attgatatta agtaatgcgt aatactgtgg    2460
tatgtaaact tcatgagatc atcattttca cattaaacat gaaaaaaaca aaaaaaaaa     2520 aaaaaaaaa aaaaaaaaa aaaaaaaaa aaaaaaaaa aaaaaaaaa aaaaaaaaa          2580

<210> SEQ ID NO 47
<211> LENGTH: 553
<212> TYPE: DNA
<213> ORGANISM: Bos Taurus

<400> SEQUENCE: 47
gatcatcaat ggcagccacg gcgttggcgg cgcgtacccg gcaggccgtc tggagcgtct      60
gggcaatgca aggccgaggc tttggctcgg aatcgggaga taatgttagg tccagtgcgg     120
gcgcggtccg ggacgccggt ggggccttcg gaaaaagaga gcaggccgaa gaggagcgat     180
acttccgagc tcgtgctaaa gaacagctgg ccgccttgaa gaaacaccat gaaaatgaga     240
tctctcatca tgcaaaggag attgagcgcc tgcagaaaga aattgagcgg cataagcagt     300
cgatcaagaa actaaaacag agtgaggatg acgactaagt gcacaagttc tccacagaat     360
ggctacctat tatcgcccac ttctatgtag acataattct ggtttaacca aaatcaacct     420
gtgtgcttcc aacaaattat aataaattgt cattagcaaa aaaaaaaaa aaaaaaaaa       480 aaaaaaaaa aaaaaaaaa aaaaaaaaa aaaaaaaaa aaaaaaaaa aaaaagaaa           540 aaaaaaaaa aaa                                                         553

<210> SEQ ID NO 48
<211> LENGTH: 1787
<212> TYPE: DNA
<213> ORGANISM: Bos Taurus

<400> SEQUENCE: 48
cgggcgcggc cggacgggag ttccccggag aaggctcctc tagcccgagt cccggggact      60
ctgtgccggg acgctgctat ggacgacatt ttcactcagt gccggagggg caacgcggtt     120
gcggtccgcc tgtggctgga caacacggag aacgacctca accaggggga cgatcatggc     180
ttctccccct tgcactgggc ctgccgagaa ggccgatctg ctgtggttga gatgctgatc     240
atgcgggggg cacgaatcaa tgtgatgaac cgtgggggatg ataccctct gcacctggca     300 gccagtcatg ggcaccgtga tattgtacag aagctgctgc agtacaaagc tgacatcaat     360
gcggtgaatg agcatgggaa tgtgccctg cactatgcct gtttctgggg ccaagatcag     420
gtggcagagg acctcgtggc aaatgggcc cttgtcagca tctgtaacaa gtatggagag     480
atgcctgtgg acaaagctaa gccaccctg agagagctgc tccgagagcg ggcagagaag     540
```

```
atgggccaga atctgaaccg tataccatac aaggacacat tctggaaggg gactacccgc    600
actcggcccc gaaatgggac tctgaacaaa cactccggca ttgacttcaa acagctcaac    660
ttcctggcga agctcaacga gaatcactct ggagagctat ggaagggccg ctggcagggc    720
aatgacattg tcgtgaagat gctaaaggtt cgagactgga gtacaaggaa gagcagagac    780
ttcaatgagg agtgtccccg gctcaggatt ttctcacatc ccaatgtgct cccagtgctt    840
ggtgcctgtc agtctccacc tgctcctcac cccacccctca tcacacactg gatgccatac    900
ggatccctgt acaatgtgct acatgaaggc accaattttg ttgtggacca gagccaggct    960
gtgaagtttg cattggacat ggcaagggc atggccttcc tacacacact agagccctc    1020 atcccacgac atgcactcaa cagccgtagt gtaatgattg atgaggacat gactgctcga   1080
atcagtatgg ccgacgtcaa gttctccttc cagtgccccg ggcgcatgta tgcacctgcc   1140
tgggtggctc ctgaagctct gcaaaagaag cctgaagaca caaacagacg ctcagcagat   1200
atgtggagtt tgcagtgct tctatgggaa ctggtgacac gggaggtacc ctttgctgac    1260
ctctccaaca tggaaattgg aatgaaggtg gcactggaag gccttcggcc taccatccca   1320
ccaggcattt cccccacgt atgtaaactc atgaagatct gcatgaatga agaccctgct   1380
aagcgaccca gtttgacat gatcgtgcct atcctggaga agatgcagga caagtagagc   1440
tggaaagtcc ttgtctgaac ttcagaggtg tcaggacacg gttaggggag tgcacctccc   1500
caaagcagca ggcctctggt tgcctccctt gccactagtc atggtactac cccagccatg   1560
gggcccatcc cctgccccca tccctaccac tgtggcccca aagggaatg ggctcaaagc    1620 tttgtcactt gccacacggt gtctcccagc atgggaggga tcagccctgc ctgtcacaat   1680
aaagtttatt atgaaaacaa aaaaaaaaaa aaaaaaaaaa aaaaaaaaaa aaaaaaaaaa   1740
aaaaaaaaaa aaaaaaaaaa aaaaaaaaaa aaaaaaaaaa aaaaaaa                1787

<210> SEQ ID NO 49
<211> LENGTH: 441
<212> TYPE: DNA
<213> ORGANISM: Bos Taurus

<400> SEQUENCE: 49
tgttcacaga gttgcttatt atgaaaagag taattaaaat catgtaatca tttaaatgcc     60
acacttaaca ctgttcaccc ttctgttaat tcacacaact cattatttt gctttgttca    120 aagttttcct tcaccgctga gatattatgt cagtttacaa atgattttaa taaaatctta    180
aatttgtgtc acatgttgtt tcttcagttt aaaaaaaaat tgaatcttgg cgtatacctt    240
ttcttgttga cttttacccc acaatgatct atctcgtcca atttattggt cgtcgatgat    300
aaattctgaa actttctgtg aaagaaatgc agaattaaat gagttggttt cttctcacat    360
tgatatgtca gtttttttt tttcttctct cttgaagac tgtttctaaa ttaggaagaa      420
gcagaaaaac aaatctctgg a                                               441

<210> SEQ ID NO 50
<211> LENGTH: 633
<212> TYPE: DNA
<213> ORGANISM: Bos Taurus

<400> SEQUENCE: 50
acacttgctt ctgacacaac cgtgttcact agcaactaca caaacagaca ccatgctgac     60
tgctgaggag aaggctgccg tcaccgcctt ttggggcaag gtgaaagtgg atgaagttgg    120
tggtgaggcc ctgggcaggc tgctggttgt ctacccctgg actcagaggt tctttgagtc    180
```

```
ctttggggac ttgtccactg ctgatgctgt tatgaacaac cctaaggtga aggcccatgg      240
caagaaggtg ctagattcct ttagtaatgg catgaagcat ctcgatgacc tcaagggcac      300
ctttgctgcg ctgagtgagc tgcactgtga taagctgcat gtggatcctg agaacttcaa      360
gctcctgggc aacgtgctag tggttgtgct ggctcgcaat tttggcaagg aattcacccc      420
ggtgctgcag gctgactttc agaaggtggt ggctggtgtg gccaatgccc tggcccacag      480
atatcattaa gctcccttc ctgctttcca ggaaaggttt tttcatcctc agagcccaaa      540
gattgaatat ggaaaaatta tgaagtgttt tgagcatctg gcctctgcct aataaagaca      600
tttattttca ttgcaaaaaa aaaaaaaaaa aaa                                   633

<210> SEQ ID NO 51
<211> LENGTH: 975
<212> TYPE: DNA
<213> ORGANISM: Bos Taurus

<400> SEQUENCE: 51
tttatcagga ctcctcagtt caaccttctg aacatgagat tccctgctca gctcctgggg      60
ctcctcctgc tctgggtccc aggatccaat ggggatgttg tgctgaccca gactcccctc     120
tccctgtctg tcatccctgg agagacggtc accatctcct gcaagtctac tcagagtctg     180
aaatatagtg atggaaaaac gtatttgcaa tggtttcaac ataaaccagg ccagtctcca     240
cggctattga tctggcagat ttccaaccgt aacactgggg tcccagacag gttcactggt     300
agtgggtcag agacagattt cacacttaca atcagcagtg tgcaggctga ggatgctgga     360
gtctattact gtcttcaaag atctgatgat ccacatactt tcggccaagg aaccaaggta     420
gagatcaaaa ggtctgatgc tgagccatcc gtcttcctct tcaaaccatc tgatgagcag     480
ctgaagaccg gaactgtctc tgtcgtgtgc ttggtgaatg atttctaccc caaagatatc     540
aatgtcaagt ggaaagtgga tggggttact cagagcagca gcaacttcca aaacagtttc     600
acagaccagg acagcaagaa aagcacctac agcctcagca gcatcctgac actgcccagc     660
tcagagtacc aaagccatga cgcctatacg tgtgaggtca gccacaagag cctgactacc     720
accctcgtca agagcttcag taagaacgag tgttagagca agaggtctac aggctcccca     780
gtcacctgtg ctgattcggt cccagcccct caccctcct caggccctt gtccacagat     840 caaccctat tgcaatcctc tgacccatct ccccacctca tccccctccc cctctttggc     900
tttaatcgtg ctaatgttgg ggggacaatg aataaataaa gtaaatcttt gcacctgtga     960
aaaaaaaaaa aaaaa                                                       975

<210> SEQ ID NO 52
<211> LENGTH: 649
<212> TYPE: DNA
<213> ORGANISM: Bos Taurus
<220> FEATURE:
<221> NAME/KEY: misc_feature
<222> LOCATION: 380
<223> OTHER INFORMATION: n = a, c, t, or g

<400> SEQUENCE: 52
tttttcaggg ttaatatgta gcgctatttt catttcgctt ttttaattct gcttttgtaa      60
aagcagtatt gagattgaca ttttgatctt cattgtatcg ttatttttat ttttcatcaa     120
ttcattattt ttgtggatac agcttgataa gccattaact ttatagtagt agattccatt     180
aactttaaat tggtagtttt catttgcttt tttttttgca tgtgcagaca atgtgttcat     240
cagaagaaaa tctcagggtt atgcttttt ccccaatgta ggtatgaaat acaatctttt     300
```

```
ctgcctttac ttatcattca ccaaggagct gttcccctct ccatctaggc catcagactg      360
ccaggctggt tatgactcan aagatgttat ctgaaaaaag tctacaaaaa aaaaaagagt      420 ttccccctccc tcatcaacaa agcccacccc cctcttatca gttatgattt acaaggctta    480
gatgtaaatt caaaatacaa ttaacaataa ttttgaagca taccttaaca acaaacttt      540 cctacgctaa aaagaaaag aataaaccaa acaatcttgc ttatatacag ccgaaaaag       600 aatcttactt gataatacaa aagctaccac cagaagaaat cccttgcaa                 649

<210> SEQ ID NO 53
<211> LENGTH: 427
<212> TYPE: DNA
<213> ORGANISM: Bos Taurus

<400> SEQUENCE: 53
ggaggaagag ggaagaaaaa aataatttta gaacctgagg gaggttaaga gctgaaattt      60
tttcatggag tgaaaaattt aaaagaattg atgagctagg actgcaatgt ctggattttt    120
tttttaaagc cttaacttga agggcaacct tttaccttaa cattaaaacg ttgggttacg    180
taaatcgaac ctaaacgttt taaaaggttg agttgtaggt gattaaaata ctacaaaggc    240
catcttaaga tttaactgaa ggtggtttca gaaataatgc cttcagattc acggcgcagt    300
aaaaatggcg tcatttgaag cctgcttgat actaaggctt tgtttggcta agttgacgg     360 aaatattagg aatggtagga aagaaaattg gaagtttgaa gtgaaaaaag agaagaaaaa    420
aaaggaa                                                              427

<210> SEQ ID NO 54
<211> LENGTH: 1409
<212> TYPE: DNA
<213> ORGANISM: Bos Taurus

<400> SEQUENCE: 54
agaacagcgt tcccagcggg agagagataa tgcaaagtgc tctgttcctg gctgtccagc      60
acgagtgcgg acccatggac aaaggcgctg gcaccggccc caagaacgag gagaagcgag    120
agaagatgaa gcgaacccta ttaaaagatt ggaagagccg tttgagctac ttcttgcaaa    180
attcctcctc tcctgggaag cccaaaactg gcaagaaaag caaacagcaa accttcatca    240
agccttctcc tgaggaagcc cagctgtggt cagaagcatt tgatgagctg ctagccagta    300
aatatggtct tgctgcattc agggcttttt taaaatctga attctgtgaa gaaaatattg    360
aattctggct ggcctgtgaa gacttcaaaa aaaccaagtc accccaaaag ctgtcctcaa    420
aagcaaagaa aatatatact gacttcatag aaaaagaagc tccaaaagag atcaacatag    480
actttcaaac caaaagtctg attgcccaaa acatacagga ggctaccagt ggctgcttca    540
caactgccca gaaaagggtg tacagcttga tggagaacaa ctcttatccg cgtttcttgg    600
agtcagaatt ctaccaggac ttgtgtaaaa agccgcagat caccacagaa ccccatgcca    660
catgagatga agcgggagc ccagaaatgg gggactttc attttttttc ctaaggggaa      720
aggctgtcac ctgccgaaaa gactgacctt gaattcagcc tgggtgttca ggaaacatca    780
ctcagaacta ttgattcaga gctgggtagt gaatcaggaa gccggtcgcc acgtaggaga    840
agctggtact ggggcagctt ccgtaactga tggagcacag agagagagtg tggtttaaat    900
gtggtgtgtc tcaagctgga gaagcaggag cttaagactg aaagataaca atgtaacact    960
attggtccag aagcatttac aatcaatagg tctgggatta tgtggcctca gctagctggc   1020
tgtacatctt tccctaaatc agtccttgtt accacatagt ggtttagatg tagcttcttt   1080
```

```
agttctaggt aatatatgtt tactatgtgc aagggtactg aagttcctat gtctacagat      1140
catcagtact gttgtctcac ataactctaa aactgaaatg attgtgtttg aactgtcaat      1200 tggtgttttgt tctagaatga gtgcttttgt gtagaaaatg acaatgtcca ttatgagtgc    1260
caaaactgtc ctgatggcag ctaaactttg aagtggtctt tgaatacttt taataaattt      1320
attttgataa ataaaaaaaa aaaaaaaaaa aaaaaaaaaa aaaaaaaaaa aaaaaaaaaa      1380
aaaaaaaaaa aaaaaaaaaa aaaaaaaaa                                      1409

<210> SEQ ID NO 55
<211> LENGTH: 1651
<212> TYPE: DNA
<213> ORGANISM: Bos Taurus

<400> SEQUENCE: 55
ctctggctgc aggatctcag gtcccagcgg caggacccta agccaccatg tgcttcgcta       60
agagagaccc acgtgtcctg gcttctttca gggtgttatc gcacaacctt gtagatgaat      120
ttttcgatac aatggaaaat gaaccagaag gagcacagga aaattcatc aaggacgcct       180 ttaaagtcat ggataatcac attcaagaga acagtcccga aaccctgaag gagtccagtc      240
ccttgcttca ggaagcacag caagaagtac gctgcagaat ccagagacgc tccgtctcca      300
cctctctgga ggtccagaat ccggaagaga gcatctgggc cagagccctg cggcagttct      360
tgggcattct gcagagtttc ctgtccgggt gtcgggatgc gctcacctgg ctgtgggaga      420
aggccgcggc ctgcctacag gccgtctgca gtgcggtgga ggccctctgg gaagtgctca      480
cggatttctg ctcctttgtt gggcagctct tatgcagaag cctcatccag gtctaagagc      540
ctcacatggt tctggaggag ccccacctca ttcagaaggc cctgtacgat gcccttcccg      600
gaaaccatct tctgaagcga ccttta ccct cctgctcacc cttgacccat cctttaactg      660
ccctcccctc ctgtcctgca gggacgacac cacagcatca ggccaggttt ccttctcca      720 ggtctgacct gtctgtcagg acggggatg ttctgctgac ccagggacgt gggagaggct      780
tggaagccca gaggccccaa ggaccaaggt gccttccgtg ggtcagcatg cctcagtgtc      840
tctgcctgtc gctccagacc ctgtcagatg gggcgctgag ctgatcctca gcgaggggga      900
cccctgaggg ccggctgcgg gtctcgcagg aggagtcagt ggtggaccct gaccctgaca      960
ttagcatctt agtgccctca tcatcctaag cgacccagct tgctgtcagc tgaggcccca     1020
gcagggcagg agacctggag gaaggctctc cctgtctcct gggcctgtgc cttcctgtct     1080
gaggaggaca gcagcctgtc tgggagttcc ttgtggcaga gccccattcc gggcatatcc     1140
ttcccccttc acttcagag gtccctctg acaggcctga cactggaagg cctacctctg      1200
gcctgagttc cctgctgcaa ggagccgccc actgccaggc cctgagcagc cttggcttcc     1260
tggccccgtc cctgcctcac ctccccatca gtatgcaagt ccctcagact ttcctctgtt     1320
ctctgatgcc cctgtgctaa acctgcactt gactatttcc tttttttctt tttacataat     1380
gacttacatc tgatattcta cttctcacga tggtgattat agccgttgat agaagtagta     1440
tggatgtttt gtttaacatt aaatttcttc cccgtttcaa catcaatatg agtttgtttt     1500 tattttttgtt gttgttgttt ttagattaaa tcttttctcc atttcaatgt aagttacatg    1560
aaatacattt tctaaacact ttccctccca aggaaatgtt tcagttttgg accaatgata     1620
tgtgatttgt gcatggacaa tataaactcg g                                   1651

<210> SEQ ID NO 56
<211> LENGTH: 2487
```

<212> TYPE: DNA
<213> ORGANISM: Bos Taurus

<400> SEQUENCE: 56

```
gcaaactatc gtttcgtctt ctgaggtgga acgctttaag cctgcccgcc gagagccgga      60
gctttcctcc agctgttaga agaaagagc ttattttct cttgcaatct tttgatataa       120
ctcgcgactt acattttgg gtggacgtgt tttcgaaaat ttagtagaga attgagaagt      180
gaaaaagttt taacttacag caaagggtcc tttgagagtt ttgttttgtc ctcatttta      240
actgttaagc aaatccagcc caacatggtg atgttcaaga agattaagtc tttcgaggta     300
gtctttaacg accccgaaaa ggtgtacggg agtggggaga aggtggctgg ccgggtgata    360
gtggaagtgt gtgaagtcac tcgagtcaaa gctgtcagga tcctggcttg cggagtggcc    420
aaagtcctgt ggatgcaggg atcccagcag tgcaagcaga cgttggacta cttacgctac    480
gaagacacgc ttctcctgga cgaccaacca gctggtgaga atgagatggt gatcttgaga   540
cctggaaaca aatatgaata caagttcggc tttgagcttc ctcaggggcc tctgggaaca    600
tctttcaaag gaaaatatgg gtgtgtggac tactgggtga aggcttttct tgatcgtccc    660
agccagccaa ctcaagagac aaagaaaaac tttgaagtga tggatctagt ggatgtcaat   720
actcctgatt tactggaacc tgtgtcagct aaaaaggaga gaaagttttc ctgcatgttc    780
atacctgatg ggcgggtgtc tgtctctgca cgaattgaca gaaaaggatt ctgtgaaggt   840
gatgagatta acatccatgc tgattttgaa aatacgtgtt cccgcatcgt gatccccaaa   900
gctgccattg tagcccgcca cacttatctt gccaatggcc aaaccaaggt gctgacgcag   960
aagttgtcat cagtcagagg caatcatatt atctccggaa cctgtgcatc atggcgtggc  1020
aagagccttc gggtgcagaa aatcaggcct tctatcttgg gctgcaatat cctgcgagtt  1080
gaatactcct tactgatcta cgttagcgtc cctggctcca agaaagtcat tctcgacctg  1140
cccctggtta ttggcagcag gtcaggcctc agcagccgga cgtccagcat ggccagccaa  1200
accagctctg agatgagctg ggtagacctt aacatcccag ataccctaga agctcctcct  1260
tgctatatgg atagcattgc tgaagatcac cggttggaga gccccactac tcctctgcta  1320
gaggacacag atggttctca agacagccct attttatgt atgctcctga gttcaggttc  1380
atgccaccac ctacttattc tgaggttgat ccctccgtcc tgaacaacaa tgtgcagtga  1440
gcatgtggaa gaaaagaagc agttgtacct acctgtttct cttcatctct cttcctggac  1500
tctttaattt tttagagact caacagtctc cacagtgggg tacaggtcca ccccagcctc  1560
ttgactctcc agtgtgggag gtgatcagca ggcaatctcc tgggccttaa agggtgcgca  1620
ctcgtcctca gccagcgaga tgatgtgata cagagttttt tgctagatgg gtttaaaaac  1680
acgttagaaa aaaaactaag gcccatccca ttttcttgaa tctctttgaa aattgaggca  1740
ttttcagtag ttttgagtaa ggggtagaaa tggcatcctg gaatggtgtt cccacggttg  1800
aatgagggg attatataat agagatattg ttataacaat agatcttgaa cctctgccat  1860
gtggaggaga gccaatttag caaactaaga aagtgaaaag aaaaaatggt catggccaaa  1920
actttgggaa aaggatgttc ttaaaatcat tgttccccat tgtttgtaca cttacagaaa  1980
aagaaaagcc ctccagaatt gattgggttt ggacttttga gcaagcttcc cattcgaatt  2040
aaagggagg agctcttaag tttcattgtt cagaaagtag ttttaatcag tcataaggca  2100
gtagtaactg ggccccacca gaggtcttaa aagccatttt tagagcttgt tgcactgtgt  2160
tctcctgttg gcaaacattt ttatgtggga gaattttttt ttttcatgtg actccttgga  2220
attgattctg aggcgatgtc cttagcactt tagtttgtgt caaatttggg ttttcctttc  2280
```

| | |
|---|---|
| tcagatgtaa gctaaaactg gtctactatg tctctagggg taagcacaat gacagggaaa | 2340 |
| aaaaagtgtt actgcttttg agactttgtc gcagtgtacg gaattctgca gttctgacac | 2400 |
| tgattacgta agggttgctg ctatcagcct tgcccactgt gacttctcca acccaagga | 2460 |
| ggaaccctag ataaaatgcc ccaacac | 2487 |

<210> SEQ ID NO 57
<211> LENGTH: 1416
<212> TYPE: DNA
<213> ORGANISM: Bos Taurus

<400> SEQUENCE: 57

| | |
|---|---|
| gattctgtga aatgggctca ccagatccac tgtgtttgag ctgtgttgac taccattact | 60 |
| tcttcctttg ttctctatta tgtctgggat ggtggctctg tggatcccca gaggcctttg | 120 |
| gacagcagct gtgatggtga cactggcggt gctgagtacc caggggccg agggcagaga | 180 |
| ctcgccacag gataccgtgg tccactttat gtgccagtgt tacttcacta atggcacgga | 240 |
| gcgggtgcgg tacgtgacca gatacatcta caaccaggag gagaccgcat actatgacag | 300 |
| cgacgtggga gagtaccggg ctgtgaccca actaggcgg actttggctg agtattggaa | 360 |
| cagccagaaa gatatcctgg agcagacacg ggcggagctg gacacggtgt gcagacacaa | 420 |
| ttaccagctg gaggtcatca cgtccttgca gcgccaagtg gaacctacag tgaccatctc | 480 |
| cctgtccaga acagaggctc taaaccacca caacctgctg gtctgctccg tgacggattt | 540 |
| ctatccaggc cagatcaagg ttcggtggtt ccagaatggc aaggaagaga cagccggcat | 600 |
| tgtgtccacc cctcttatta ggaatgggga ctggacattc cagatcctcg tgatgctgga | 660 |
| aatgaccccc aagcgaggag atgtctacac ctgccgcgtg gagcacccca gcctccaaag | 720 |
| ccccatctcg gtggagtggc gggctcagtc tgaatctgcc cagagcaaga tgctgagtgg | 780 |
| tgttggtggc tttgttctgg gcctgatctt ccttggtctg ggcctcatcg tccgtcgcag | 840 |
| gagtcagaag gggctcatgc actgactcct gaggatgctt tgatggggat tggttttgct | 900 |
| cttctgtaat agctgcctgt tcttgtccag aattctcagc tgcctgccat cctgttccac | 960 |
| tgagatcagg tcctacagtg actctgacgc agtcatcagg tcacttcctg tgaccctgc | 1020 |
| ctcaaggatc tggctgcttc ttgcactgac ccctgaagcc tcttctagct gcatctactc | 1080 |
| agaccccaag agttttttctg tttccatttt tccagagcag actgtgggag agaagcacat | 1140 |
| tgaaaccatt tgcctggcta tagaatttt ttatcatgat taaacatgat tatgagttac | 1200 |
| ctgtattctt aagctcctta aatgcatgga ggtagggaac cactgcagaa tgaaggaaca | 1260 |
| cattttgagg tgacccagac aattggcaac tagaaggaga agttattccc tgaaggatac | 1320 |
| tagaagcatc atggtgtgcc atgtaagcat ggatagaaga gaaataaaat caattttct | 1380 |
| ctaaaaaaaa aaaaaaaaaa aaaaaaaaaa aaaaaa | 1416 |

<210> SEQ ID NO 58
<211> LENGTH: 1690
<212> TYPE: DNA
<213> ORGANISM: Bos Taurus

<400> SEQUENCE: 58

| | |
|---|---|
| agtgtgttgg ctgtggcagc aggtagcaaa gtgaccctga ggacttgagt agccggtagc | 60 |
| ccccgcggct ggagagcaag cggttaccat ggaagggatc cgtatattca cttccgataa | 120 |
| ttacaccgag gatgacttgg gctcgggtga ctatgattcc atgaaggaac cctgcttccg | 180 |
| ggaagaaaat gcccatttca accggatctt cctgcccact gtctactcca tcatcttcct | 240 |

```
gactggcata gtgggcaacg gattggtcat tctggtcatg ggttaccaga agaaactaag      300
aagcatgacg gacaagtaca gactgcacct gtctgtggcg gacctcctgt ttgtcctcac      360
gcttcccttc tgggcagtcg atgctgtggc aaactggtac tttgggaagt tcctctgcaa      420
ggcagtccat gtcatctaca cagtcaacct ctacagcagt gtcctcatcc tggcctttat      480
cagtctggac cggtacctgg ctatcgtcca tgctaccaac agtcagaagc aaggaagct       540 gctggctgaa aaggtggtct atgttggtgt ctggctacct gctgtcctgt tgactattcc      600
tgatctcatc tttgctgaca tcaaggaggt ggatgagagg tacatctgtg atcgcttcta      660
tcccagcgac ctgtggctag tggtgtttca gtttcagcac atcgtggtcg gccttctcct      720
gcctggtatc gtcatcctgt cctgctactg cattatcatc tccaagctgt cccactccaa      780
aggctatcag aagcgcaagg ccctcaagac cacagttatc ctcatcctga ctttcttcgc      840
ctgctggctg ccctactaca ttgggatcag cattgactcc ttcatccttc tggaaatcat      900
ccagcaaggg tgtgagtttg agagcactgt gcacaagtgg atttccatca ccgaggccct      960 agctttttt cactgctgcc tgaatcccat cctctatgcc ttccttgggg ccaaatttaa      1020
aacctctgcc cagcatgcac tcacctctgt gagcagaggg tccagcctga agatcctctc      1080
caagggcaag cgaggtggac attcttctgt ctcaaccgag tctgaatctt caagttttca      1140
ctccagctaa cactggactt tgtacatta aagaactttt tttttgaagtt acacattttt      1200 tcagatgtaa aagactgacc aacactgtac agtttttatt gactgttgga tttttttctt      1260
gtgtttgttt agttttttgtg aggtttaatt gacttattta tataaatatt ttgtttcatg      1320
ttgataagtg tctaggcagg acctgtggcc aagttcttag tgctgtgtgt cattgtagga      1380
ccgtagaaaa gggaactgaa cattccagtg tgtatagtga aatcacttag gctagaaatg      1440
attctcagct atttgtaaat aagtgatctc tccattccag tgaaacattt tcttttttcct      1500 gttcttaaat tctttggtta taccatgtga ttttgctgta gaacatggca tttataacca      1560
aagcctgaag tgatatggaa atactggttt ttcagttttc agaagtggat caatttccac      1620
acctacaatg tacagccttg tattaagttg ttaataaaac tacatgataa acccaaaaaa      1680
aaaaaaaaaa                                                             1690

<210> SEQ ID NO 59
<211> LENGTH: 619
<212> TYPE: DNA
<213> ORGANISM: Bos Taurus

<400> SEQUENCE: 59
agaaaaaaaa aaagagcaaa gtttattgaa atttcaagct acatttgaaa aatcaaaatc      60
caaatcctgg agacataaca tcaggataag gtgttagaaa gtgggaagtg ttcactgcca      120
cagaactccc tagagacaag ctccctgagc acatcacgca ggcatcattg ggtcagttac      180 tccccttgtcc atgaaaggac accggctagc tgatcgttct ctgcacttga agttttcca      240 caaccgttaa aaacaaaaca aagttttcag atgacaaagt cccagctgat cttctctcaa      300
ccccattcta tgtagtcagc accagtgaat ggtgggtttg gcattcagaa ggggacctca      360
catgtattca ggggacatat ggggccaagg ttgcagcagc aaggcattta gaggctggcc      420
ccctccctgc ctttactctt ttttttaata taaattgact tattttaatt ggaggctaat      480
tacaatattg tattggtttt gccatacatc aacatgaatt cgccacgggt gtactcttgc      540
ctttactcct tagttttact taacctaaag gacaaactgg atcgacttgg taaatgaaca      600
gatctaagaa ttagcctta                                                    619
```

<210> SEQ ID NO 60
<211> LENGTH: 1661
<212> TYPE: DNA
<213> ORGANISM: Bos Taurus

<400> SEQUENCE: 60

```
cgcacttgtc ccagcagtcc tcgctgaccg cagtaactgc gtcttctgag ctccagcacc      60
ctgagctcat cggcagacgc cctggcgtcc atcctcacta tgcctagcct ttgggatcgc     120
ttctcgtcgt cctcttcgtc ctcgtccttg tcccgaactc ccaccccaaa tcagccgccg     180
cgctcagcgt gggggtcggc ggcccgagaa gaaggactcg gccgctgcgg gagcctggag     240
agctcggact gcgaatccct ggacagcagc aacagtggct ttgggccgga ggaagactct     300
gcatacctgg atggggtgtc cctgcccgac ttcgagctgc tcagcgatcc cgaggatgag     360
cacctgtgtg ccagcctgat gcagctgctg caggagagcc tggcccaggc ccgactgggc     420
tcgcggcgcc ccgcgcgcct gctgatgccg ggtcagctgg tgagccaggt gggcaaagaa     480
ctactgcgcc tggcctacag cgagccgtgc ggcctgcgag gggcgctgct ggacgtctgc     540
gtagagcagg gcaagagctg ccacagcgtg gggcaactgg ccctcgaccc cagcctggtg     600
cccaccttcc agctgaccct cgtgctgcgc ctggactcac gcctctggcc caagatccag     660
gggttgttta gctctgccaa ctctcccttc gtccctggct tcagccagtc cctgacgctg     720
agcactggct tcagagtaat caagaagaaa ctgtacagct cggagcaact tctcatcgag     780
gagtgttgaa cttgggcctg gggggccgat aacgccccca tgtcagagac aattttgaac     840
ttttggggtg gggggcaagc agaggctgag ggactggtgc ctgcccttag aaaactgaca     900
acagccacct gagggtagaa aagtcaaggt gggggggaaca cagtgtttcc ctaggaagct     960
cactgaggtg tgagctggtg gctcccagtt ggaggcacgc actgcccctc agtactgtag    1020
catgaacaaa ggcttagggg ccaaccaggc ttctgactgg atgtgtatgt agcatgtacc    1080
cagttatttt tactgttact gacagttaag gcaacagtgg tgtgacagag ccgggagagc    1140
agctgggctg ctctggcctc ttcgagggat gtgtgtttca ccatagctgg ccctggtggg    1200
aggggggggag gtcatcgagg tgattcgtgt atctcatggt ctgaagggcc caaatgtttg    1260
gttcttttgtt tttgttttttt gatcatagct tcactactga cctgttcgag gcagctatct    1320
tacagacgca tgaatgtaag agtaggaaag gggtgggtgt taggatcact tggggatctt    1380
tgacacttga agaataaata cacctgggag ctgtgtgtgg cccatccttg gatgtgtact    1440
aaagggttga gctgtgaggg gatggggctg attggggtag gggctggcac ccctccccca    1500
gaggagtacc atctggatct tccatctaga actgtttaca tgaagatact cgctgttcat    1560
gaatacactt gatgttcaag tattaagacc tatgcaatgt ttttacttt tctaataaaa    1620
aaaagtttgt taaacaaaa aaaaaaaaaa aaaaaaaaa a                          1661
```

<210> SEQ ID NO 61
<211> LENGTH: 1878
<212> TYPE: DNA
<213> ORGANISM: Bos Taurus

<400> SEQUENCE: 61

```
agagcccgtc ggagctggaa atgcaactgt tgggagcttc ggaggctgcg gagctggagg      60
cggaggcggc tgggggaggtc cgagcgatgt gaccaggccg ccgtcgctcg tttcttccac     120
tttcctgccg cctcctgtgt cgaaaataac tttttttact ataaagaaag gagaaaaaaa     180
agtagccgta cgccgctcac gccctctctc cctctcagcc ctctgacttg tgagggagcc     240
```

```
cggggtggcc gctcctccgt cggggccgcg ccgccgagcc ccggccgccc cgggccgccc      300
ccgcccgccg cccccatgca tcccttctac agtcgggccg ccaccatgat aggcgagatc      360
gccgccgccg tgtccttcat ctctaagttc ctccgcacca aggggctcac gagcgagcga      420
caactgcaga ccttcagcca gagcctgcag gagctgctgg cagaacatta taaacatcac      480
tggttcccag agaagccctg caagggatca ggttaccgtt gtattcgcat caaccataaa      540
atggatcctc tgattggaca ggcagcgcag cggattggac tgagcagtca ggagctgttc      600
aggcttctcc caagtgaact cacgctctgg gttgacccgt acgaagtgtc ctacagaatc      660
ggcgaggatg gctccatctg tgtgctgtac gaagcctcac cagcaggagg tagcacccaa      720
aacagcacca acgtgcaaat ggtagacagc agaatcagct gtaaggagga acttctcttg      780
ggcagaacaa gcccttcgaa aaactacaat atgatgactg tatcaggtta agatatagtc      840
tatggatgga tcatcttata atggatggat aaatttgatt tttgctttgg gtgggctccc      900
cttggggatg gattatggaa tttaaaccat gtcacagctg tgaagatctg cacaagata       960 gagtggtaaa aaaatttttt taagtgacag tgccatagtt tggacagtac ctttcaatga     1020
ttttaatagc ctgtgagtcc aagtaaatga tcatcttatt tgctaggagt gaagtcctag     1080
gatggtttca gtttctccca gacatgatac ctaaattttt acgtcagtcc ctttaatgca     1140
aatctgtatt tctttgcagt agaacttgca gagaagattt gcactattac tcttaaaact     1200
tgttatcctt tttggcagct aataggaaa gctcaacatt ttaaacatgg aaatactgga      1260
aattttatga caagactttt acctagcact taaatatgta taaatgtata taagacaaac     1320
tagtaagcat gacctgggga atggtcaga ccttgtattg tgttttggc cttgaaagta       1380 gcaagtgacc agaatctgcc ttggcaacag gcttaaaaa aaaaaagac ccttaaaaag       1440 acactgtctc aactgtggtg ttagcaccag ccagctctct gtacatttgc tagcttgtag     1500
ttttctaaga ctgagtaaac ttcttatttt tagaaagtgg aggtctggtt tgtaactctc     1560
cttgtactta attgggtaaa agtcttttcc acaaccacc atctattttg tgaactttgt      1620
tagtcatctt ttatttggta aattatgaac tggtgtaaat ttgtacagtt catgtatatt     1680
gattgtggca aagttgtaca gatttctata ttttggatga gaattttc ttctctctat       1740 aataaattgt ttcttatctt ggcattttaa aaaaaaaaa aaaaaaaaaa aaaaaaaaa       1800 aaaaaaaaaa aaaaaaaaaa aaaaaaaaaa aaaaaaaaa aaaaaaaaa aaaaaaaaaa       1860 aaaaaaaaaa aaaaaaaa                                                   1878

<210> SEQ ID NO 62
<211> LENGTH: 1126
<212> TYPE: DNA
<213> ORGANISM: Bos Taurus

<400> SEQUENCE: 62
ggtaccttcg ttgccggaca cttcttgtcc tctactttgg aaaaaaggaa ttgagagcca       60
tgaaggtcct catccttgcc tgcctggtgg ctctggccct tgcaagagag ctggaagaac      120
tcaatgtacc tggtgagatt gtggaaagcc tttcaagcag tgaggaatct attacacgca      180
tcaataagaa aattgagaag tttcagagtg aggaacagca gcaaacgag gatgaactcc       240 aggataaaat ccacccctt gcccagacac agtctctagt ctatcccttc ctgggcccca      300
tccctaacag cctcccacaa aacatccctc tcttactca aacccctgtg gtggtgccgc       360 cttccttca gcctgaagta atgggagtct ccaaagtgaa ggaggctatg gctcctaagc       420
aaaaagaaat gcccttccct aaatatccag ttgagccctt tactgaaagc cagagcctga      480
```

```
ctctcactga tgttgaaaat ctgcaccttc ctctgcctct gctccagtct tggatgcacc      540
agcctcacca gcctcttcct ccaactgtca tgtttcctcc tcagtccgtg ctgtcccttt      600
ctcagtccaa agtcctgcct gttccccaga aagcagtgcc ctatccccag agagatatgc      660
ccattcaggc ctttctgctg taccaggagc ctgtactcgg tcctgtccgg ggacccttcc      720
ctattattgt ctaagaggat ttcaaagtga atgccccctc ctcactttttg aattgactgc     780 gactggaaat atggcaactt tcaatccctt gcatcatgtt actaagataa ttttaaatg       840 agtatacatg gaacaaaaaa tgaaacttta ttcctttatt tattttatgc ttttcatct      900 taatttgaat ttgagtcata aactatatat ttcaaaattt taattcaaca ttagcataaa     960
agttcaattt taacttggaa atatcatgaa catatcaaaa tatgtataaa ataaatttct    1020
ggaattgtga ttattatttc tttaagaatc tatttcagtt caattttaac ttggactaac    1080
cagtcatttc aataaattaa tccttaggca taaaaaaaaa aaaaaa                   1126
```

<210> SEQ ID NO 63
<211> LENGTH: 400
<212> TYPE: DNA
<213> ORGANISM: Bos Taurus
<220> FEATURE:
<221> NAME/KEY: misc_feature
<222> LOCATION: 80, 83, 85, 88, 99, 113, 118, 123, 132, 134, 138, 143,
      144, 168, 169, 174, 181, 184-186, 192, 193, 199, 204, 270, 275,
      287, 293, 294, 304, 318-320, 324, 341, 354, 359, 384, 389,
      398, 399
<223> OTHER INFORMATION: n = a, c, t, or g

<400> SEQUENCE: 63

```
atgtgttgtc atgcagatat aggctgacta ggagagtgaa tacataggct tggattatag       60
ctactgcaaa ctctagaatn gtnantanga ttaaatgggn aatgtaatta ganctgtngt      120
acngctaatg cntnttantg canntgtagc tcctccgatt aagtgaanna atangtgtcc      180
ngcnnngatg tnngctgtna accncacggc cagggctata ggttgaataa aaaggctgat      240
agtggcaata attactagta ttgggattan tggantgggt gttcctngtg gtnngaaatg      300
ggcnagtgat gctttagnnn catngcgcga atcctgtaat nacgagctcc tgcncacang      360
gggatggcta tgcctaggtt tatngatant cgtgttgnng                           400
```

<210> SEQ ID NO 64
<211> LENGTH: 2130
<212> TYPE: DNA
<213> ORGANISM: Bos Taurus

<400> SEQUENCE: 64

```
ggcgaaagac ttcggggctc tgggtgaacc gcgggtggaa gagccgtagg gagagcaaca       60
aggaagccga ggcggtcgag agtcccacac aacgacccct cgctcggtcc aaaggcagtt      120
tgggtttggc gtaaagaaaa ccggggtcgg gcttttcctc gaaagccatc gccctgctgt      180
tcgcttcccg ggacaaagaa cacaggacga cttgcacgct gggggcgctg gggccggcca      240
tggtcatgga agtggtctct ctggacgccg gaggcctccg gacgctgctg agggagcgcg      300
cggcgcagtg cttgctgttg gactgtcgct ccttcttcgc tttcaacgcc ggccacatcg      360
ccggctcggt caacgtgcgc ttcagcacca tcgtgcgtcg gcgggccaag ggcgccatgg      420
gtctggagca catcgtgccc aacgccgagc tgcgcggccg cctgctggcc ggcgcctacc      480
acgccgtggt gctgctggac gagcgcagcg ccgcgctgga cagcgccaag cgcgacggca      540 ccctggcccct ggccgccggg gcgctctgcc gcgaggcgcg cagcgcgcaa atcttttttgc    600
```

```
tcaaaggagg atatgaagct tttctgctt cctacccgga gctgtgcagc aaacagtcga      660
cccccatggg gctcagcctt ccctgagta ctagtgtccc tgacagcgct gaatcggggt      720
gcagttcctg cagcaccccg ctctacgatc agggtggccc agtagagatc ctgcccttc      780 tgtacctggg cagtgcctat catgcttccc gcaaggacat gctggatgcc ttgggcatca      840
ctgccttgat caacgtctct gcgaactgtc ccaaccattt cgagggtcac taccagtaca      900
agagcatccc cgtggaggac aaccacaagg cggacatcag ctcctggttc aatgaggcaa      960
ttgacttcat agactccatc aagaatgctg gtggaagggt gtttgtgcac tgccaggcgg     1020
gcatttcccg atcggccacc atctgcctcg cttacctcat gaggactaat cgagtcaagc     1080
tggatgaggc ctttgagttt gtgaagcaga ggagaagcat catctccccc aacttcagct     1140
tcatgggcca gctgctgcag tttgagtcga aggtcctggc cccccactgc tcggcagagg     1200
cggggagccc cgccatggct gtgcttgact gcagcacctc caccaccacc gtcttcaact     1260
tcccggtctc cattcccgtc caccccacaa acagtgcatt gagctacctt cagagcccta     1320
tcacgacctc tcccagctgc tgaaaagcca cgggaggcga tcttcacaac ccaccgggat     1380
tccaggctcc tggaaagtgg acatgcaata actccaggga aggggctcg tgagggctgg     1440 tccttatttta tttaatttca cccaagttcc actgggttcc tgagcagttg taatgatgac     1500
ttcacgccaa gatgtttgct gaactcagca cattccggga ccaacataca gtgggtacat     1560 caagtcccctt ggacagaaag gggcagaaga gagaggactc aagtgtgaga gccgatttct     1620
ttgttcttgt ccctgtttcc tgaagacact tttcatgctt gacataccta ccagtattac     1680
cattcccgac aacacgtaca catatgagaa tatactttgt tttatttatt tttgtgtagg     1740
cggttcacct tcacaaatgt cagtgtctac tcctagaaga accaaatacc tcaatttttg     1800
tgtttgagta ctgtaatgtc ctgtaaatat atcctaagca ggtttgtttt cagcactgga     1860
aagcaccagt gttgattttg ttttgttttt ttaagttgcc aacagttgta tgtttgctaa     1920
ttatttatga cctgaaataa tatatatctt cttctaagaa gacattttgt tacataagga     1980 tgacttttttt atacaacaga ataaattatg gcatttctat tgaaaaaaaa aaaaaaaaa     2040 aaaaaaaaaa aaaaaaaaa aaaaaaaaa aaaaaaaaa aaaaaaaaa aaaaaaaaa     2100 aaaaaaaaaa aaaaaaaaa aaaaaaaaa                                       2130

<210> SEQ ID NO 65
<211> LENGTH: 1150
<212> TYPE: DNA
<213> ORGANISM: Bos Taurus

<400> SEQUENCE: 65
attattgctc tgcaaactca gaacagcaac tgccaagact accctgagta gaggatggtc       60
ctgaacagag ctctgattct gggaaccctc gccctgacca ccatgatgag ccccagtgga      120
ggtgaagaca tcgtggctga ccatgttggc atctatggca taagcatata tcagtcttat      180
ggtccctctg gccagtacac ccatgaattt gatggagatg agcagttcta tgtggacctg      240
gagaagaagg agactgcctg gcagctgccc ctatttagca gaatgttaag ttttgaccca      300
cagttagcac tgagaaacat agctatcatg aaacttcatg tggacttcct gactaaattc      360
tccaactcta ctgctgctac caataaggtt cctgaggtga ctgtgttttc caagtctccc      420
gtgatgctgg gtcagcccaa cacctcatc tgtcatgtgg acaacatctt tccccctgtg      480
atcaacatca catggttgag gaacggacac tcggtcacag agggagtttc tgagaccagt      540
tttcttatca ggagtgatta ttctttcctc aagatcaaat atctcgcctt cctcccttct      600
```

```
gatgatgaca tttatgactg caaagtggag cactgggggcc tggatgagcc acttctgaaa     660
cactgggagc ctgagattcc agccctatg tcagagctga cagagactgt ggtctgtacc       720
ttggggttga ccatgggcct cgtgggcatt acggtgggca ccatcttcat catccaaggc     780
ctgcgctcag gtgacccttc agacaccag ggggcccttgt gagtcaccct ccagaagagc     840
agatgcactg cccatctatg tggatatgcc agaagactgg atatgccaga tgacctagaa     900 ctattttttgg gccaaattca tcatatacct tctctcctcc tacacttctc ctcccatttt    960
tttactctgg gagttaatat gctatatcat ctcacatacc ctcagaattc tctccctgac    1020
cttctagtac ttttttcttttt ttcaattatc acctaatatg ggatctctga gatatcccac 1080
tcagcagcct aattctccaa tggcctttag ctaatgtatc tatggaagca ataaatctct    1140
ttatgtggtc                                                            1150

<210> SEQ ID NO 66
<211> LENGTH: 719
<212> TYPE: DNA
<213> ORGANISM: Bos Taurus

<400> SEQUENCE: 66
agctgcctca acatgacctc ctgggctgtc ctgctcatca cctcggtgct cctggttgcc      60
ccagggctgg cttttttccgg tctgactcct gagagccacg accaggcgac ggcccatcta    120
tgtgatggag acgagttgtg ccagggcctg gccctggagg atccccaggg tgacctgctg    180
ctccaaggag aagagctgag cctacgctgt ggttcttgtc ggagaataat acaacatctg    240
atggacaagt tgggagatca gcccgatgag aataccgtta tcgaggaggc ctccaaggtg    300
tgcagcaaga tgaggctgct gaaaggtctg tgcaagtcaa tcatgaagaa attttctccgt   360 accatcgctg aggacatcgt agctggaaaa acctctcagg ttatctgtgt ggacatcaag    420
atgtgcaaaa gcaagccagt aggtttcatt tgattccctg ggtcctctta ccccatcctg    480
gggaaaaagc acagaaactc cagcatcctc ggccggctcc ttccttcctg aatccaggag    540
tcttctctcc agtttctctc accaaactcc ctccactgcc tttccctctc agaataaaat    600
atcatgcaag aaaaaaaaaa aaaaaaaaa aaaaaaaaaa aaaaaaaaaa aaaaaaaaaa      660 aaaaaaaaaaa aaaaaaaaaa aaaaaaaaaa aaaaaaaaaa aaaaaaaaaa aaaaaaaa     719

<210> SEQ ID NO 67
<211> LENGTH: 1431
<212> TYPE: DNA
<213> ORGANISM: Bos Taurus

<400> SEQUENCE: 67
gttatggggc cgcgaaccct cctcctgctg ctctcgggg tcctggtcct gaccgagacc       60
cgggctggct cccactccct gaggtatttc tacaccgccg tgtcccggcc cggcctcggg    120
gagccccgct tcatcattgt cggctacgtg gacgacacgc agttcgtgcg gttcgacagc    180
gacgccgggg atccgagagt ggagccgcgg gcgcggtggg tggagcagga ggggccggag    240
tattgggatc aggagacgcg aaaggccaag gaccacgcac aatttttccg actgggcctg    300
aacaccctgc gcggctacta caaccagagc gaggccgggt ctcacacccct ccagtggatg    360 tacgctgcg acgtggggcc ggacgggcgt ctcctccgcg ggttctggca gttcggctac    420
gaaggcagag attacatcgc cctgaacgag gacctgcgct cctggaccgc ggcggacacg   480
gcggctcaga tctccaaacg caagtgggag gcggcagatg ttgcggagag acagaggaac    540
tacctggagg gcacgtgcgt ggagtggctc cccagatacc tggagaacgg gaaggacacg    600
```

| | |
|---|---:|
| ctgctgcgcg cagaccctcc aaaggcacat gtgacccatc accccatctc tggtcgtgag | 660 |
| gtcaccctga ggtgctgggc cctgggcttc taccctgaag agatctcact gacctggcag | 720 |
| cgcaatgggg aggaccagac ccaggacatg gagcttgtgg agaccaggcc ttcaggggat | 780 |
| ggaaccttcc agaagtgggt ggccctggtg gtgccttctg gagaggagca gagatacacg | 840 |
| tgcagtgtgc agcatgaggg gcttcaggag ccccctcaccc tgagatggga acctcctcag | 900 |
| acctccttcc tcaccatggg catcattgtt ggtctggttc tccttgtcac tggagctgtg | 960 |
| gtggctggat tgtgatctg gatgaagaag cgctcaggtg aaaaggagg caattatatc | 1020 |
| caggcttcaa ggagtgacag tgcccagggc tctgatgtgt ctctcacggt tcctaaagtg | 1080 |
| tgagacacct gccttatggg gactgagtga tgcttcatcc cactatgtga cattagatcc | 1140 |
| ctggaccgct ctttctgcag ctgcatctga atgcgtctgt gctcctattc gcataacgta | 1200 |
| ggagttaggg agactggccc acccatgccc actgctgccc ttccccactg ccgtccctcc | 1260 |
| cgaccctgac ctgtgttctc ttccctgatc cactgtcctg ttccagcaga aatgaggctg | 1320 |
| gaccatgtct atccctgtct ttgctttata tacactgaat aatgatatct tatttcttta | 1380 |
| ttgaaaataa aatctgtata tatgaaaaaa aaaaaaaaaa aaaaaaaaa a | 1431 |

<210> SEQ ID NO 68
<211> LENGTH: 558
<212> TYPE: DNA
<213> ORGANISM: Bos Taurus

<400> SEQUENCE: 68

| | |
|---|---:|
| gtcacctaag gagtcaagtt ctttacctct cagatattcc tagaccatcc atgatttcaa | 60 |
| gatatttctc tttgttaagt attcctggtt gacctaaatg ccttcctgac tttctaacca | 120 |
| cctcctctgt ctgaattgtg caacagtgaa ttaaatgtgc tttccaaaaa gaattggcct | 180 |
| aaggctcctc agggcttcct gtgctgttat ttctgtttcc tttgggtgaa taaagtgaca | 240 |
| ttgcctcaca aatgattatt ttagagcaaa catgtttcca aatgtaacag aatgatgatg | 300 |
| actccaggaa ctgaagttag tttccgaatc tagagctttt gtttagatgt gaatcacatt | 360 |
| ttcaaaatga gtaggttttt actggtctaa gagagttttt tggttttggg gttttttttgg | 420 |
| ggggattttt ttttttttaat tggggatttc ttaaaacctt gtataacttc aacagaaggg | 480 |
| actgtcaatt taggttttgt ttgctggagg cataaattag taaagtaaag gcttaatggc | 540 |
| aaattattta caggacca | 558 |

<210> SEQ ID NO 69
<211> LENGTH: 1745
<212> TYPE: DNA
<213> ORGANISM: Bos Taurus

<400> SEQUENCE: 69

| | |
|---|---:|
| gacacttctg caaactgctc agccctaagg caccgagcgc ctgaacccag aaggcgagcc | 60 |
| ggagccggag gagcccagcc gccaggccgt tcgaccgctg ccctcgacac catggatctg | 120 |
| catctcttgg actactcaga gccgggggaac ttctctgaca tcagctggcc ctgcaatggc | 180 |
| agtgactgca tcgcagtgga caccctgcag tgcggccaca tacccaacaa aagcgtcctg | 240 |
| ctatacacgc tgtccttcgt ctacatcttc atctttgtga tcggcatgat cgccaactcc | 300 |
| gtggtggtct gggtgaacat ccaggccaag actacgggct acgacacgca ctgctacatc | 360 |
| ttgaacctgg ccattgccga cctgtgggtg gtggtcacca tccctgtctg ggtggtcagc | 420 |
| ctcgtgcagc ataaccagtg gcccatgggc gagctcacgt gcaaggtcac ccacctcatc | 480 |

```
ttctccatca acctcttcgg cagcatcttc ttcctcacct gcatgagtgt ggatcgctac      540
ctgtccgtcg cctacttcgc cagcacctcc ggccgtaaga gaggctggt gcgccgtgcc       600
gtgtgcgtcc tggtgtggct gctggccttc ggcgtgtccc tgcccgacac ctactacctg     660
aagaccgtga cgtccgcttc caacaacgag acctactgcc gggctttcta ccccgagcac    720
agcgtcaagg agtggctcat cagcatggag ctggtctccg tgatcctggg cttcgccatt    780
cctttctgca tcatcgctgt cttctacttc ctgctggccc gcgccatcgc ctcctccagc    840
gaccaggaga agcagagcag ccggaagatc atcctctcct acgtggtggt cttcctggtg    900
tgctggctgc cgtaccacct ggtggtgctg ctggacatct tctccatcct gcactacatc    960
cccttcacct gccagctgga ggccttcctc ttcacggcgc tgcacgtcac gcagtgcctg   1020
tcgctggtgc actgctgtgt caaccctgtg ctctacagct tcatcaaccg caactaccgg   1080
tacgagctga tgaaggcctt catcttcaag tactcggcca agacgggcct caccaagctc   1140
atcgatgcct cccacgtttc ggagaccgag tactccgctt tggagcagaa tgccaagtga   1200
tgttgccccg cgcggcctct ggacctgtgc gctgggctgc agcggggcga cctgctaggc   1260
tgcctggttt tccggaggaa agccaagtgg cttcgggctt ggcgaccctc gttggcgtgg   1320
agaggggcag cctgcgtccc tatggctcct ttcttgctct cggcccagcg tgaccctcgc   1380
ggggcccctg tgacaagccc ccgctgctcg tcacaccagc ttcgggacag gcttgccagc   1440
acttctgtaa catacgactt ttctgtgctg cctaaaggtt tcataatggg gatttgtatt   1500
taaatcttaa gactctattt ttctctcttg atgtaccctc tcagtgtatt tgaaagttta   1560
tattttaaat atcgtatggg aggtatccat gctgacatgt actcagcgtc gtagttctga   1620
ggttagtttg acttccgttt tgactaagga tgacattaat tgttagctgt tttgaaagcc   1680
tctctctata tatatatata tatatatata tatattaaaa tatatatgcc aaaaaaaaaa   1740
aaaaa                                                                1745
```

<210> SEQ ID NO 70
<211> LENGTH: 2538
<212> TYPE: DNA
<213> ORGANISM: Bos Taurus

<400> SEQUENCE: 70

```
ggcagcaagt ggtttgctct cagggcagca ggaggaaatc gcccctgtct gataagacac       60
cagttcaaga aaggacgcat gctgtctctc aggagtttgg ctgatttcca gatatgacca      120
tgtatctgtg gcttaaactt ctggcattcg gctttgcctt cctggacatc gcagtgtttg      180
ttgcaggaaa ctctacccaa ccttctactc aagatgagca gaccacgacc cccgcactga      240
ccactgcatc cagcgttagc cctgcaaccg ctctctcaac catagctcct actaagccac      300
catgtgagaa caaatacgga ggtgtgtctg tgaagtactc tttcaacgat aataagacat      360
ttactgcaac actcgatgtt aagcgagagg aatgtgaacc tcctggatgt gaaaaggagc      420
accgtggcct gtctgcatgt caaactaaga atatcagtat gtcacaccct tcgtgtgagc      480
ctccatttga atatgtcttg gaggtaccac cagatcctaa tcagtttcag ctggtagact      540
gcgtggaaga tgaagaagca aatacttccc tttgtttaca ctggcaaaac aaagattttc      600
cagataatgg acaattcaag tgtaatgaaa ataaaattga atacaaattt aaatgtgatg      660
gcggttctcc aagttataat aaagacacat ttaaagtgag gaatcttaaa cccagaacta      720
attatacttg tagttcacaa gtactctatg atcaacagct tcttattagt caaaataaaa      780
ctattgaaac agattttgga gaaccagaag caccctcagaa ttttacttgt tctgctaaaa     840
```

```
atgcaactga aggaaagtgt acctggacac cacctcaaag ctatttgac agaatctctc    900
tttgctattg gattactcca ggaggacgaa attgcatccc tcaggataaa acccaggacg    960
gaatagattt gcacaatttg agacctttca caaactatac ggtggtgtta caagcccggg   1020
tcacaggaaa agtaactcgc agtagaaatg cgacctatac attttggaca gatccagcaa   1080
agccaagcaa ggtcaatggt ttaagtgctt cacggaagac agaaaatact atagctgtga   1140
gctgtaaacg tcctgaccag cttaatggcc ccgaagggaa gtactatttg gaagtaagaa   1200
ctggaaatac cttggttaaa aaagattcag gaccagaatg cagattcttg gtagaagatc   1260
ttcagtattt aacagaatat aatttttttgg tctattatga caatacaaaa tttgctggtc   1320
ttccagagag tgttacagca tcaacatctt ataatgctaa agcactcatc atattttttgg   1380
tatttctgat tattgtgaca tcaatagccc tgctcattgt tctctataaa atctatgatc   1440
tgcataagaa aagatccagc aatttagatg agcagcagga actcgttgaa agggatgatg   1500
agaagcagct gatgaacgtg gagcccattc atgcagatgt tttgctggag acttacaagc   1560
ggaagatggc tgacgagggg aggctcttcc tggctgaatt tcagagcatt ccacgggtat   1620
tcagcaagtt ttccatcaag gatgctcgaa aatcctttaa ccagaacaaa aatcgctatg   1680
ttgatatcct tccttatgac tacaaccgtg ttgaactctc tgacataaac ggagatgcag   1740
gatcaaaacta tataaatgcc agctatattg atggtttcaa agagcccagg aagtacatcg   1800
cagcacaagg tcccagggat gagactgttg atgatttctg gaggatgatc tgggagcaga   1860
aagccacggt tattgtcatg gtcactcgat gtgaggaagg gaacaagaac aagtgtgcag   1920
agtactggcc gtcaatggac gagggcagcc gggtttatgg agatgtgatt gtggagatca   1980
acgagcacaa aagatgccca gattacatca ttcagaagct gactgttgga aacagaaaag   2040
aaaaggcaag tggaagagca gtaactcaca ttcagttcac cagctggccg gaccacgggg   2100
tccccgaaga ccctcacctg ctgctcaagc tgcgcaggag ggtaaacgct ttcagcaact   2160
tcttcagcgg ccccatcgtg gtgcattgca gtgctggcgt tgggcgcaca ggcacctaca   2220
tcggcatcga cgccatgctg gaaggcctgg aggcagagaa caaggtggac gtctacggct   2280
acgtcgtcaa gctccggcga cagaggtgcc tgatggtgca ggtggaggca cagtacatct   2340
tgattcacca ggccttggtg gagtacaatc agtttggaga gacagaagtg agcctgtctg   2400
agctacaccc gtacctgtct aacatgaaga aaagagaccc gcccagtgag ccctccccac   2460
tggaggctga gttccagaga cttccttctt ataggagctg gaggacacag catattggga   2520
accaaaaaaa aaaaaaaa                                                2538

<210> SEQ ID NO 71
<211> LENGTH: 2080
<212> TYPE: DNA
<213> ORGANISM: Bos Taurus

<400> SEQUENCE: 71
ggagccgaag ctgtgtctgg gcagccgggc taggccagga agaccatgtg aatgggccca     60
gggggctcct gggctgggca gggaccatgg gctgtagctg cagctcaaac ccagaagatg    120
actggatgga aaacatcgat gtatgtgaaa actgccacta ccccatagtc ccactggatg    180
gcaagaccac gctgcccatg cggaatggct ctgaagtgcg tgatccactg gtcacctacg    240
agggatccaa ccccccagct tctccactgc aagacaacct ggttatcgcc ctgcacagct    300
atgagccttc tcacgacgga gacctgggct tcgagaaggg tgaacagctc cgtatcctgg    360
agcagaacgg cgagtggtgg aaggcgcagt ccctgaccac gggccaggaa ggtttcatcc    420
```

```
ccttcaactt tgtggccaaa gcgaacagcc tggagcccga accctggttc ttcaagactc      480
tgagccgcaa ggacgcggag aggcagctcc tggcgccggg gaacacgcac ggctccttcc      540
tgatccggga gagcgagagc acggcgggat cattttcact gtcggtccgg gacttcgacc      600
agacccaggg agaagtggtg aaacattaca agatccgtaa cctggacaaa ggcggcttct      660
acatctcgcc ccgcgtcact tttcccggct tgcacgagct ggtccgccat tacatgaata      720
cttcggacgg gctgtgcaca cggttgagcc gcccctgcca gacccagaag ccccagaagc      780
cttggtggga ggatgagtgg gaggttccca gggagactct gaagctggtg gagcggctgg      840
gggctggcca gttcggagag gtgtggatgg ggtactacaa cggcacacg aaggtggcag       900 tcaagagcct gaagcagggc agcatgtccc ccgatgcctt cctggccgag gccaacctca      960
tgaagcagct gcaacaccag aggctggtcc ggctctacgc ggtggtcacc caggagccca     1020
tctacatcat cacggaatat atggagaacg aagcctggt ggattttctc aagacctccg      1080
aaggcatcaa gctgactatc aacaaactct ggacatggc agcccaaatt gcagagggca      1140
tggcattcat tgaagagcag aattatatcc accgtgactt gagggctgcc aacatcctgg     1200
tgtcccatag cctgagctgc aagattgcgg actttggtct agcacgcctc attgaggaca     1260
acgagtacac agccagggag ggtgccaagt tcccattaa gtggacagca ccagaagcca      1320
ttaactatgg gacattcacc atcaagtcgg acgtgtggtc ttttgggatc ctgctgacgg     1380
agattgtcac tcatggtcgc atcccttacc cagggatgac caatcctgag gtgattcaga     1440
acctggagcg aggctaccgc atggtacgac ctgacaactg cccggaggag ttgtaccagc     1500
ttatgatgct gtgctggaag gagcgcccgg aagaacggcc cacctttgac tacctgcgca     1560
gcgtgttgga ggacttcttc acagccacgg agggccagta ccagcccag ccctgagggg      1620 cctaggtgac gggggcttgc agcccccac cacctagcca acctggctgg ggggtgcagt      1680
tcctgggtca tacccatgtg gcctgtgcac attcggactc agcatgtgaa gcccgcccac     1740
gtgcgacacg tacacttctc gtgtcttgta cacaggatct gtagttgggt gggctcatgt     1800
gtcttgtaca tgtgtggcct gtgcatatac gtcttggaca cttgtccaag ttgtcctttc     1860
tgggcgcccc cctgacttcc aagaccacca agagaggag agaggccat gattaacacc      1920 tgcttctccc tgtccccttt cctttcccc tggtcatcaa gatgctcttt gagagctggg      1980
accttatcta aaatacctct gtgtgctcct ctttggtgtt ggcacacata aggagctcaa     2040
taaatacctg ttggcgaaga ttgcaaaaaa aaaaaaaaa                            2080

<210> SEQ ID NO 72
<211> LENGTH: 707
<212> TYPE: DNA
<213> ORGANISM: Bos Taurus

<400> SEQUENCE: 72
tttttgttgt tttcccttgt gatataatac tttatgtaac aatgtaaata attatccagg       60
aataaaaagt aaacaaataa taaaactaaa ataccagcaa acagtgcacc ttgggaagcc      120
acagaacagc actattgatg ttacttttct tcatttgctc attcatttga aaagttaaaa      180
aacaattttt gcttttaat ggtgttaaag tcagtaatac agtttatgaa ctaaaataca      240
catttaccaa ataaaagact atatcacatg gtttgcaagc cttcacagct ttaaattcta      300
aagacaaaaa tctctaagtg gctgcacaaa atgacaaaat ggaggtaatt caagtttgtg      360 tcttatctt tacaattgct gcgctctcct tgtctgctgt caatctttgc aggaagatac      420
agtctggcag ggcttgggag ccctcaaaca attccaaacg atgacagatt tactctccaa      480
```

```
acaaacacag agctgagagt ttgtgtgtct ggggatgact gtaaaactgg ggattctctc    540
aactaccttg caggtagaat gcaaagttca tgaaataata tgcgaacatg aagctcacac    600
ataaatcatt acaactccat aagcggttaa aatcagagtg aggtctatac ctaagttaat    660
aatcccaaca tcaatttcct ggtttcaacg atgcacccac atcaccc                  707
```

```
<210> SEQ ID NO 73
<211> LENGTH: 1736
<212> TYPE: DNA
<213> ORGANISM: Bos Taurus

<400> SEQUENCE: 73
ctaaaaagcc atcgtcctcc acttcctgag gaggcagcag cagaacaaag ccagcagaga     60
ctcctttcct cttcttcatc cagtcacagc tgcctcagcc tctgctccgg gcaccatcct    120
ggggaaggac aagatgaagt ggacagcaca tgttattgtg gccatcttgc aggcacagtt    180
cccaattaca gcggcacaga gcttcggtct gctcgatcct aaactctgct acctgctgga    240
tgggatcctc ttcatctacg gcgttattgt cactgccctg tttctgagag caaagttcag    300
caggagtgcc aacgccccg cctaccagca gggccagaac ccggtctaca acagagctgaa   360 tgtcggccga agagaggagt atgcggtcct ggataggaga gggggcttcg accctgagaa    420 ggggggaaa ccgcagagga agaagaaccc caacgaagtc gtgtataatg agctaagaaa     480
agacaagatg gcggaggcct acagtgagat cggcatgaag agtgacaacc agcggcgaag    540
aggcaagggg catgatggtc tttaccaggg actcagcaca gccaccaagg acacctatga    600
cgccctccac atgcaagccc tgccccctcg ctaacagctc caggaggttt agacactcac    660
aggccagacc tgtagacgcc cagattgtta aagatacagg ataaagcatt tacaacctag    720
ttcactcaca tttctccacc acccaagtat ttctctttat gaatgggatg cttcaagatg    780
gtcatacatt tggtcatacc cagttccaaa ctcacacaga attttgtcct tggacgccgt    840
gagagtgtgc atccccatgc gcttcctgaa gagtccactg tgaacgcggc atgttctgag    900
gttttctggt ttcctgggga ctggcaggcc ctactccctg cagctccagg ctcttacctg    960
ggagtcgggc ctcctccttc tcaaacacaa ctgaattcag ggtgttttgt aagggtccca   1020
gagaaaccac aaatgttagt gcatgtccta acagcctgta ctgttctgtc cgttttttgag  1080 tagctttgct cttgctgtaa atttggcttc agttgttacc ctaccccta atttcaaggc    1140 aactggtgat tgggcccaga agcgggcaga ggggaaggtg gggtaggtag cggttggtac    1200
tggtaggtca gggaagggag caggggagcc agaggcctgg ggaggggcat gaaggagccc    1260
tcctgcaatc aagtgtacat tccccatggc agaacttgta tgccagggcc tcttttggga    1320
ccgagagatg agaaagccta gccttgtcct cgagcagccc atactctcac agggaagcca    1380
gctgtgaaga gtctgggatg gaagaacata gcggtgtcat tgcagatggt gaacgagtga    1440
gccggcagcg agagaagcaa gaccacattc tttgcagcca cttgctcacc tcatggaatg    1500
agacaaaccc atcatgggga aggccttgaa ggatgacttg gtatagcttg aacctagaaa    1560
gatcccaaag gacagtggca tcacaaaaag agcctcagct gacttgttgg aacagggctg    1620
tgtaatacaa gggcacatgg ccatggatgg aaacccactc tgctcggtct taatttatac    1680
tggtttgcta gagccttact cttttgcata ataaatacct ttagtgaaaa aaaaaa        1736
```

```
<210> SEQ ID NO 74
<211> LENGTH: 589
<212> TYPE: DNA
<213> ORGANISM: Bos Taurus
<220> FEATURE:
```

<221> NAME/KEY: misc_feature
<222> LOCATION: 502, 547
<223> OTHER INFORMATION: n = a, c, t, or g

<400> SEQUENCE: 74

| | | | | | |
|---|---|---|---|---|---|
| ccacgcgtcc | gctgcgggag | tggtatatga | tcatctctcg | agagatgttt | aaccctatgt | 60 |
| atgccttgtt | ccgtacctca | cctggtgatc | gggtcacata | caccatcaat | ccatcttctc | 120 |
| actgcaaccc | caaccacctc | agctacttca | gtttgttgg | acgcatcgtg | gccaaagctg | 180 |
| tgtatgacaa | ccgcctcctg | gagtgctact | ttactaggtc | cttctacaaa | cacattttgg | 240 |
| gcaagtctgt | cagatataca | gatatggaga | gtgaagacta | ccacttttac | cagggcctgg | 300 |
| tttatctgct | ggaaaatgat | gtctccacac | taggctatga | tctcactttc | agcactgagg | 360 |
| tccaagagtt | tggagtctgt | gaagttcgtg | acctcaaacc | caatgggggc | aacatcttgg | 420 |
| taacagagga | aaataagaag | gaatatgtac | acctggtgtg | ccagatgaga | atgacaggag | 480 |
| ccatccgcaa | acagctggcg | gntttcttag | aaggtttcta | tgagatcatt | ccaaagcgcc | 540 |
| tcatttncat | cttcactgag | caggagttag | agctgttata | tcaggactg | | 589 |

<210> SEQ ID NO 75
<211> LENGTH: 778
<212> TYPE: DNA
<213> ORGANISM: Bos Taurus

<400> SEQUENCE: 75

| | | | | | |
|---|---|---|---|---|---|
| cctttgaatt | tgatagtata | tttattagag | taagagatta | ggcttgttaa | acatctggat | 60 |
| taaaatggta | aaaggatttt | catacagttg | ttaggcacta | tacacactgt | tgtttacaat | 120 |
| agcatcagta | cttggtgaaa | ggtaaatctc | attcatttta | atgccttgat | ccatttgtaa | 180 |
| cattcagagc | aactccacca | ttttagaaac | actaatccaa | acttaaagag | acatagcact | 240 |
| aaatatccac | acggtagatt | taaaaataaa | tacagaaata | caaccagaag | tctacaaatc | 300 |
| atcacagtag | acagactggt | gaagccccag | ctatcatggc | agtgaagggc | tctggctaga | 360 |
| ttttgatgaa | aatttgctga | attctacacc | aaaagcaaga | acataataaa | ataacatgat | 420 |
| acacactttc | tgatgctcat | ttttatagca | gcaaagcatg | cttcacatgc | actgcctgtg | 480 |
| aaggatctta | caaggctcct | tcctactcag | ttagaaggta | tgcctggcaa | gaatgaagta | 540 |
| ccaccaagtg | tcaaagaatc | ccgaaaatag | aggcgaccag | ccagttcatg | gtgtgggaaa | 600 |
| gcagtgcagt | tttcagtaag | aatgactacc | cacagtcacc | agagtttcac | tgtaattcta | 660 |
| cattgcacat | gtcttcatca | tcaatataca | caaaaatagc | cccaagcaca | aagccaatcc | 720 |
| acttagggga | ataacaatag | taataagagt | aaagatgata | atattgaaaa | tgacacaa | 778 |

<210> SEQ ID NO 76
<211> LENGTH: 1272
<212> TYPE: DNA
<213> ORGANISM: Bos Taurus

<400> SEQUENCE: 76

| | | | | | |
|---|---|---|---|---|---|
| ggcgtccccg | gctctcccga | gcggcggcct | ccccgctcct | ttccggccag | cggaggcagc | 60 |
| ttgcggcggc | cggtccccg | gaggcgcggc | gtcggccgag | cggcggcgcg | gagcgtcgag | 120 |
| cgcagcgcgg | cggcggcggc | ggcccggcag | ccaacatggc | ggcggcggcg | gcggcgggcg | 180 |
| cgggcccgga | gatggtccgc | gggcaggtgt | tcgacgtggg | gccgcgctac | accaatctct | 240 |
| cgtacatcgg | cgagggcgcc | tacggcatgg | tgtgctctgc | ttatgacaat | gtcaacaaag | 300 |
| tccgagtcgc | catcaagaaa | atcagccctt | ttgagcacca | gacgtactgc | cagagaacgc | 360 |

```
                                          -continued
tgagagagat aaagatctta ctgcgcttca gacatgagaa catcatcgga atcaatgaca       420
ttattcgagc accgaccatc gagcagatga aagatgtgta tatagtacag gacctcatgg       480
aaacagatct ctacaagctc ttgaagacgc aacacctcag caacgaccac atctgctatt       540
ttctctacca gatcctcaga gggttaaagt atattcattc agccaacgtg ctgcaccgtg       600
acctcaaacc ttccaacctg ctgctcaaca ccacctgcga tctcaagatc tgtgactttg       660
gcttggcccg tgttgcagat ccagaccacg accacacagg gttcttgaca gagtacgtgg       720
ccactcgctg gtaccgggct ccagaaatca tgttgaattc caagggctac accaagtcca       780
tcgacatctg gtccgtcggc tgcatcctcg cggagatgct ctccaacagg cccatcttcc       840
ccgggaagca ctaccttgac cagctgaacc acattctggg tattcttgga tccccgtcgc       900
aggaagacct gaattgtata ataaatttaa aagctagaaa ctacctgctc tctcttccac       960
acaaaaataa ggtgccatgg aacaggctgt tcccgaacgc ggactccaaa gctctggatc      1020
tactggacaa aatgttgacg ttcaaccctc acaagaggat cgaggtggag caggctctgg      1080
cccatcctta cctggagcag tactacgacc cgagcgatga gcccgtcgcc gaagcaccct      1140
tcaagtttga catggaattg gatgacttgc ccaaggaaaa gctcaaagaa ctcattttg       1200 aagagactgc tcgattccag ccgggatacc gatcttaaat ttgtcaggac acgggctcag      1260
agcacggcac gc                                                          1272
```

MARKERS FOR VIRAL INFECTIONS AND OTHER INFLAMMATORY RESPONSES

PRIORITY CLAIM

This application is a continuation-in-part application of U.S. patent application Ser. No. 11/622,124, filed Jan. 11, 2007, now abandoned, which claims priority under 35 U.S.C. §119(e) to U.S. Provisional Patent Application 60/757,965, filed Jan. 11, 2006. This application also claims priority under 35 U.S.C. §119(e) to U.S. Provisional Patent Application 61/014,172, filed Dec. 17, 2007. The foregoing applications are incorporated by reference herein.

GOVERNMENT RIGHTS

Pursuant to 35 U.S.C. §202(c) it is acknowledged that the U.S. Government has certain rights in the invention described, which was made in part with funds from the USDA/CSREES, grant numbers 2004-35204-14916, 2004-35204-17005, and 2008-35204-04652.

FIELD OF THE INVENTION

This invention relates to the field of molecular biology and virology. More specifically, the present invention provides materials and methods for the diagnosis and staging of bovine viral diarrhea virus (BVDV) and other infections where maternal blood immune cell gene expression and blood proteins are differentially expressed in the mother when carrying virally infected fetuses.

BACKGROUND OF THE INVENTION

Several publications and patent documents are cited throughout this application in order to more fully describe the state of the art to which this invention pertains. The disclosure of each of these citations is incorporated by reference herein.

Bovine viral diarrhea virus (BVDV) costs the United States cattle industry more than 400 million dollars per year. The pathogenesis of BVDV infection has features that are unique to this virus and vary with the time of infection, virulence of the viral strain, and age of the animals at the time of infection.

When the infection occurs after 150 days of gestation (post-development of the fetal immune system) or after birth, including adult animals, the infection is referred to as acute infection. The clinical manifestation of acute BVDV infection ranges from sub-clinical or unapparent infections to embryonic death, abortions, increased incidence of stillborn calves, malformed or slow growing calves.

Certain strains of BVDV can cause a hemorrhagic syndrome with high morbidity and moderate mortality in adult animals. Acutely infected animals usually recover and eliminate the virus within 10 to 14 days post infection.

Animals vaccinated with modified live vaccines against BVDV have an immune response similar to the one induced by natural, acute infection. In contrast, infection of the fetus during the first 150 days of gestation, when the fetal immune system has not yet developed, can lead to the generation of persistently infected (PI) calves. Some of these PI calves die soon after birth, but others live for relatively long periods of time without showing any clinical signs. PI animals cannot eliminate the infecting BVDV from their system, and continuously release high amounts of virus in their bodily secretions and excretions, making them a continuous source of infection within the herd and potentially to other herds as well. Furthermore, nursing PI calves can acutely infect their mothers through nasal-respiratory transmission and other normal nursing calves, which, if not vaccinated, in turn infect their own mothers while they are pregnant, producing a new cycle of infection and eventually more PI calves.

Mucosal disease, a fatal complication observed in PI calves, occurs when the virus mutates or the animal is superinfected with an antigenically related BVDV virus. Current vaccines are relatively inefficient in preventing fetal infections, therefore the identification and elimination of PI animals is essential to any successful program for control or eradication of BVDV.

Currently available tests for the detection of PI animals are based on the identification of the viral antigen in a blood or tissue sample (most commonly a skin biopsy) using detection methods that depend on the specific binding of anti-BVDV antibodies. Although these tests are widely used for the detection of PI animals they frequently fail to identify all infected animals (false negatives) resulting in the failure to remove all PI animals from the infected herd. Moreover, serological tests cannot differentiate between PIs and uninfected animals, or between acutely infected and vaccinated animals.

Identification and elimination of PI animals from an infected herd is the most cost effective measure to control and eradicate BVDV, underscoring the criticality of an inexpensive and convenient diagnostic test. The present invention provides such a test and kit for performing the same.

SUMMARY OF THE INVENTION

In accordance with the present invention, methods and compositions for diagnosis of Bovine Viral Diarrhea Virus (BVDV) are disclosed. Specifically, a simple, convenient test for accurately diagnosing BVDV is provided. The instant method provides the means to differentiate cattle persistently infected with BVDV (PI) from control non-infected steers. Other markers are provided which enable the skilled person to identify 1) heifers carrying persistently infected fetuses; 2) heifers carrying transiently virally infected fetuses and 3) heifers carrying control, uninfected fetuses. Such differentiation may be accomplished by detecting altered expression levels of one or more markers shown in Tables 1-9, or the proteins or peptide fragments encoded thereby. Most preferably, the test can be easily conducted in the field by veterinarians or cattle producers.

In one aspect of the invention, BVDV surrogate markers are provided. A BVDV surrogate marker may be a nucleic acid or polypeptide or fragments thereof. Such markers are provided herein at Tables 1-9. Also provided in accordance with the invention are oligonucleotides, including probes and primers, that specifically hybridize with the nucleic acid sequences set forth in Tables 1-9. Antibodies immunologically specific for the BVDV marker polypeptides described herein are also within the scope of the invention.

In a further aspect of the invention, recombinant DNA molecules comprising the nucleic acid molecules set forth above, operably linked to a vector are provided. The invention also encompasses host cells comprising a vector encoding a BVDV specific marker of the invention.

In another aspect of the invention, methods for detecting a differentially expressed BVDV specific marker molecules in a biological sample are provided. Such molecules can be BVDV specific marker nucleic acids, such as mRNA, DNA, cDNA, or BVDV specific marker polypeptides or fragments thereof. Preferably the BVDV surrogate marker exhibits expression levels which differ at least 2 fold from normal, uninfected cattle. The BVDV markers of the invention may be up or down regulated relative to the levels observed in non-infected control cattle. Exemplary methods comprise detection of isolated biological molecules which hybridize to BVDV specific markers which are affixed to a solid support, or mRNA analysis, for example by RT-PCR. Immunological methods include for example contacting a sample with a detectably labeled antibody immunologically specific for a BVDV specific marker polypeptide and determining the presence of the polypeptide as a function of the amount of detectably labeled antibody bound by the sample relative to control cells. In a preferred embodiment, these assays may be used to detect differentially expressed proteins encoded by the nucleic acids set forth in Tables 1-9.

In a further aspect of the invention, kits for detection of BVDV infection or lack thereof are provided. An exemplary kit comprises a BVDV specific marker protein, polynucleotide or a gene chip comprising a plurality of such polynucleotides, or antibody, which are optionally linked to a detectable label. The kits may also include solid supports, pharmaceutically acceptable carriers and/or excipients, a suitable container, and instructions for use.

In yet another aspect of the invention, the differentially regulated BVDV markers described herein may be used in screening methods to identify new therapeutic agents for the treatment of viral infections, including BVDV infection. Agents which affect the differential expression of nucleic acids or proteins associated with BVDV infection may prove efficacious for the treatment of BVDV.

In another aspect of the invention differentially expressed markers for BVDV detection are provided in Table 12. Also included are methods for diagnosing BVDV in a persistently infected ruminant test animals. An exemplary method entails obtaining a biological sample from a test animal and from a control animal seronegative for BVDV; contacting said sample with an agent having affinity for at least one differentially expressed marker shown in Table 12; and diagnosing the presence of BVDV via detection of at least one differentially expressed BVDV marker, wherein an alteration in the expression level of said BVDV marker obtained from said test animal relative to that obtained from said seronegative control animal indicates said test animal is persistently infected with BVDV.

In yet another aspect of the invention, a solid support for diagnosing BVDV in a persistently infected ruminant test animal is provided, said solid support comprising a substrate having a plurality of addresses, each address having disposed thereon a set of one or more biomolecules, each biomolecule at a given address specifically detecting a chemokine, wherein said support comprises sufficient addresses to detect at least CXCL4, CXCR4, CXCR7, G-protein, CD45, LCK, ZAP-70, CD3-zeta, CBL, MEK1/2 and ERK1/2.

Additionally, in a different aspect of the invention, a kit is provided for diagnosing persistent BVDV infection, comprising at least one BVDV marker detector molecule, and reagents for detection of the same, said method optionally comprising a solid support comprising a plurality of BVDV nucleic acid markers selected from the group consisting of CXCL4 (NM_001101062), CXCR4 (NM_174301) and CXCR7 (NM_001098381), or a solid support comprising a plurality of BVDV polypeptide markers selected from the group consisting of polypeptides encoded by CXCL4 (NM_001101062), CXCR4 (NM_174301) and CXCR7 (N_001098381).

In a further aspect of the invention, a method is provided for identifying agents useful for the treatment of persistent viral infections, comprising: providing a host cell expressing at least one BVDV marker in Table 12 which is differentially expressed in response to persistent BVDV infection, exposing said cell to an RNA virus under conditions suitable for infection to occur; incubating said host cells in the presence and absence of said agent; and identifying those agents which modulate the expression of at least one BVDV marker in cells treated with said agent when compared to untreated cells, thereby identifying agents which inhibit infection with BVDV. Agents which affect the differential expression of nucleic acids or proteins associated with BVDV infection listed in Table 12 having efficacy for the treatment of BVDV are also encompassed by the invention.

BRIEF DESCRIPTION OF THE FIGURES

FIG. 1 is a schematic diagram showing some of the features of persistent and acute or transient BVDV infection.

FIG. 7 shows a schematic of CXCL4/CXCR4 and TCR pathways (A) and relative expression of differentially expressed genes (B) in blood of pregnant heifers carrying control or PI fetuses. A—Stars show differentially expressed genes on microarray screen, completed on day 160 of gestation. Arrows show direction of the change in gene expression, number shows the ratio of mRNA amount in blood of heifers of the PI group when compared with the blood of heifers of the control group for the genes tested with microarray and qRT-PCR (microarray data, day 160, P<0.01). Circled—P shows dephosphorylation. B—Relative expression of mRNA for differentially expressed genes of CXCL4/CXCR4 pathways in blood of heifers carrying PI or control fetuses, detected with qRT-PCR on day 160 of gestation. Data are presented as mean±SE. —P<0.01, *—P<0.001.

DETAILED DESCRIPTION OF THE INVENTION

Figure 2:
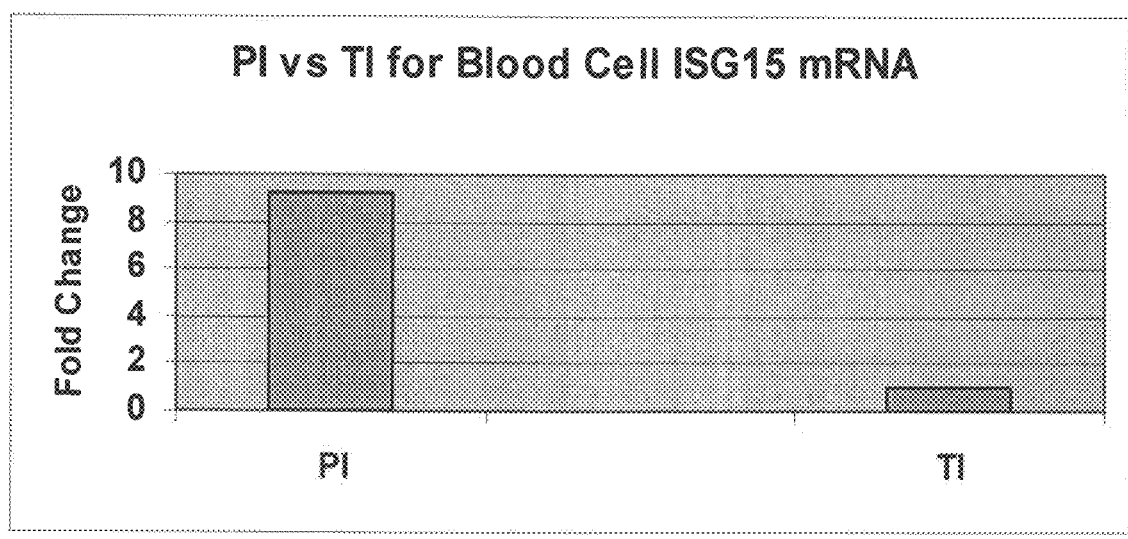
FIG. 2 is a graph showing upregulation of interferon stimulated gene 15 (ISG15) in blood from persistently infected calves. ISG15 mRNA levels were determined using semi-quantitative (adjusted for GAPDH) Sybr green Real Time PCR. Blood from three persistently infected (PI) and three calves that had been vaccinated against BVDV (TI) are represented in the analysis. ISG15 means differ between PI and TI (P<0.05).

Bovine viral diarrhea virus (BVDV) provides a challenge to cattle producers, because BVDV is a contagious and potentially lethal disease that is currently difficult and expensive to differentially diagnose. Current tests are performed on samples collected from young calves after birth. Thus, many of these infected calves have already shed virus and have infected other pregnant cows. Therefore re-infection of pregnant cows helps maintain the infectious cycle.

The complex host-viral interactions resulting from persistent infection are minimally understood, particularly in the bovine host. Thus, one purpose of the present research was to identify those genes and associated biological pathways which are activated or down-regulated in response to viral infection to facilitate a better understanding of the mechanism of virus action. Another objective of the research was to identify peripheral blood markers that will help distinguish pregnant cattle that are carrying persistently infected from those carrying transiently virally infected fetuses. Depending on the time of infection during gestation, noncytopathic (ncp) bovine viral diarrhea virus (BVDV) causes persistent infection (PI, <150 d) or transient infection (TI, >150 d.) in fetuses. TI fetuses develop immunity to the viral strain and clear the virus. PI fetuses do not recognize the virus as a foreign agent and once born continually shed the virus and infect other cattle. Detection and removal of pregnant cows or heifers carrying PI fetuses would greatly benefit the successful implementation of control programs. Provided herein is a simple and effective test for diagnosing BVDV, and identifying persistently infected (PI) animals.

Experimental evidence is provided which indicates that the pattern of gene expression in vaccinated or acutely infected and PI animals is different, and therefore the differential expression of genes can be used as a diagnostic marker for these types of BVDV infection. Genes that are differentially expressed in the cells of the blood or the skin of persistently infected animals (surrogate markers) are identified using gene chip analysis of mRNA of PI when compared to vaccinated or acutely infected animals. Antibodies produced against such surrogate markers can be used to develop a diagnostic test to detect PI animals, by analyzing the presence of the surrogate marker in an animal's blood or skin.

Thus, in accordance with the present invention, gene chip analysis has been performed on nucleic acids obtained from blood cells collected from bovines that are persistently infected with BVDV when compared to vaccinated control bovines and differentially expressed genes identified.

In yet another aspect, the differentially regulated BVDV markers described herein may be used in screening methods to identify new therapeutic agents for the treatment of viral infections, particularly BVDV infections. For example, agents which down regulate the expression of genes which are upregulated in response to infection may have efficacy as antiviral agents.

I. DEFINITIONS

The following definitions are provided to facilitate an understanding of the present invention: The term "surrogate marker" or "infection marker" is a marker which is differentially expressed in animals infected with a pathological condition, such as a virus. Preferably, the marker is differentially expressed in persistent BVDV infection.

Specifically, a surrogate marker may be any gene expression product which is differentially expressed in persistently infected animals when compared to vaccinated or acutely infected animals, transiently infected and non-infected or non-vaccinated (normal) animals. A surrogate marker can be a polynucleotide, a protein, a peptide, or any gene expression product, but is preferably an mRNA or protein expression product. The surrogate markers described herein may also be useful for diagnosing invention with other RNA viruses which include for example, Influenza, HIV, Ebola virus, FeLv, FIP virus, Bluetongue virus, West Nile Virus, hepatitis C Virus and Epizootic Hemorrhagic Disease Virus. Thus, the term "surrogate marker" as used herein refers to those biological molecules which are differentially expressed in response to infection with any RNA virus.

A "persistently infected" calf is one that is infected in utero prior to 150 days of gestation, does not clear the virus and if it survives, will continue to shed virus. A "transiently infected" calf is one that is infected in utero after 150 days of gestation, recovers and clears the virus. An acutely infected animal is one that is infected postnatally and recovers, clearing the virus. A control animal is one that was never infected with virus.

A "BVDV surrogate marker" refers to a marker which is differentially expressed in animals infected with BVDV. Specifically, a BVDV surrogate marker may be any gene expression product which is differentially expressed in any or all of acutely infected BVDV animals, persistently infected BVDV animals, vaccinated BVDV animals, and normal animals. A surrogate marker can be a polynucleotide, a protein or peptide, or any gene expression product, but is preferably an mRNA or protein expression product.

A "BVDV surrogate marker profile" is an expression pattern of surrogate BVDV markers which correlates specifically to acute BVDV infection, persistent BVDV infection, BVDV vaccinated cattle, or non-BVDV infected cattle.

A "sample" or "patient sample" or "biological sample" generally refers to a sample which may be tested for a particular molecule, preferably a surrogate BVDV marker, including one or more surrogate BVDV polynucleotide, polypeptide, or antibody. Samples may include but are not limited to blood or skin, serum, plasma, urine, saliva, and the like. Most preferably, the sample is a skin sample or a blood sample from cattle.

"Blood" includes but is not limited to whole blood, blood treated or mixed with anticoagulants, and any component of whole blood, including but not limited to serum, plasma, buffy coat, and purified peripheral blood mononuclear cells.

A "ruminant" is an even-toed, herbivorous, ungulate mammal (Order Artiodactyla) that chews cud (ruminate) and has a complex, usually four-chambered stomach containing microorganisms that break down cellulose. Ruminants include but are not limited to cattle, sheep, antelope, deer, giraffes, elk, moose, caribou, yak and camelids (e.g., camel, llama, alpaca, vicuna and guanaco). "Ruminant test animal" is a ruminant suspected of being persistently infected with BVDV, and a "ruminant test animal" also encompasses a fetus of a pregnant ruminant test animal.

The term "cattle" as used herein includes any of numerous types of domestic quadrupeds held as property or raised for use, such as livestock, cows, bulls, bovine, steer, oxen, bison, and the like. The term "cattle" generally refers to multiple animals, but may also describe a single animal.

The term "ruminant nucleic acid" or "ruminant protein" refers to a nucleic acid or protein whose sequence is of ruminant origin. Preferably, a ruminant nucleic acid or ruminant protein is of bovine origin.

A "BVDV surrogate marker detector molecule" is a molecule which facilitates detecting or quantitating a BVDV surrogate marker. A BVDV surrogate marker detector molecule can be any molecule which facilitates detection of BVDV surrogate marker, including but not limited to a probe or primer which specifically hybridizes with a BVDV surrogate marker nucleic acid, or an antibody or fragment thereof which specifically binds to a BVDV surrogate marker polypeptide or peptide fragment.

The term "differential diagnosis" refers to a diagnosis which is able to differentiate between two or more different types of BVDV infection (for example, acute infection, persistent infection, or not infected.) This test also identifies previously vaccinated animals.

The phrase "consisting essentially of" when referring to a particular nucleotide or amino acid means a sequence having the properties of a given SEQ ID NO:.

For example, when used in reference to an amino acid sequence, the phrase includes the sequence per se and molecular modifications that would not affect the functional and unique characteristics of the sequence.

The term "nucleic acid molecule" describes a polymer of deoxyribonucleotides (DNA) or ribonucleotides (RNA). The nucleic acid molecule may be isolated from a natural source by cDNA cloning or subtractive hybridization or synthesized manually. The nucleic acid molecule may be synthesized manually by the triester synthetic method or by using an automated DNA synthesizer.

With regard to nucleic acids used in the invention, the term "isolated nucleic acid" is sometimes employed. This term, when applied to DNA, refers to a DNA molecule that is separated from sequences with which it is immediately contiguous (in the 5' and 3' directions) in the naturally occurring genome of the organism or virus from which it was derived. For example, the "isolated nucleic acid" may comprise a DNA molecule inserted into a vector, such as a plasmid or virus vector, or integrated into the genomic DNA of a prokaryote or eukaryote cells.

An "isolated nucleic acid molecule" may also comprise a cDNA molecule. An isolated nucleic acid molecule inserted into a vector is also sometimes referred to herein as a recombinant nucleic acid molecule.

The term "complementary" describes two nucleotides that can form multiple favorable interactions with one another. For example, adenine is complementary to thymine as they can form two hydrogen bonds. Similarly, guanine and cytosine are complementary since they can form three hydrogen bonds. Thus if a nucleic acid sequence contains the following sequence of bases, thymine, adenine, guanine and cytosine, a "complement" of this nucleic acid molecule would be a molecule containing adenine in the place of thymine, thymine in the place of adenine, cytosine in the place of guanine, and guanine in the place of cytosine. Because the complement can contain a nucleic acid sequence that forms optimal interactions with the parent nucleic acid molecule, such a complement can bind with high affinity to its parent molecule.

With respect to single stranded nucleic acids, particularly oligonucleotides, the term "specifically hybridizing" refers to the association between two single-stranded nucleotide molecules of sufficiently complementary sequence to permit such hybridization under pre-determined conditions generally used in the art (sometimes termed "substantially complementary"). In particular, the term refers to hybridization of an oligonucleotide with a substantially complementary sequence contained within a single-stranded DNA or RNA molecule of the invention, to the substantial exclusion of hybridization of the oligonucleotide with single-stranded nucleic acids of non-complementary sequence. Appropriate conditions enabling specific hybridization of single stranded nucleic acid molecules of varying complementarity are well known in the art.

For instance, one common formula for calculating the stringency conditions required to achieve hybridization between nucleic acid molecules of a specified sequence homology is set forth below (Sambrook et al., Molecular Cloning, Cold Spring Harbor Laboratory (1989): $Tm=81.5°\ C.+16.6\ Log\ [Na+]+0.41\ (\%\ G+C)-0.63\ (\%\ formamide)-600/\#bp$ in duplex.

As an illustration of the above formula, using $[Na+]=[0.368]$ and 50% formamide, with GC content of 42% and an average probe size of 200 bases, the Tm is 57° C. The Tm of a DNA duplex decreases by 1-1.5° C. with every 1% decrease in homology. Thus, targets with greater than about 75% sequence identity would be observed using a hybridization temperature of 42° C.

The stringency of the hybridization and wash depend primarily on the salt concentration and temperature of the solutions. In general, to maximize the rate of annealing of the probe with its target, the hybridization is usually carried out at salt and temperature conditions that are 20-25° C. below the calculated Tm of the hybrid.

Wash conditions should be as stringent as possible for the degree of identity of the probe for the target. In general, wash conditions are selected to be approximately 12-20° C. below the Tm of the hybrid. In regards to the nucleic acids of the current invention, a moderate stringency hybridization is defined as hybridization in 6×SSC, 5×Denhardt's solution, 0.5% SDS and 100 pg/ml denatured salmon sperm DNA at 42° C., and washed in 2×SSC and 0.5% SDS at 55° C. for 15 minutes. A high stringency hybridization is defined as hybridization in 6×SSC, 5×Denhardt's solution, 0.5% SDS and 100 pg/ml denatured salmon sperm DNA at 42° C., and washed in 1×SSC and 0.5% SDS at 65° C. for 15 minutes. A very high stringency hybridization is defined as hybridization in 6×SSC, 5×Denhardt's solution, 0.5% SDS and 100 pg/ml denatured salmon sperm DNA at 42° C., and washed in 0.1× SSC and 0.5% SDS at 65° C. for 15 minutes.

The term "oligonucleotide" as used herein refers to primers and probes of the present invention, and is defined as a nucleic acid molecule comprised of two or more ribo- or deoxy-ribonucleotides, preferably more than three. The exact size of the oligonucleotide will depend on various factors and on the particular application and use of the oligonucleotide. Oligonucleotides, which include probes and primers, can be any length from 3 nucleotides to the full length of the nucleic acid molecule, and explicitly include every possible number of contiguous nucleic acids from 3 through the full length of the polynucleotide. Preferably, oligonucleotides, which include probes and/or primers are at least about 10 nucleotides in length, more preferably at least 15 nucleotides in length, more preferably at least about 20 nucleotides in length.

The term "probe" as used herein refers to an oligonucleotide, polynucleotide or nucleic acid, either RNA or DNA, whether occurring naturally as in a purified restriction enzyme digest or produced synthetically, which is capable of annealing with or specifically hybridizing to a nucleic acid with sequences complementary to the probe. A probe may be either single-stranded or double-stranded. The exact length of the probe will depend upon many factors, including temperature, source of probe and use of the method. For example, for diagnostic applications, depending on the complexity of the target sequence, the oligonucleotide probe typically contains 15-25 or more nucleotides, although it may contain fewer nucleotides. The probes herein are selected to be complementary to different strands of a particular target nucleic acid sequence.

This means that the probes must be sufficiently complementary so as to be able to "specifically hybridize" or anneal with their respective target strands under a set of pre-determined conditions. Therefore, the probe sequence need not reflect the exact complementary sequence of the target. For example, a non-complementary nucleotide fragment may be attached to the 5' or 3'end of the probe, with the remainder of the probe sequence being complementary to the target strand. Alternatively, non-complementary bases or longer sequences can be interspersed into the probe, provided that the probe sequence has sufficient complementarity with the sequence of the target nucleic acid to anneal therewith specifically.

The term "primer" as used herein refers to an oligonucleotide, either RNA or DNA, either single-stranded or double-stranded, either derived from a biological system, generated by restriction enzyme digestion, or produced synthetically which, when placed in the proper environment, is able to functionally act as an initiator of template-dependent nucleic acid synthesis. When presented with an appropriate nucleic acid template, suitable nucleoside triphosphate precursors of nucleic acids, a polymerase enzyme, suitable cofactors and conditions such as a suitable temperature and pH, the primer may be extended at its 3 terminus by the addition of nucleotides by the action of a polymerase or similar activity to yield a primer extension product. The primer may vary in length depending on the particular conditions and requirement of the application. For example, in diagnostic applications, the oligonucleotide primer is typically 15-25 or more nucleotides in length. The primer must be of sufficient complementarity to the desired template to prime the synthesis of the desired extension product, that is, to be able anneal with the desired template strand in a manner sufficient to provide the 3'hydroxyl moiety of the primer in appropriate juxtaposition for use in the initiation of synthesis by a polymerase or similar enzyme. It is not required that the primer sequence represent an exact complement of the desired template.

For example, a non-complementary nucleotide sequence may be attached to the 5'end of an otherwise complementary primer. Alternatively, non-complementary bases may be interspersed within the oligonucleotide primer sequence, provided that the primer sequence has sufficient complementarity with the sequence of the desired template strand to functionally provide a template-primer complex for the synthesis of the extension product. Polymerase chain reaction (PCR) has been described in U.S. Pat. Nos. 4,683,195, 4,800,195, and 4,965,188, the entire disclosures of which are incorporated by reference herein.

The term "vector" relates to a single or double stranded circular nucleic acid molecule that can be transfected or transformed into cells and replicate independently or within the host cell genome. A circular double stranded nucleic acid molecule can be cut and thereby linearized upon treatment with restriction enzymes. An assortment of vectors, restriction enzymes, and the knowledge of the nucleotide sequences that are targeted by restriction enzymes are readily available to those skilled in the art. A vector of the invention includes any replicon, such as a plasmid, cosmid, bacmid, phage or virus, to which another genetic sequence or element (either DNA or RNA) may be attached so as to bring about the replication of the attached sequence or element. A nucleic acid molecule of the invention can be inserted into a vector by cutting the vector with restriction enzymes and ligating the two pieces together.

Many techniques are available to those skilled in the art to facilitate transformation, transfection, or transduction of the expression construct into a prokaryotic or eukaryotic organism. The terms "transformation", "transfection", and "transduction" refer to methods of inserting a nucleic acid and/or expression construct into a cell or host organism. These methods involve a variety of techniques, such as treating the cells with high concentrations of salt, an electric field, or detergent, to render the host cell outer membrane or wall permeable to nucleic acid molecules of interest, microinjection, PEG-fusion, and the like.

The term "promoter element" describes a nucleotide sequence that is incorporated into a vector that, once inside an appropriate cell, can facilitate transcription factor and/or polymerase binding and subsequent transcription of portions of the vector DNA into mRNA. In one embodiment, the promoter element of the present invention precedes the 5'end of the BVDV surrogate marker nucleic acid molecule such that the latter is transcribed into mRNA. Host cell machinery then translates mRNA into a polypeptide.

Those skilled in the art will recognize that a nucleic acid vector can contain nucleic acid elements other than the promoter element and the BVDV surrogate marker gene nucleic acid molecule. These other nucleic acid elements include, but are not limited to, origins of replication, ribosomal binding sites, nucleic acid sequences encoding drug resistance enzymes or amino acid metabolic enzymes, and nucleic acid sequences encoding secretion signals, periplasm or peroxisome localization signals, or signals useful for polypeptide purification.

An "expression operon" refers to a nucleic acid segment that may possess transcriptional and translational control sequences, such as promoters, enhancers, translational start signals (e.g., ATG or AUG codons), polyadenylation signals, terminators, and the like, and which facilitate the expression of a polypeptide coding sequence in a host cell or organism.

As used herein, the terms "reporter", "reporter system", "reporter gene", or "reporter gene product" shall mean an operative genetic system in which a nucleic acid comprises a gene that encodes a product that when expressed produces a reporter signal that is a readily measurable, e.g., by biological assay, immunoassay, radio immunoassay, or by colorimetric, fluorogenic, chemiluminescent or other methods. The nucleic acid may be either RNA or DNA, linear or circular, single or double stranded, antisense or sense polarity, and is operatively linked to the necessary control elements for the expression of the reporter gene product. The required control elements will vary according to the nature of the reporter system and whether the reporter gene is in the form of DNA or RNA, but may include, but not be limited to, such elements as promoters, enhancers, translational control sequences, poly A addition signals, transcriptional termination signals and the like.

The introduced nucleic acid may or may not be integrated (covalently linked) into nucleic acid of the recipient cell or organism. In bacterial, yeast, plant and mammalian cells, for example, the introduced nucleic acid may be maintained as an episomal element or independent replicon such as a plasmid. Alternatively, the introduced nucleic acid may become integrated into the nucleic acid of the recipient cell or organism and be stably maintained in that cell or organism and further passed on or inherited to progeny cells or organisms of the recipient cell or organism. Finally, the introduced nucleic acid may exist in the recipient cell or host organism only transiently.

The term "selectable marker gene" refers to a gene that when expressed confers a selectable phenotype, such as antibiotic resistance, on a transformed cell.

The term "operably linked" means that the regulatory sequences necessary for expression of the coding sequence are placed in the DNA molecule in the appropriate positions relative to the coding sequence so as to effect expression of the coding sequence. This same definition is sometimes applied to the arrangement of transcription units and other transcription control elements (e.g., enhancers) in an expression vector.

The term "tag", "tag sequence", or "protein tag" refers to a chemical moiety, either a nucleotide, oligonucleotide, polynucleotide or an amino acid, peptide or protein or other chemical, that when added to another sequence, provides additional utility or confers useful properties, particularly in the detection or isolation, of that sequence. Thus, for example, a homopolymer nucleic acid sequence or a nucleic acid sequence complementary to a capture oligonucleotide may be added to a primer or probe sequence to facilitate the subsequent isolation of an extension product or hybridized product. In the case of protein tags, histidine residues (e.g., 4 to 8 consecutive histidine residues) may be added to either the amino- or carboxy-terminus of a protein to facilitate protein isolation by chelating metal chromatography. Alternatively, amino acid sequences, peptides, proteins or fusion partners representing epitopes or binding determinants reactive with specific antibody molecules or other molecules (e.g., flag epitope, c-myc epitope, transmembrane epitope of the influenza A virus hemaglutinin protein, protein A, cellulose binding domain, calmodulin binding protein, maltose binding protein, chitin binding domain, glutathione S-transferase, and the like) may be added to proteins to facilitate protein isolation by procedures such as affinity or immunoaffinity chromatography.

Chemical tag moieties include such molecules as biotin, which may be added to either nucleic acids or proteins and facilitates isolation or detection by interaction with avidin reagents, and the like. Numerous other tag moieties are known to, and can be envisioned by the trained artisan, and are contemplated to be within the scope of this definition.

A "specific binding pair" comprises a specific binding member (sbm) and a binding partner (bp) which have a particular specificity for each other and which in normal conditions bind to each other in preference to other molecules. Examples of specific binding pairs are antigens and antibodies, ligands and receptors and complementary nucleotide sequences. The skilled person is aware of many other examples. Further, the term "specific binding pair" is also applicable where either or both of the specific binding member and the binding partner comprise a part of a large molecule. In embodiments in which the specific binding pair comprises nucleic acid sequences, they will be of a length to hybridize to each other under conditions of the assay, preferably greater than 10 nucleotides long, more preferably greater than 15 or 20 nucleotides long.

An "antibody" or "antibody molecule" is any immunoglobulin, including antibodies and fragments thereof, that binds to a specific antigen. The term includes polyclonal, monoclonal, chimeric, and bispecific antibodies. Exemplary antibody fragments, capable of binding an antigen or other binding partner, are Fab fragment consisting of the VL, VH, Cl and CH1 domains; the Fd fragment consisting of the VH and CH1 domains; the Fv fragment consisting of the VL and VH domains of a single arm of an antibody; the dAb fragment which consists of a VH domain; isolated CDR regions and F (ab') 2 fragments, a bivalent fragment including two Fab fragments linked by a disulphide bridge at the hinge region. Single chain Fv fragments are also included.

With respect to antibodies, the term "immunologically specific" refers to antibodies that bind to one or more epitopes of a protein or compound of interest, but which do not substantially recognize and bind other molecules in a sample containing a mixed population of antigenic biological molecules. Exemplary antibodies bind to a protein or peptide fragment encoded by a nucleotide sequence set forth in Tables 1-9.

A "detection reagent" or a "marker detection reagent" is any substance which has binding affinity for a BVDV specific molecule, and includes but is not limited to nucleic acid molecules with sufficient affinity to hybridize to the BVDV specific marker, probes, primers, antibodies, fragments thereof, and the like. The "detection reagent" or "marker detection reagent" may optionally be detectably labeled.

The term "detectable label" is used herein to refer to any substance whose detection or measurement, either directly or indirectly, by physical or chemical means, is indicative of the presence of a target bioentity in a test sample. Representative examples of useful detectable labels, include, but are not limited to the following: molecules or ions directly or indirectly detectable based on light absorbance, fluorescence, reflectance, light scatter, phosphorescence, or luminescence properties; molecules or ions detectable by their radioactive properties; molecules or ions detectable by their nuclear magnetic resonance or paramagnetic properties. Included among the group of molecules indirectly detectable based on light absorbance or fluorescence, for example, are various enzymes which cause appropriate substrates to convert, e.g., from non-light absorbing to light absorbing molecules, or from non-fluorescent to fluorescent molecules.

As used herein, the term "informational fragments" refers to fragments of a nucleic acid or protein whose expression level can be detected and are informative for BVDV infection. Informational fragments preferably are differentially expressed in BVDV subjects as compared to uninfected subjects. The informational fragments and sequences corresponding to said fragments are exemplified in Table 12 and descriptions relating to Table 12.

II. SURROGATE BVDV NUCLEIC ACID MOLECULES, PROBES, AND PRIMERS AND METHODS OF PREPARING THE SAME

Encompassed by the invention are surrogate BVDV nucleic acid molecules, nucleic acid molecules which encode isolated, enriched, or purified surrogate BVDV proteins or peptides, including allelic variations, analogues, fragments, derivatives, mutants, and modifications of the same.

Surrogate BVDV nucleic acid molecules, and nucleic acid sequences encoding surrogate BVDV proteins may be isolated from appropriate biological sources using methods known in the art. In a preferred embodiment, a cDNA clone is isolated from a cDNA expression library of bovine origin. Preferably, the sample is isolated from a bovine which has been vaccinated for, or has acute, or persistent BVDV infection.

Surrogate BVDV marker polynucleotides can be any one of, or any combination of the markers shown in Tables 1-9, and 12 further may include variants which are at least about 75%, or 80% or 85% or 90% or 95%, and often, more than 90%, or more than 95% homologous to the markers shown in Tables 1-9 and 12 over the full length sequence. Surrogate BVDV marker polynucleotides also may be 60% or 65% or 70% or 75% or 80% or 85% or 90% or 95% or 97% or 98% or 99% or greater than 99% homologous to the markers shown in Tables 1-9 and 12, over the full length sequence. All homology may be computed by algorithms known in the art, such as BLAST, described in Altschul et al. (1990), J. Mol. Biol. 215: 403-10, or the Smith-Waterman homology search algorithm as implemented in MPSRCH program (Oxford Molecular). Someone of ordinary skill in the art would readily be able to determine the ideal gap open penalty and gap extension penalty for a particular nucleic acid sequence.

Exemplary search parameters for use with the MPSRCH program in order to identify sequences of a desired sequence identity are as follows: gap open penalty: −16; and gap extension penalty: −4.

Degenerate variants are also encompassed by the instant invention. The degeneracy of the genetic code permits substitution of certain codons by other codons, which specify the same amino acid and hence would give rise to the same protein. The nucleic acid sequence can vary substantially since, with the exception of methionine and tryptophan, the known amino acids can be coded for by more than one codon. Thus, portions or all of the markers could be synthesized to give a nucleic acid sequence significantly different from that shown in Tables 1-9 and 12. The encoded amino acid sequence thereof would, however, be preserved.

In addition, the nucleic acid sequence may comprise a nucleotide sequence which results from the addition, deletion or substitution of at least one nucleotide to the 5'-end and/or the 3'-end of one or more of the markers shown in Tables 1-9 and 12, or a derivative thereof. Any nucleotide or polynucleotide may be used in this regard, provided that its addition, deletion or substitution does not alter the amino acid sequence which is encoded by the nucleotide sequence, or it still shares a region of homology with one or more of the markers shown in Tables 1-9 and 12. For example, the present invention is intended to include any nucleic acid sequence resulting from the addition of ATG as an initiation codon at the 5'-end of the surrogate BVDV marker nucleic acid sequence or its functional derivative, or from the addition of TTA, TAG or TGA as a termination codon at the 3'-end of the inventive nucleotide sequence or its derivative. Moreover, the nucleic acid molecule of the present invention may, as necessary, have restriction endonuclease recognition sites added to its 5'-end and/or 3'-end.

Such functional alterations of a given nucleic acid sequence afford an opportunity to promote secretion and/or processing of heterologous proteins encoded by foreign nucleic acid sequences fused thereto. All variations of the nucleotide sequence of the markers shown in Tables 1-9 and 12 and fragments thereof permitted by the genetic code are, therefore, included in this invention.

In an alternative embodiment, utilizing the sequence information provided by the cDNA sequence, genomic clones encoding a surrogate BVDV marker gene may be isolated.

Alternatively, cDNA or genomic clones having homology with the markers shown in Tables 1-9 and 12 may be isolated from other species, such as mouse or human, using oligonucleotide probes corresponding to predetermined sequences within surrogate BVDV marker gene.

III. SURROGATE BVDV PROTEINS (ANTIGENS) AND METHODS OF MAKING THE SAME

Encompassed by the invention are isolated, purified, or enriched surrogate BVDV polypeptides, including allelic variations, analogues, fragments, derivatives, mutants, and modifications of the same which are differentially expressed in BVDV animals. Preferably, surrogate BVDV marker polypeptides include polypeptides encoded by one or more of the sequences shown in Tables 1-9 and 12. Surrogate BVDV marker function is defined above, and includes increased or decreased expression in response to BVDV infection, cross-reactivity with an antibody reactive with the polypeptides encoded by one or more of the sequences shown in Tables 1-9 and 12 or sharing an epitope with the same (as determined for example by immunological cross-reactivity between the two polypeptides). Surrogate BVDV marker polypeptides or proteins can be encoded by one or more of the sequences shown in Tables 1-9 and 12 further may include variants which are at least about 75%, or 80% or 85% or 90% or 95%, and often, more than 90%, or more than 95% homologous to the same over the full length sequence.

Surrogate BVDV marker polypeptides also may be 60% or 65% or 70% or 75% or 80% or 85% or 90% or 95% or 97% or 98% or 99% or greater than 99% homologous to polypeptides encoded by one or more of the sequences shown in Tables 1-9 and 12 over the full length sequence. All homology may be computed by algorithms known in the art, such as BLAST, described in Altschul et al. (1990), J. Mol. Biol. 215: 403-10, or the Smith-Waterman homology search algorithm as implemented in MPSRCH program (Oxford Molecular). Someone of ordinary skill in the art would readily be able to determine the ideal gap open penalty and gap extension penalty for a particular protein sequence. Exemplary search parameters for use with the MPSRCH program in order to identify sequences of a desired sequence identity are as follows: gap open penalty: −12; and gap extension penalty: −2.

A full-length or truncated surrogate BVDV protein of the present invention may be prepared in a variety of ways, according to known methods. The protein may be purified from appropriate sources, e.g., transformed bacterial or animal cultured cells or tissues, by immunoaffinity purification. Additionally, the surrogate BVDV protein may be produced using in vitro expression methods known in the art. For example, a cDNA or gene may be cloned into an appropriate in vitro transcription vector, such as pSP64 or pSP65 for in vitro transcription, followed by cell-free translation in a suitable cell-free translation system, such as wheat germ or rabbit reticulocyte lysates. In vitro transcription and translation systems are commercially available, e.g., from Promega Corp., Madison, Wis. or Invitrogen Corp., Carlsbad, Calif.

The surrogate BVDV proteins produced by gene expression in a recombinant prokaryotic or eukaryotic system may be purified according to methods known in the art. In a preferred embodiment, a commercially available expression/secretion system can be used, whereby the recombinant protein is expressed and thereafter secreted from the host cell, to be easily purified from the surrounding medium. If expression/secretion vectors are not used, an alternative approach involves purifying the recombinant protein by affinity separation, such as by immunological interaction with antibodies that bind specifically to the recombinant protein or nickel columns for isolation of recombinant proteins tagged with 6-8 histidine residues at their N-terminus or C-terminus.

Alternative tags may comprise the FLAG epitope or the hemagglutinin epitope. Such methods are commonly used by skilled practitioners.

IV. ANTI-SURROGATE BVDV PROTEIN ANTIBODIES AND METHODS OF MAKING THE SAME

The present invention also provides methods of making and using antibodies capable of immunospecifically binding to surrogate BVDV proteins. Polyclonal antibodies directed toward surrogate BVDV proteins may be prepared according to standard methods. In a preferred embodiment, monoclonal antibodies are prepared, which react immunospecifically with the various epitopes on the surface of the surrogate BVDV protein. Monoclonal antibodies may be prepared according to general methods of Kohler and Milstein, following standard protocols.

Purified BVDV antigens, or fragments thereof, may be used to produce polyclonal or monoclonal antibodies which also may serve as sensitive detection reagents for the various types of BVDV infection (acute, PI, vaccination reaction, and not infected). Recombinant techniques enable expression of fusion proteins containing part or all of BVDV. The surrogate BVDV protein itself, or surface proteins or antigens from the surrogate BVDV protein may be used to advantage to generate an array of monoclonal antibodies specific for various epitopes of the surrogate BVDV protein, thereby providing even greater sensitivity for detection of the surrogate BVDV protein (and thus BVDV infection) in samples.

Polyclonal or monoclonal antibodies that immunospecifically interact with BVDV antigens can be utilized for identifying and diagnosing BVDV. For example, antibodies may be utilized for affinity separation of proteins with which they immunospecifically interact. Antibodies may also be used to immunoprecipitate proteins from a sample containing a mixture of proteins and other biological molecules.

Other uses of anti-surrogate BVDV protein antibodies are described below.

V. METHODS OF USING SURROGATE BVDV POLYNUCLEOTIDES, POLYPEPTIDES, AND ANTIBODIES FOR SCREENING AND DIAGNOSTIC ASSAYS

Surrogate BVDV nucleic acids may be used for a variety of purposes in accordance with the present invention. Surrogate BVDV nucleic acids (DNA, RNA, fragments thereof, etc.), or protein-encoding DNA, RNA, or fragments thereof may be used as probes to detect the presence of surrogate BVDV nucleic acids or protein in a sample. Methods in which surrogate BVDV nucleic acids and protein-encoding nucleic acids may be utilized as probes for such assays include, but are not limited to: (1) in situ hybridization; (2) Southern hybridization (3) northern hybridization; (4) gene chip analysis and (5) assorted amplification reactions such as polymerase chain reactions (PCR).

Exemplary surrogate BVDV nucleic acids and nucleic acids encoding exemplary surrogate BVDV proteins or peptides are described in Tables 1-9 and 12.

The surrogate BVDV nucleic acids of the invention may also be utilized as probes to identify related surrogate BVDV variants. As is well known in the art, hybridization stringencies may be adjusted to allow hybridization of nucleic acid probes with complementary sequences of varying degrees of homology. Thus, BVDV surrogate marker nucleic acids may be used to advantage to identify and characterize other genes of varying degrees of relation to BVDV surrogate markers, thereby enabling further characterization of BVDV surrogate markers. Additionally, they may be used to identify genes encoding proteins that interact with BVDV surrogate markers (e.g., by the "interaction trap" technique—see for example Current Protocols in Molecular Biology, ed. Ausubel, F. M., et al., John Wiley & Sons, NY, 1997), which should further accelerate identification of the molecular components involved in BVDV. Finally, they may be used in assay methods to detect BVDV.

Polyclonal or monoclonal antibodies immunologically specific for proteins encoded by BVDV surrogate markers or peptide fragments thereof may be used in a variety of assays designed to detect and quantitate the protein, as well as to detect ruminant BVDV by detecting upregulation of BVDV surrogate markers. Such assays include, but are not limited to: (1) flow cytometric analysis; (2) immunochemical localization of BVDV specific markers in a body cell, tissue, or fluid; and (3) immunoblot analysis (e.g., dot blot, Western blot) (4) ELISA; (5) radioimmunoassay of extracts from various cells.

Additionally, as described above, anti-surrogate BVDV marker protein can be used for purification of surrogate BVDV markers (e.g., affinity column purification, immunoprecipitation).

Further, assays for detecting and quantitating surrogate BVDV markers, or to detect ruminant BVDV by detecting upregulation of BVDV specific markers may be conducted on any type of biological sample where upregulation of these molecules is observed, including but not limited to body fluids (including blood, serum, plasma, milk, or saliva), any type of cell (such as skin cells, or blood cells, or endothelial cells), or body tissue. The sample from a test animal is can be obtained between day 82 and day 160 of gestation for use in diagnosing BVDV.

From the foregoing discussion, it can be seen that surrogate BVDV marker nucleic acids, surrogate BVDV marker expressing vectors, surrogate BVDV marker proteins and anti-surrogate BVDV marker antibodies of the invention can be used to detect surrogate BVDV marker expression in body tissue, cells, or fluid, and alter BVDV specific marker protein expression for purposes of assessing the genetic and protein interactions involved in BVDV and infection.

In most embodiments for screening for surrogate BVDV mRNA, surrogate BVDV nucleic acid in the sample will initially be amplified, e.g. using PCR, to increase the amount of the template as compared to other sequences present in the sample. This allows the target sequences to be detected with a high degree of sensitivity if they are present in the sample.

Thus any of the aforementioned techniques may be used as a diagnostic tool for detecting surrogate BVDV markers.

Further, these techniques could be used to diagnose infectious diseases in humans, by detection of a surrogate marker (rather than a viral antigen). For example, differential gene expression could be measured in HIV, Ebola, Hepatitis, and Herpes viral infections, etc. These tests are advantageous in that they are directed to detection of a theoretically harmless surrogate marker, rather than the infectious agent itself.

Such techniques could also be used to diagnose infectious diseases in companion animals by detection of a surrogate marker (rather than a viral antigen). An example of a potential application would be the diagnosis of feline infectious peritonitis of cats and latent viral infections caused by herpes viruses for which current diagnostic tests (based on isolation and characterization of the virus) have a marginal reliability. In addition, this technology could also be used for the diagnosis of cancer through the identification of surrogate cancer markers.

The instant inventive method improves upon the accuracy of current BVDV tests. A combination test, which measures both BVDV itself, and also one or more BVDV surrogate marker, to differentially diagnose BVDV infection provides superior diagnostic results in the field.

VI. ASSAYS FOR DIFFERENTIALLY DIAGNOSING BVDV USING SPECIFIC SURROGATE MARKERS

In accordance with the present invention, it has been discovered that Bovine Viral Diarrhea Virus (BVDV) is correlated with increased expression levels of certain markers, including but not limited to mRNAs and proteins.

Thus, these molecules may be utilized in conventional assays to differentially diagnose BVDV. The detection of one or more of these differentially expressed BVDV surrogate molecules in a sample is indicative of BVDV. Similarly, specific patterns of expression allow detection of acute versus persistent infection. Alternatively, the absence of these molecules in a sample indicates that a ruminant is not infected with BVDV.

In an exemplary method, a blood sample is obtained from a bovine suspected of having an acute or persistent BVDV infection. Optionally, the blood may be centrifuged through a Hypaque gradient to obtain the buffy coat. The blood or buffy coat preparation is diluted and subjected to polymerase chain reaction conditions suitable for amplification of the BVDV surrogate marker encoding mRNA. In certain applications, it may be necessary to include an agent, which lyses cells prior to performing the PCR.

Such agents are well known to the skilled artisan. The reaction products are then analyzed, e.g., via gel electrophoresis. An increase in BVDV surrogate marker mRNA levels relative to levels obtained from a non-infected bovine is indicative of BVDV in the animal being tested. Alternatively, an increase in BVDV surrogate markers in AI animals relative to PI animals, or in PI animals, relative to AI animals, can differentially diagnose acute infection, or persistent infection.

In an alternative method, a skin tissue sample is obtained from the bovine suspected of having acute or persistent BVDV infection. The cells are then lysed and PCR performed. As above, an increase in BVDV surrogate marker mRNA expression levels relative to those observed in a non-BVDV infected animal being indicative of BVDV in the test animal.

It is also possible to detect BVDV using immunoassays. In an exemplary method, blood is obtained from a bovine suspected of being infected with BVDV. As above, the blood may optionally be centrifuged through a Hypaque gradient to obtain a buffy coat. The blood or buffy coat sample is diluted and at least one antibody immunologically specific for BVDV surrogate markers is added to the sample. In a preferred embodiment, the antibody is operably linked to a detectable label. Also as described above, the cells may optionally be lysed prior to contacting the sample with the antibodies immunologically specific for BVDV surrogate markers.

Increased production of BVDV surrogate markers is assessed as a function of an increase in the detectable label relative to that obtained in parallel assays using blood from non-BVDV infected cow. In yet another embodiment, the blood or buffy coat preparation is serially diluted and aliquots added to a solid support.

Suitable solid supports include multi-well culture dishes, blots, filter paper, and cartridges. The solid support is then contacted with the detectably labeled antibody and the amount of BVDV surrogate marker protein (e.g., a protein or peptide encoded by a nucleic acid of Tables 1-9 and 12) in the animal suspected of being infected with BVDV is compared with the amount obtained from a non-AI or PI animal as a function of detectably labeled antibody binding. An alteration in the BVDV surrogate marker protein level in the test animal relative to the non-AI or PI infected control animal is indicative of acute or persistent BVDV. In preferred embodiments, at least 1, at least 2, at least 5, or at least 10 BVDV markers from Tables 1-9 or Table 12 will be detected to diagnose BVDV infection.

In another embodiment, a first antibody which binds to a first epitope on a target protein is placed in the well of a cartridge. Whole blood, blood collected in the presence of anticoagulants (e.g., sodium citrate, heparin), plasma, or serum is placed into the well of the cartridge. The target protein, if present in the sample, is bound by the first antibody, and then migrates laterally by a wicking action, through a filter which has been sprayed with second antibody. The second antibody has affinity for a second epitope on the target protein, or alternatively for the first antibody. The second antibody is optionally labeled with a detectable label (e.g. radiolabel, gold, biotin, enzyme, etc.) The second antibody localizes the antigen, and results in the appearance of a line on the filter. The first and second antibodies may be generated against the full length target protein, or against the N-terminal or C-terminal halves of the target protein, so that they recognize different epitopes of the target protein.

The foregoing immunoassay methods may also be applied to any type of sample, including a urine sample.

VII. KITS AND ARTICLES OF MANUFACTURE

Any of the aforementioned products or methods can be incorporated into a kit which may contain a BVDV specific polynucleotide, an oligonucleotide, a polypeptide, a peptide, a solid support (e.g., filters, cartridges, gene chips) an antibody, a label, marker, or reporter, a pharmaceutically acceptable carrier, a physiologically acceptable carrier, instructions for use, negative and positive control samples, a container, a vessel for administration, an assay substrate, or any combination thereof.

The following Examples illustrate certain embodiments of the invention. They are not intended to limit its scope in any way. The materials and methods to facilitate the practice of the invention are also provided hereinbelow.

Example 1

Bovine viral diarrhea virus (BVDV) infections are responsible for important economic losses due to reproductive wastage, and respiratory and digestive disease in cattle. Infection of the early developing fetus frequently results in persistent infection (PI). PI animals are the main source of new infection in herd mates. The complex host-viral interactions resulting from persistent infection are minimally understood, particularly in the bovine host. The idea that gene expression would differ in bloods collected from PI animals when compared to non-infected steers was examined. In preliminary studies, bloods were collected from three PI or three control steers and were processed to yield total cellular RNA. Labeled RNA was used to screen six independent bovine Affymetrix DNA chips, and analyzed for fold-changes at the University of Colorado Health Sciences Center Microarray Facility. The top 100 up-regulated genes belonged to MHC class I (45-fold), antiviral (32-100 fold), transcription factor (8-12 fold), interferon stimulated genes (5-28 fold), bone remodeling (4-9 fold), and chemokine (2-4) families. The top 100 down-regulated genes belonged to adhesion (5-10 fold), T-cell receptor (5-10 fold), extracellular matrix (3-5 fold), growth factor (2-3 fold), and transcription factor (2-3 fold) families. It can be concluded from these findings that persistent infection with BVDV results in antiviral responses in blood cells which includes induction of type 1 interferon-induced genes, chemokine-mediated immune responses and bone remodeling with a concomitant suppression of extracellular remodeling, adhesion and T-cell-mediated responses. Thus, in accordance with the present invention, single and/or multiplexing diagnostics for identifying cattle that are persistently infected with BVDV are provided.

BVDV is divided into two biotypes: cytopathic (cp) and non-cytopathic (ncp). There are at least two recognized genotypes based on the sequence of the 5' untranslated region, type I and type II, and additional sub-genotypes. Within each genotype, there are several strains that cause different degrees of clinical signs. The pathogenesis of BVDV infection has features that are unique to this virus and that vary with the virulence of the viral strain and age of the animal at the time of infection.

Particularly interesting are the outcomes of infection of the fetus. Infection of the fetus during the first 150 days of gestation, when the immune system has not yet developed, can lead to the generation of PI calves (FIG. 1). Some of these PI calves die soon after birth, but others live for relatively long periods of time without showing any clinical signs. PI animals cannot eliminate the infecting BVDV from their system and continuously release high amounts of virus in their bodily secretions. This makes them a continuous source of infection within the herd and potentially to other herds. When the infection occurs after 150 days of gestation (post-development of the immune system) or after birth, the infection is referred to as acute and these animals, which clear the virus, are frequently called transiently infected (TI). The clinical manifestations of acute infections with BVDV range from sub-clinical, or unapparent infections, to embryonic death, abortions, stillbirths, and malformed or slow-growing calves. Although recent studies indicate that transient infection of the fetus may cause long-term detrimental effects in the development of the calf, the basis for these effects is not clearly understood.

Acute infection with the ncp biotype results in inhibition of double-stranded RNA-induced apoptosis and type 1 interferon, both indicated as plausible contributors to the establishment of persistent infection. However, in vitro and in vivo infections with the cp biotype induce apoptosis and are associated with increased type I interferon production.

The role of PI animals in the perpetuation of BVDV infections cannot be overemphasized. The presence of a single PI calf in a herd can cause severe losses within that herd and any herd with which the PI calf makes contact. The large percentage of seropositive cattle due to vaccination in the USA diminishes the value of serology as a monitoring test. In addition, PI animals have absent, extremely low or fluctuating titers against the strain that causes the persistent infection, potentially leading to misdiagnosis, particularly when serology is used as the only test. Current diagnostic tests based on the detection of viral antigen or viral RNA are effective tools for the identification of postnatal detection of PI animals. However, since PI animals shed high amounts of virus, early elimination of PI fetuses should greatly contribute to disrupting the infectious viral cycle.

In other preliminary studies, it has been demonstrated that calves persistently infected with BVDV present a differential pattern of gene expression in the blood when compared to vaccinated or acutely infected age-matched herd mates. Gene expression profiles were examined in the whole blood of one year old PI and non-infected calves that were naturally infected with BVDV using DNA microarray approaches.

Blood samples were collected from three BVDV PI and three vaccinated, non-infected control calves in sodium citrate tubes and placed on ice. RNA was isolated using the QIAamp RNA Blood Mini Kit following the manufacturer's instructions (Qiagen). Red blood cells were selectively lysed, and white cells were collected by centrifugation. White cells were then lysed using highly denaturing conditions, which immediately inactivate RNases. After homogenization using the QIAshredder spin column, the sample was applied to the QIAamp spin column. Total RNA binds to the QIAamp membrane and contaminants were washed away, leaving pure RNA which was eluted in 30-100 μl RNase-free water.

The total RNA was isolated and used for transcriptional profiling by screening the Affymetrix bovine DNA chip. Biotinylated cRNA (15 μg), generated from each RNA sample (n=6 total), was hybridized to the bovine Affymetrix GeneChip (features of which are shown below) Array (n=6 total). Data were analyzed using Affymetrix Microarray Suite Software version 5.0 for absolute and pair-wise comparison analyses. Normalized expression values for the mean and standard deviation of three replicate average difference scores were calculated for each gene. Comparisons were performed using the Student's t test (P<0.05 was considered significant). The raw data were interpreted using GeneSpring (version 5.0, Silicon Genetics, Redwood, Calif.) and GeneSifter software (vizX Labs, LLC, Seattle, Wash.).

| Critical Specifications | |
|---|---|
| Bos taurus (Bovine) probe sets | 24,072 |
| Bos taurus (Bovine) transcripts | approximately 23,000 |
| UniGene clusters | approximately 19,000 |
| Unique probe sets to single species: | |
| Number of arrays in set | one |
| Array format | 100 |
| Feature size | 11 μm |
| Oligonucleotide probe length | 25-mer |
| Probe pairs/sequence | 11 |
| Hybridization controls: | bioB, bioC, bioD, from E. coli and cre from P1 B. subtilis |
| Poly-A controls: | dap, lys, phe, thr, trp from B. subtilis |
| Housekeeping/Control genes: | actin, GAPDH, efIα, 5.8S rRNA, 12S rRNA, 18S rRNA, cyclophilin B, glutathione S-transferase, lactophorin, translation initiation factor eIF-4E |
| Detection sensitivity | 1:100,000[1] |

[1]As measured by detection in comparative analysis between a complex target containing spiked control transcriptions and a complex target with no spikes © Affymetrix—2007

Results

Two hundred genes were up-regulated in blood from PI when compared to vaccinated control calves. Known attributes of the top 100 up-regulated genes and fold changes are listed below:

| | |
|---|---|
| 45 fold | MHC Class I Molecules |
| 10-32 fold | Antiviral genes |
| 8-12 fold | Signal Transduction Molecules |
| 5-28 fold | Type 1 Interferon-Induced Genes (FIG. 2) |
| 4-9 fold | Bone Remodeling Genes |
| 3-6 fold | Cytoskeletal Remodeling Genes |
| 2-4 fold | Chemokine Ligands and Receptors |

One hundred genes were down-regulated in blood from PI when compared to control calves. Known attributes of the top 100 down-regulated genes and fold changes are listed below:

| | |
|---|---|
| 5-10 fold | Adhesion Molecules |
| 5-10 fold | T Cell Receptors |
| 3-5 fold | Extracellular Matrix |
| 2-3 fold | Growth Factors |
| 2-3 fold | Chemokine Ligands |
| 2-3 fold | Transcription Factors |

See FIG. 2.

Following more extensive and stringent analysis of microarray data described above, the following up-regulated (Table 1) and down-regulated (Table 2) genes were identified as preferred bovine blood markers for BVDV persistent infection (n=2 steers) when compared with controls (n=3 steers). MX2, 2'-5' oligoadenylate synthetase (OAS) and Interferon-Stimulated Protein, 15 kDa serve as examples of good markers for cattle with a BVDV PI infection when compared to non-infected controls. See FIG. 3.

TABLE 1

Preferred blood cell gene markers that are up-regulated in bloods from steers that are persistently infected with BVDV when compared to non-infected steers.

Pairwise Analysis: BVDV Steers Con vs PI
[Reports: Ontology|KEGG|Scatter Plot]
[Results: Export|Save]

| | Group 1 | Group 2 |
|---|---|---|
| Conditions: | Control | PI |
| Experiments: | 46038, 46039, 46040 | 46041, 46042 |
| Significance: | 1.5, t-test | |
| Normalization: | None | |
| Quality Cutoff: | None (Calls) | |
| Data Transformation: | Log Transformed | |

Show: 50  Sort By: Ratio  p Cutoff: 0.05

(178 results found) [1-50] [51-100]

| No. | Ratio | p-value | Identifier |
|---|---|---|---|
| 1 | ▲ 9.51 | 0.02415 | CK945739 |
| 2 | ▲ 8.73 | 0.00018 | CK777968 |
| 3 | ▲ 8.39 | 0.01017 | NM_173941 |
| 4 | ▲ 8.13 | 0.02899 | CK960499 |
| 5 | ▲ 7.32 | 0.03335 | CB530781 |
| 6 | ▲ 6.82 | 0.01256 | CK770622 |
| 7 | ▲ 6.35 | 0.00687 | CB456207 |
| 8 | ▲ 6.16 | 0.01641 | NM_174366 |
| 9 | ▲ 5.88 | 0.02380 | CB433489 |
| 10 | ▲ 5.73 | 0.00636 | BM288577 |
| 11 | ▲ 5.28 | 0.04252 | CK777675 |
| 12 | ▲ 5.26 | 0.04427 | CK955157 |
| 13 | ▲ 5.00 | 0.03645 | CB460780 |
| 14 | ▲ 4.90 | 0.04225 | CB461321 |
| 15 | ▲ 4.59 | 0.00458 | CK950701 |
| 16 | ▲ 4.54 | 0.02465 | CB443498 |
| 17 | ▲ 4.47 | 0.01648 | CK848208 |
| 18 | ▲ 4.40 | 0.02120 | BM031140 |
| 19 | ▲ 4.23 | 0.02478 | CK940917 |
| 20 | ▲ 4.19 | 0.03751 | CK771386 |
| 21 | ▲ 4.17 | 0.04972 | CB419688 |
| 22 | ▲ 4.10 | 0.01674 | BI680405 |
| 23 | ▲ 3.98 | 0.02600 | CK774949 |
| 24 | ▲ 3.92 | 0.00922 | CK971030 |
| 25 | ▲ 3.86 | 0.03593 | CK726556 |
| 26 | ▲ 3.70 | 0.03241 | NM_176674 |
| 27 | ▲ 3.60 | 0.02815 | CB433212 |
| 28 | ▲ 3.56 | 0.01118 | BM362372 |
| 29 | ▲ 3.54 | 0.04033 | CK776938 |
| 30 | ▲ 3.43 | 0.01886 | CB450623 |
| 31 | ▲ 3.38 | 0.04495 | NM_174437 |
| 32 | ▲ 3.36 | 0.03686 | CB432365 |
| 33 | ▲ 3.17 | 0.03882 | BE756263 |
| 34 | ▲ 2.99 | 0.02763 | CK945008 |
| 35 | ▲ 2.92 | 0.03043 | CK846935 |
| 36 | ▲ 2.91 | 0.01736 | BM433504 |
| 37 | ▲ 2.90 | 0.02889 | AV665367 |
| 38 | ▲ 2.85 | 0.04763 | BF440165 |
| 39 | ▲ 2.81 | 0.03809 | CB453859 |
| 40 | ▲ 2.77 | 0.00656 | NM_174609 |
| 41 | ▲ 2.74 | 0.02272 | NM_178109 |
| 42 | ▲ 2.71 | 0.01431 | NM_174180 |

TABLE 2

Preferred blood cell genes that are down-regulated genes in bloods from steers that are persistently infected with BVDV when compared to non-infected steers. In this illustration, CK848330, BP102272, AU278490, and BE723387 are preferred down-regulated markers in persistently infected steers.

Pairwise Analysis: BVDV Steers Con vs PI
[Reports: Ontology|KEGG|Scatter Plot]
[Results: Export|Save]

|  | Group 1 | Group 2 |
|---|---|---|
| Conditions: | Control | PI |
| Experiments: | 46038, 46039, 46040 | 46041, 46042 |
| Significance: | 1.5, t-test | |
| Normalization: | None | |
| Quality Cutoff: | None (Calls) | |
| Data Transformations: | Log Transformed | |

Show: 20   Sort By: Ratio   p Cutoff: 0.05
(116 results found) [1-20] [21-40]

| No. | Ratio | p-value | Identifier |
|---|---|---|---|
| 1 | ▼ 112.22 | 0.00018 | CK848330 |
| 2 | ▼ 69.02 | 0.00027 | BP102272 |
| 3 | ▼ 54.58 | 0.00006 | AU278490 |
| 4 | ▼ 9.38 | 0.00639 | BE723387 |
| 5 | ▼ 8.72 | 0.02468 | NM_174296 |
| 6 | ▼ 8.09 | 0.00259 | U73186 |
| 7 | ▼ 5.22 | 0.04616 | AW315720 |
| 8 | ▼ 4.37 | 0.01686 | CK977019 |
| 9 | ▼ 3.93 | 0.00579 | BF043343 |
| 10 | ▼ 3.49 | 0.01155 | CK777919 |
| 11 | ▼ 3.40 | 0.01676 | D13661 |
| 12 | ▼ 3.10 | 0.00948 | CK773758 |
| 13 | ▼ 3.09 | 0.02798 | CB535048 |
| 14 | ▼ 3.07 | 0.04211 | BP110719 |
| 15 | ▼ 2.79 | 0.02192 | CB451804 |
| 16 | ▼ 2.68 | 0.04161 | CK975615 |
| 17 | ▼ 2.65 | 0.02821 | D13656 |
| 18 | ▼ 2.61 | 0.03624 | CK769833 |
| 19 | ▼ 2.52 | 0.03126 | CK776879 |
| 20 | ▼ 2.46 | 0.03230 | AW481170 |

Figure 3:
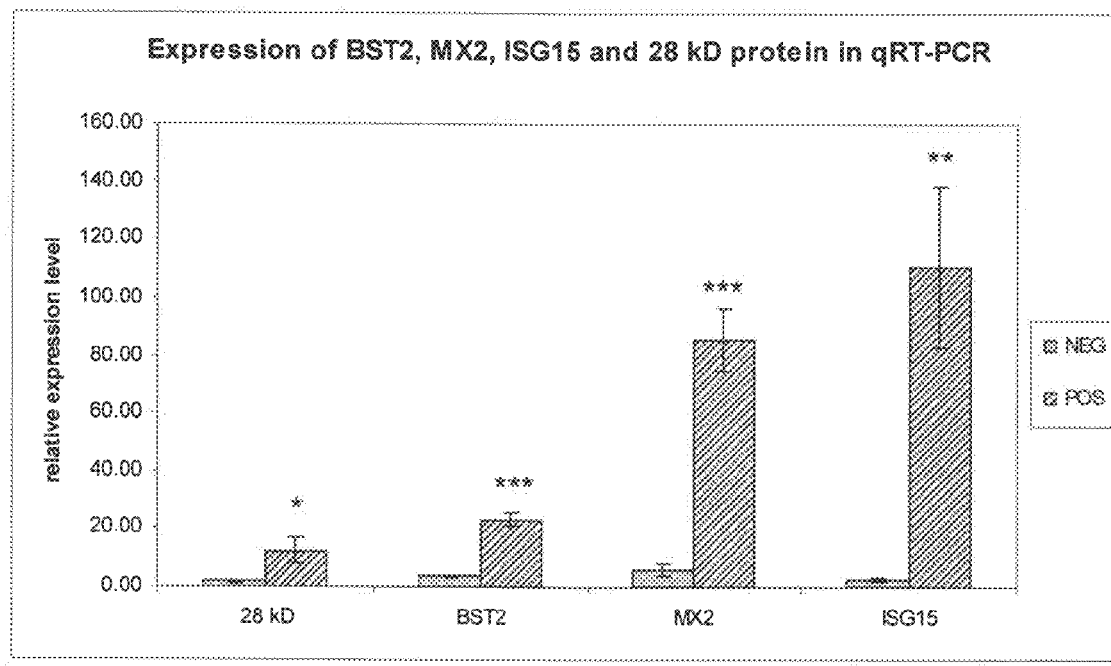
FIG. 3 is a graph showing select blood cell markers that are upregulated in bloods from persistently infected, when compared to non-infected steers using semi-quantitative Real Time PCR (GAPDH used as a control). The 28 kD (interferon induced 28 kD protein; CK771386), BST2 (bone marrow stromal cell surface antigen 2; CK846889), MX2 (myxovirus resistance 2; NM_173941) and ISG15 (Interferon stimulated 15 kDa; NM_174366) markers were all useful blood cell mRNA markers for distinguishing persistent viral infection (positive) when compared to control non-infected steers (negative). In this illustration, ISG15 and MX2 are preferred markers.

As can be seen by the data presented herein, persistent infection with BVDV causes up-regulation and down-regulation of genes in blood cells. Persistent infection with BVDV results in antiviral responses in blood cells. The results show induction of interferon-induced genes, chemokine-mediated immune responses and bone remodeling genes. Suppression of extracellular remodeling, adhesion and T-cell-mediated responses is also observed. One gene, called interferon stimulated gene 15 or ISG15 was confirmed to be up-regulated in bloods from PI
when compared to control vaccinated steers using blood cell mRNA and Real Time PCR approaches (FIGS. 2 and 3).

Example 2

Gene expression in white blood cells could differ in pregnant heifers carrying PI, TI or uninfected (control) fetuses, and this was examined. Non-vaccinated heifers were purchased, confirmed to be seronegative for BVDV and were placed on growing rations until they were old enough to be artificially inseminated and confirmed to be pregnant. Heifers were infected with noncytopathic BVDV2 on day 75 to generate PI fetuses, on day 175 to generate TI fetuses, or were not infected (n=6 heifers per treatment). Blood was collected on days 0, 37, 75, 78, 82, 90, 120, 160, 175, 178, 182 and 190 of gestation for RNA, serology and virology. Fetuses were delivered on d. 190 by C-section and necropsied. Maternal blood mRNA on day 190 of gestation was screened using the bovine Affymetrix gene chips.

BVDV infection in heifers and fetuses was confirmed using ELISA and qRT-PCR. Infected pregnant heifers were seropositive for BVDV by days 15-45 post infection. PI fetuses weighed less and were smaller with maldeveloped bone and muscle tissue (P<0.05) when compared to TI or UI fetuses. Screening of 24,000 transcripts on the bovine Affymetrix DNA chip using mRNA from blood cells of heifers on day 190 of pregnancy revealed 67 differentially expressed genes (1.5 fold or greater; P<0.05) based on infection status of the fetus: 32 genes in PI vs. TI, 26 genes in PI vs. control and 47 genes in TI vs. control. These genes were classified based on ontology analysis in primary categories of immune response, antigen presentation, inflammatory response, chemotaxis, protein folding and modification, transport, and defense response to bacteria. Specific genes that are differentially expressed are described in Tables 3-9.

TABLE 3

Preferred upregulated blood cell markers in heifers carrying persistently virally infected, when compared to non-infected fetuses (Control vs. PI: upregulated in PI).

|  | Group 1 | Group 2 |
|---|---|---|
| Conditions: | Control | Persistently Infected |
| Experiments: | 44009, 44010, 44011 | 44012, 44013, 44014 |
| Significance: | 1.5, t-test | |
| Normalization: | None | |
| Quality Cutoff: | None (Calls) | |
| Data Transformation: | Log Transformed | |

Show: 20   Sort By: Ratio   p Cutoff: 0.05
(35 results found) [1-20] [21-35]

| No. | Ratio | p-value | Identifier |
|---|---|---|---|
| 1 | ▲ 2.42 | 0.04287 | CK977019 |
| 2 | ▲ 2.16 | 0.01372 | CA923353 |
| 3 | ▲ 1.96 | 0.01319 | CB461169 |
| 4 | ▲ 1.94 | 0.01118 | CB445920 |
| 5 | ▲ 1.86 | 0.00314 | NM_174324 |
| 6 | ▲ 1.85 | 0.02151 | CK778261 |
| 7 | ▲ 1.75 | 0.04560 | BF042221 |
| 8 | ▲ 1.72 | 0.00155 | CB463330 |
| 9 | ▲ 1.70 | 0.04465 | CK979795 |
| 10 | ▲ 1.69 | 0.02380 | CK960396 |
| 11 | ▲ 1.68 | 0.02461 | CK957227 |
| 12 | ▲ 1.68 | 0.03122 | CK846626 |
| 13 | ▲ 1.67 | 0.03347 | CB443446 |
| 14 | ▲ 1.66 | 0.00532 | CK837929 |
| 15 | ▲ 1.64 | 0.03202 | CB447702 |
| 16 | ▲ 1.61 | 0.02709 | CK847647 |
| 17 | ▲ 1.61 | 0.03926 | CK774460 |
| 18 | ▲ 1.59 | 0.03385 | BI682736 |
| 19 | ▲ 1.59 | 0.04521 | CK972892 |
| 20 | ▲ 1.58 | 0.03836 | CB535138 |

TABLE 4

Preferred downregulated blood cell markers in heifers carrying persistently virally infected, when compared to non-infected fetuses (Control vs. PI: downregulated in PI).

|  | Group 1 | Group 2 |
|---|---|---|
| Conditions: | Control | Persistently Infected |
| Experiments: | 44009, 44010, 44011 | 44012, 44013, 44014 |
| Significance: | 1.5, t-test | |
| Normalization: | None | |
| Quality Cutoff: | None (Calls) | |
| Data Transformation: | Log Transformed | |

TABLE 4-continued

Preferred downregulated blood cell markers in heifers carrying persistently virally infected, when compared to non-infected fetuses (Control vs. PI: downregulated in PI).

Show: 20  Sort By: Ratio  p Cutoff: 0.05
(15 results found) [1-15]

| No. | Ratio | p-value | Identifier |
|---|---|---|---|
| 1 | ▼ 2.82 | 0.01126 | NM_175827 |
| 2 | ▼ 2.69 | 0.03202 | CB425639 |
| 3 | ▼ 2.24 | 0.04464 | NM_174511 |
| 4 | ▼ 2.22 | 0.00573 | CB534503 |
| 5 | ▼ 2.07 | 0.02014 | CK945488 |
| 6 | ▼ 2.03 | 0.02292 | CB461397 |
| 7 | ▼ 2.01 | 0.02229 | BM251259 |
| 8 | ▼ 1.96 | 0.04149 | CK775256 |
| 9 | ▼ 1.91 | 0.04699 | CB463807 |
| 10 | ▼ 1.77 | 0.03397 | CK771825 |
| 11 | ▼ 1.73 | 0.02399 | CF930613 |
| 12 | ▼ 1.71 | 0.04130 | CB171451 |
| 13 | ▼ 1.70 | 0.02006 | CF763999 |
| 14 | ▼ 1.59 | 0.03949 | CK962640 |
| 15 | ▼ 1.57 | 0.02055 | BE723387 |

TABLE 5

Preferred upregulated blood cell markers in heifers carrying transiently virally infected, when compared to non-infected fetuses (Control vs. TI: upregulated in TI).

|  | Group 1 | Group 2 |
|---|---|---|
| Conditions: | Control | Transiently Infected |
| Experiments: | 44009, 44010, 44011 | 44008, 44015, 44016 |
| Significance: | 1.5, t-test | |
| Normalization: | None | |
| Quality Cutoff: | None (Calls) | |
| Data Transformation: | Log Transformed | |

Show: 50  Sort By: Ratio  p Cutoff: 0.05
(48 results found) [1-48]

| No. | Ratio | p-value | Identifier |
|---|---|---|---|
| 1 | ▲ 7.55 | 0.00024 | CK960499 |
| 2 | ▲ 5.03 | 0.00015 | CB464371 |
| 3 | ▲ 3.57 | 0.00411 | NM_174366 |
| 4 | ▲ 2.91 | 0.00075 | CB433489 |
| 5 | ▲ 2.89 | 0.00318 | CK955157 |
| 6 | ▲ 2.88 | 0.00351 | CB460780 |
| 7 | ▲ 2.86 | 0.03887 | CB530781 |
| 8 | ▲ 2.63 | 0.01280 | NM_173941 |
| 9 | ▲ 2.61 | 0.00228 | CK777675 |
| 10 | ▲ 2.15 | 0.01295 | CB432365 |
| 11 | ▲ 2.07 | 0.00093 | CB445920 |
| 12 | ▲ 2.03 | 0.03937 | CK980927 |
| 13 | ▲ 2.00 | 0.04814 | CB536841 |
| 14 | ▲ 1.96 | 0.03946 | AF016394 |
| 15 | ▲ 1.95 | 0.00706 | CK848208 |
| 16 | ▲ 1.94 | 0.00547 | CK848475 |
| 17 | ▲ 1.92 | 0.01884 | BE666861 |
| 18 | ▲ 1.87 | 0.01922 | CB430886 |
| 19 | ▲ 1.87 | 0.01703 | BM031140 |
| 20 | ▲ 1.82 | 0.00650 | CK971030 |
| 21 | ▲ 1.80 | 0.00386 | CK776302 |
| 22 | ▲ 1.79 | 0.02243 | CK848830 |
| 23 | ▲ 1.78 | 0.02470 | CK777062 |
| 24 | ▲ 1.74 | 0.03253 | BI680405 |
| 25 | ▲ 1.71 | 0.04939 | CB536836 |
| 26 | ▲ 1.69 | 0.03453 | BE668756 |
| 27 | ▲ 1.68 | 0.00238 | NM_174601 |
| 28 | ▲ 1.66 | 0.00635 | CB535112 |
| 29 | ▲ 1.65 | 0.01121 | CK774420 |

TABLE 5-continued

Preferred upregulated blood cell markers in heifers carrying transiently virally infected, when compared to non-infected fetuses (Control vs. TI: upregulated in TI).

| No. | Ratio | p-value | Identifier |
|---|---|---|---|
| 30 | ▲ 1.65 | 0.04721 | BE753440 |
| 31 | ▲ 1.64 | 0.00825 | CB465021 |
| 32 | ▲ 1.61 | 0.02079 | CK776907 |
| 33 | ▲ 1.61 | 0.02346 | CB422521 |
| 34 | ▲ 1.60 | 0.04267 | CK846935 |
| 35 | ▲ 1.60 | 0.04557 | BM087443 |
| 36 | ▲ 1.60 | 0.03689 | CK774101 |
| 37 | ▲ 1.60 | 0.01013 | CK968996 |
| 38 | ▲ 1.60 | 0.00120 | CB463330 |
| 39 | ▲ 1.58 | 0.01549 | NM_174081 |
| 40 | ▲ 1.57 | 0.04647 | AW426236 |
| 41 | ▲ 1.57 | 0.02922 | CB172358 |
| 42 | ▲ 1.56 | 0.00399 | CB168658 |
| 43 | ▲ 1.56 | 0.02344 | CB441353 |
| 44 | ▲ 1.55 | 0.03157 | CK769183 |
| 45 | ▲ 1.54 | 0.01408 | CK966858 |
| 46 | ▲ 1.53 | 0.01227 | CK770915 |
| 47 | ▲ 1.52 | 0.03676 | CB464450 |
| 48 | ▲ 1.51 | 0.01286 | CK969631 |

TABLE 6

Preferred downregulated blood cell markers in heifers carrying transiently virally infected, when compared to non-infected fetuses (Control vs. TI: downregulated in TI).

|  | Group 1 | Group 2 |
|---|---|---|
| Conditions: | Control | Transiently Infected |
| Experiments: | 44009, 44010, 44011 | 44008, 44015, 44016 |
| Significance: | 1.5, t-test | |
| Normalization: | None | |
| Quality Cutoff: | None (Calls) | |
| Data Transformation: | Log Transformed | |

Show: 50  Sort By: Ratio  p Cutoff: 0.05
(41 results found) [1-41]

| No. | Ratio | p-value | Identifier |
|---|---|---|---|
| 1 | ▼ 487.07 | 0.00000 | CB444277 |
| 2 | ▼ 11.06 | 0.00371 | AB008573 |
| 3 | ▼ 3.89 | 0.00475 | CB433789 |
| 4 | ▼ 2.36 | 0.04120 | AV609250 |
| 5 | ▼ 2.34 | 0.03538 | CK776354 |
| 6 | ▼ 2.17 | 0.00884 | BE752683 |
| 7 | ▼ 2.13 | 0.01796 | CK972404 |
| 8 | ▼ 2.04 | 0.02469 | CB423642 |
| 9 | ▼ 2.00 | 0.01152 | CB430069 |
| 10 | ▼ 1.98 | 0.04868 | BE487674 |
| 11 | ▼ 1.93 | 0.00865 | CB534503 |
| 12 | ▼ 1.92 | 0.00788 | CK775223 |
| 13 | ▼ 1.90 | 0.03876 | CK847570 |
| 14 | ▼ 1.88 | 0.01828 | M37974 |
| 15 | ▼ 1.88 | 0.00863 | CB456756 |
| 16 | ▼ 1.87 | 0.04989 | NM_175827 |
| 17 | ▼ 1.86 | 0.03720 | BP107527 |
| 18 | ▼ 1.81 | 0.01772 | CK945488 |
| 19 | ▼ 1.79 | 0.01237 | CB467996 |
| 20 | ▼ 1.72 | 0.02167 | CB461397 |
| 21 | ▼ 1.71 | 0.00526 | CB534327 |
| 22 | ▼ 1.71 | 0.02438 | CK773609 |
| 23 | ▼ 1.69 | 0.04044 | CK846542 |
| 24 | ▼ 1.66 | 0.03462 | CB417623 |
| 25 | ▼ 1.65 | 0.01097 | CK953227 |
| 26 | ▼ 1.65 | 0.01448 | CK845887 |
| 27 | ▼ 1.64 | 0.04173 | D90419 |
| 28 | ▼ 1.62 | 0.04086 | CB431455 |
| 29 | ▼ 1.61 | 0.04302 | CB419791 |
| 30 | ▼ 1.60 | 0.00548 | CK846165 |
| 31 | ▼ 1.60 | 0.03304 | CK838029 |
| 32 | ▼ 1.59 | 0.03900 | CB435377 |

TABLE 6-continued

Preferred downregulated blood cell markers in heifers carrying transiently virally infected, when compared to non-infected fetuses (Control vs. TI: downregulated in TI).

| | | | |
|---|---|---|---|
| 33 | ▼ 1.58 | 0.04870 | CB428714 |
| 34 | ▼ 1.58 | 0.03882 | CK966877 |
| 35 | ▼ 1.58 | 0.00735 | CB531127 |
| 36 | ▼ 1.57 | 0.00519 | CB460964 |
| 37 | ▼ 1.56 | 0.04297 | CB434065 |
| 38 | ▼ 1.54 | 0.03573 | CK849477 |
| 39 | ▼ 1.54 | 0.00116 | BP103941 |
| 40 | ▼ 1.53 | 0.02401 | NM_175716 |
| 41 | ▼ 1.52 | 0.01837 | AW478035 |

TABLE 7

Preferred upregulated blood cell markers in heifers carrying persistently virally infected when compared to transiently virally infected fetuses (TI vs. PI: upregulated in PI).

| | Group 1 | Group 2 |
|---|---|---|
| Conditions: | Transiently Infected | Persistently Infected |
| Experiments: | 44008, 44015, 44016 | 44012, 44013, 44014 |
| Significance: | 1.5, t-test | |
| Normalization: | None | |
| Quality Cutoff: | None (Calls) | |
| Data Transformation: | Log Transformed | |

Show: 50   Sort By: Ratio   p Cutoff: 0.05
(35 results found) [1-35]

| No. | Ratio | p-value | Identifier |
|---|---|---|---|
| 1 | ▲ 9.95 | 0.00366 | AB008573 |
| 2 | ▲ 3.82 | 0.02074 | CB433789 |
| 3 | ▲ 2.25 | 0.01319 | CB530181 |
| 4 | ▲ 2.13 | 0.01153 | M37974 |
| 5 | ▲ 2.05 | 0.02681 | CB420023 |
| 6 | ▲ 2.05 | 0.00024 | CB461169 |
| 7 | ▲ 1.93 | 0.01489 | CB460964 |
| 8 | ▲ 1.89 | 0.00831 | CB534327 |
| 9 | ▲ 1.82 | 0.01041 | CK945043 |
| 10 | ▲ 1.77 | 0.03692 | CB423642 |
| 11 | ▲ 1.77 | 0.03010 | CB443498 |
| 12 | ▲ 1.77 | 0.04638 | CB458416 |
| 13 | ▲ 1.76 | 0.03425 | NM_174373 |
| 14 | ▲ 1.76 | 0.01755 | CB435377 |
| 15 | ▲ 1.75 | 0.04017 | BE758040 |
| 16 | ▲ 1.69 | 0.04108 | AY298812 |
| 17 | ▲ 1.67 | 0.00189 | CK953227 |
| 18 | ▲ 1.66 | 0.03204 | BM285504 |
| 19 | ▲ 1.66 | 0.01417 | CB439678 |
| 20 | ▲ 1.65 | 0.02078 | AJ235267 |
| 21 | ▲ 1.64 | 0.01508 | AV615989 |
| 22 | ▲ 1.62 | 0.04868 | D90132 |

TABLE 7-continued

Preferred upregulated blood cell markers in heifers carrying persistently virally infected when compared to transiently virally infected fetuses (TI vs. PI: upregulated in PI).

| | | | |
|---|---|---|---|
| 23 | ▲ 1.60 | 0.04572 | CK771797 |
| 24 | ▲ 1.60 | 0.04743 | CB424072 |
| 25 | ▲ 1.60 | 0.01012 | CB420282 |
| 26 | ▲ 1.59 | 0.04919 | CK946910 |
| 27 | ▲ 1.57 | 0.04409 | BE237119 |
| 28 | ▲ 1.56 | 0.04897 | D90013 |
| 29 | ▲ 1.55 | 0.04232 | AV604293 |
| 30 | ▲ 1.54 | 0.03887 | CK727097 |
| 31 | ▲ 1.53 | 0.01790 | BE723538 |
| 32 | ▲ 1.53 | 0.01296 | CK778261 |
| 33 | ▲ 1.52 | 0.02640 | AJ006574 |
| 34 | ▲ 1.52 | 0.01496 | CK847994 |
| 35 | ▲ 1.52 | 0.03625 | BM253121 |

TABLE 8

Preferred downregulated blood cell markers in heifers carrying persistently virally infected when compared to transiently virally infected fetuses (TI vs. PI: downregulated in PI).

| | Group 1 | Group 2 |
|---|---|---|
| Conditions: | Transiently Infected | Persistently Infected |
| Experiments: | 44008, 44015, 44016 | 44012, 44013, 44014 |
| Significance: | 1.5, t-test | |
| Normalization: | None | |
| Quality Cutoff: | None (Calls) | |
| Data Transformation: | Log Transformed | |

Show: 20   Sort By: Ratio   p Cutoff: 0.05
(16 results found) [1-16]

| No. | Ratio | p-value | Identifier |
|---|---|---|---|
| 1 | ▼ 3.87 | 0.04453 | CK960499 |
| 2 | ▼ 2.36 | 0.01971 | AW658483 |
| 3 | ▼ 2.33 | 0.01380 | NM_174366 |
| 4 | ▼ 2.29 | 0.00929 | CK771750 |
| 5 | ▼ 2.24 | 0.02029 | CK955157 |
| 6 | ▼ 2.17 | 0.01340 | CB460780 |
| 7 | ▼ 2.13 | 0.01958 | CK777675 |
| 8 | ▼ 1.94 | 0.01880 | CB433489 |
| 9 | ▼ 1.73 | 0.03188 | CK848208 |
| 10 | ▼ 1.67 | 0.04677 | CB432365 |
| 11 | ▼ 1.63 | 0.04720 | CK972160 |
| 12 | ▼ 1.57 | 0.03785 | AB008649 |
| 13 | ▼ 1.56 | 0.04230 | CB459838 |
| 14 | ▼ 1.56 | 0.04946 | BF230904 |
| 15 | ▼ 1.54 | 0.04682 | BF041863 |
| 16 | ▼ 1.53 | 0.02518 | CB422521 |

TABLE 9

Figure 4:
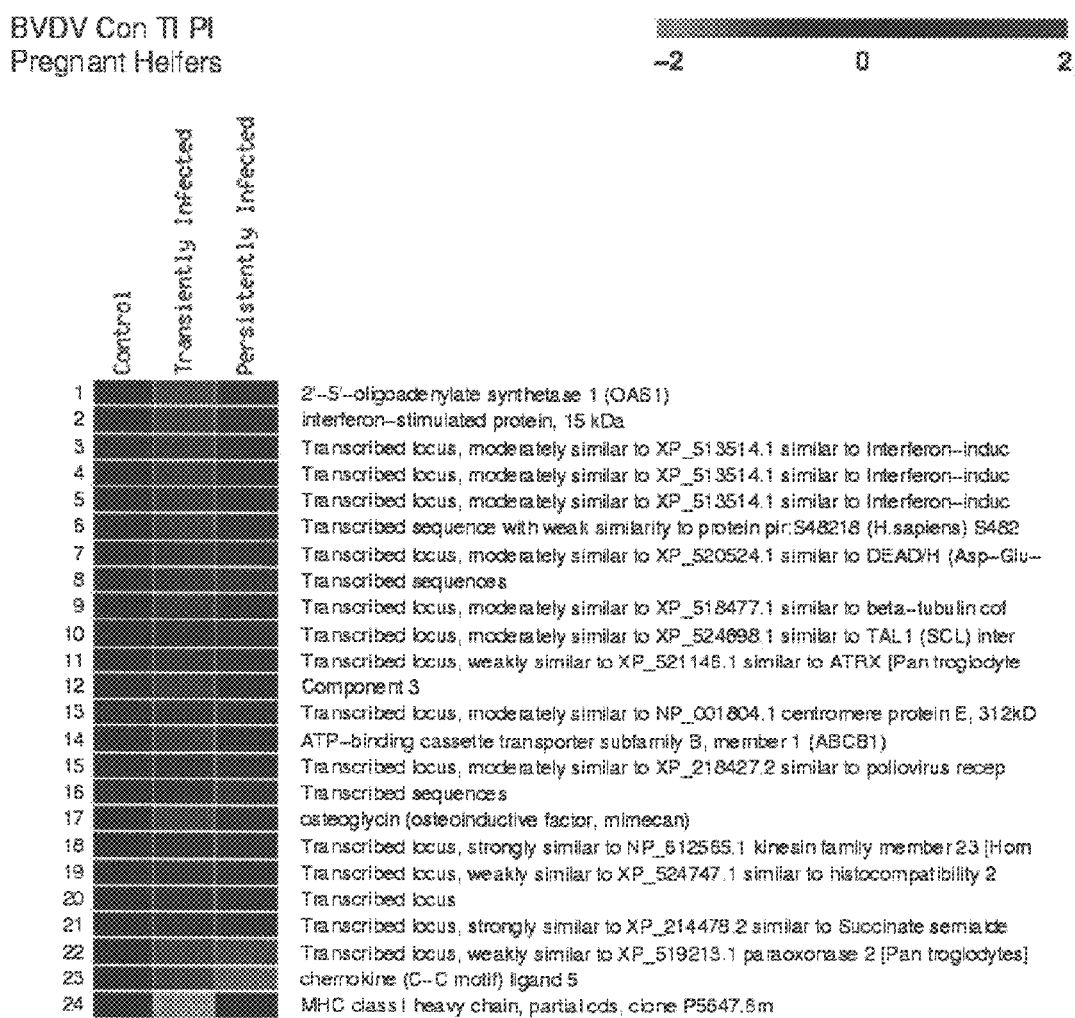
FIG. 4 is a heat plot illustrating three-Way ANOVA analysis of blood cell gene expression from mothers carrying control vs. TI vs. PI virally infected fetuses on day 190 of gestation described in Table 9. This analysis represents a fold change of 1.5 fold or greater with P<0.01. Table 9 provides the actual P values for each comparison and a more complete description of each gene.

Analysis of blood gene expression using a three-way ANOVA in heifers carrying control vs. TI vs. PI fetuses. Analysis represents the top 24 genes that were differentially expressed in at least one of the treatment groups. The value in the ANOVA column represents the P value when determining if one of the three means differs. Please refer to the heat plot in FIG. 4 for an illustration of these data.

| ANOVA | Control Mean | TI Mean | PI Mean | Control SEM 1 | PI SEM 2 | TI SEM 3 | Gene Identifier |
|---|---|---|---|---|---|---|---|
| 0.006032 | 8.00309 | 10.9193 | 8.96783 | 0.188264 | 0.138741 | 0.660686 | CK960499 |
| 0.003154 | 10.115 | 11.9521 | 10.7336 | 0.256113 | 0.176554 | 0.231053 | NM_174366 |
| 0.003028 | 6.90223 | 8.43096 | 7.26529 | 0.101244 | 0.219103 | 0.222812 | CK955157 |
| 0.003101 | 8.16371 | 9.68817 | 8.57334 | 0.191589 | 0.15614 | 0.212549 | CB460780 |
| 0.003419 | 6.74951 | 8.13573 | 7.04487 | 0.104431 | 0.170809 | 0.23341 | CK777675 |
| 0.001684 | 7.22418 | 8.76654 | 7.80757 | 0.137263 | 0.093874 | 0.232921 | CB433489 |
| 0.008299 | 8.21365 | 9.31672 | 8.57504 | 0.110353 | 0.233574 | 0.116391 | CB432365 |

TABLE 9-continued

Analysis of blood gene expression using a three-way ANOVA in heifers carrying control vs. TI vs. PI fetuses. Analysis represents the top 24 genes that were differentially expressed in at least one of the treatment groups. The value in the ANOVA column represents the P value when determining if one of the three means differs. Please refer to the heat plot in FIG. 4 for an illustration of these data.

| ANOVA | Control Mean | TI Mean | PI Mean | Control SEM 1 | PI SEM 2 | TI SEM 3 | Gene Identifier |
|---|---|---|---|---|---|---|---|
| 0.00315  | 8.16901  | 9.22019  | 9.12652 | 0.048718 | 0.109524 | 0.209197 | CB445920 |
| 0.002321 | 9.87333  | 9.15127  | 9.88773 | 0.12978  | 0.095443 | 0.033274 | CK953227 |
| 0.009597 | 5.57083  | 5.66441  | 6.21629 | 0.161879 | 0.077099 | 0.026107 | CK971667 |
| 0.000202 | 8.26679  | 7.64432  | 8.09498 | 0.036558 | 0.065628 | 0.028333 | BP103941 |
| 0.005323 | 6.91205  | 6.14205  | 7.06362 | 0.125015 | 0.061868 | 0.179441 | CB534327 |
| 0.003199 | 5.25886  | 5.54151  | 5.89927 | 0.099747 | 0.072327 | 0.051183 | CB443429 |
| 0.00661  | 7.76552  | 7.11499  | 8.06201 | 0.028002 | 0.114012 | 0.201076 | CB460964 |
| 0.006969 | 5.88815  | 6.50156  | 6.25403 | 0.108627 | 0.090517 | 0.04993  | CK770915 |
| 0.002739 | 4.50737  | 4.44439  | 5.47889 | 0.218718 | 0.048776 | 0.067073 | CB461169 |
| 0.003618 | 7.02454  | 6.11085  | 7.19863 | 0.035911 | 0.234515 | 0.075039 | M37974 |
| 0.007258 | 7.29919  | 7.80462  | 7.90756 | 0.145198 | 0.007311 | 0.065739 | CK950633 |
| 0.006348 | 9.11153  | 10.0777  | 9.28636 | 0.01677  | 0.189202 | 0.15531  | CK848208 |
| 0.00656  | 4.52089  | 5.16352  | 5.09881 | 0.106526 | 0.017049 | 0.016545 | CB168658 |
| 0.0004   | 5.60571  | 6.28826  | 6.3913  | 0.053773 | 0.063446 | 0.087055 | CB463330 |
| 0.002006 | 4.94446  | 3.99497  | 3.79603 | 0.173649 | 0.094759 | 0.123417 | CB534503 |
| 0.009713 | 10.8281  | 9.92825  | 9.33185 | 0.253205 | 0.201907 | 0.221374 | NM_175827 |
| 0.00064  | 11.0449  | 7.57803  | 10.8921 | 0.258042 | 0.509224 | 0.189688 | AB008573 |

Early detection of persistently infected calves is the best method of controlling and eradicating BVDV from infected herds. Current diagnostic tests for BVDV include skin biopsies and serology which do not distinguish acutely infected animals from persistently animals. These PI animals go undetected and continue to propagate virus within the herd.

Current methods of detection also have a high rate of false negatives due to the fact that they are based on mutating viral antigens. Most importantly, current tests cannot detect a pregnant cow/heifer which is carrying a persistently infected calf.

The present invention describes a method whereby BVDV can be detected in acutely infected calves, persistently infected calves as well as cows or heifers carrying an infected fetus through the identification of differentially expressed surrogate markers described in Tables 1-9 and 12. Surrogate markers can exist as mRNA or protein antigens and allow differentiation of type of BVDV infection. By the methods listed previously persistently infected (PI) calves can be differentiated from acutely infected calves and acutely infected calves can be distinguished from non-infected calves. Heifers and cows carrying PI fetuses can also be distinguished from heifers/cows carrying transiently infected fetuses and cows/heifers carrying PI or TI fetuses can be distinguished from cows/heifers carrying non-infected (normal) calves. The same markers can be used to create therapeutics for treating secondary effects of viral disease and monitoring the antiviral response in infected cattle. The global approach presented herein will aid the prevention, diagnosis, control and treatment of cattle infected with BVDV as well as other RNA viruses.

Example 3

As described hereinabove, infection with BVDV, the single-stranded RNA virus in the genus *Pestivirus* (family Flaviviridae), causes viral diarrhea in herds of cattle and leads to significant economical loss in the agriculture of the USA and other countries (1). It is clear that detection and removal of pregnant cows carrying PI fetuses would benefit control programs. Once a positive animal is identified, it could be isolated for further tests. Also, if these markers are specific for virus and are not increased in a bacterial infection, then treatments such as antibiotics could be better controlled and administered.

To this end, a maternal immune cell marker has been identified that is significantly down regulated for ninety days following BVDV infection of the PI fetus. This marker was identified following microarray analysis of maternal bloods described in Example 2, with the exception of the day of pregnancy that was examined. Bloods were collected on day 160 for this analysis. The maternal cell marker has utility in the identification and hence subsequent elimination of these cattle from the herd. The differential expression of chemokines and chemokine receptors in jugular blood from mothers (cows and heifers) that are carrying PI fetuses offer the ability to identify infected animals.

The following materials and methods help facilitate practice of the embodiments of the invention.

Animals

All experiments using cattle were approved by the Animal Care and Use Committees at the University of Wyoming and Colorado State University. Eighteen weaned Hereford heifers not vaccinated against BVDV were screened for anti-BVDV antibodies twice, and were found to be seronegative for BVDV1 and BVDV2 in standard serum neutralization assay. No BVDV virus was found in ear notch extracts using the commercial ELISA (IDEXX Laboratories, Westbrook, Me., USA). Prior to the start of the experiment all heifers were confirmed to be seronegative to bovine herpesvirus type 1 and to bovine respiratory syncytial virus. Estrous cycles were synchronized at about 12 months of age, and the heifers were artificially inseminated and assigned to one of the three viral treatment groups (n=6).

Viral Challenge

The heifers (n=6 per each group) were inoculated with ncp BVDV2 strain 96B2222 (61) on day 75 (PI group), day 175 (TI group), or kept uninfected (control) to generate PI, TI or control uninfected fetuses, respectively, as previously described (53). Briefly, each heifer of the PI and TI groups received 2 ml of viral stock aliquot at 4.4 log 10 TCID50/ml intranasally. Blood samples were drawn for RNA isolation on multiple days of infection. Fetuses were recovered by cesarean section on day 190 of gestation.

RNA Isolation for Gene Microarray and RT-PCR Blood samples for genome wide microarray analysis were collected into EDTA containing vacutainers. Red blood cells were lysed with erythrocyte lysis buffer to prevent contamination of RNA with abundant red blood cell proteins; remaining total white blood cells were collected by centrifugation and processed to yield total RNA using QIA shredder spin column and QIAmp procedures and reagents (Qiagen Inc, Valencia, Calif., USA) following the manufacturer's instructions. After DNase treatment and clean up using QIAmp columns RNA was eluted in 30 µl of RNAse-free water and used for the genome wide microarray analysis by hybridization and screening of the Affymetrix bovine DNA chip at the Montana State University INBRE Functional Genomics Core Facility (Bozeman, Mont., USA). Genome wide microarray analysis on day 160 of gestation was completed on blood samples of 4 control heifers and 5 blood samples of heifers of the PI group. Three heifers from each experimental group (TI, PI and control) were used for the genome wide microarray analysis on day 160 of gestation. Blood samples from heifers for both microarray experiments were selected at random from groups of six per treatment. For microarray screens, time points of infection were chosen in a way that would allow study of the pathways in blood cells of pregnant heifers affected by the presence of a PI fetus after clearance of maternal infection (day 160).

RNA concentrations and purity were determined by measuring absorbances at 260 nm and 280 nm on a GeneQuant II spectrophotometer (Pharmacia Biotech). RNA quality was evaluated using the RNA 6000 NanoChip assay on a 2100 Bioanalyzer (Agilent Technologies, Palo Alto, Calif., USA). RNA samples with 18S/28S ratio of 1.7 and A260/A280 ratio of 1.8+/−0.2 were used for the arrays. Total RNA was amplified, biotin-labeled and hybridized to Affymetrix GeneChip Bovine Genome Arrays (#900562, Affymetrix, Santa Clara, Calif., USA) as described in the users' manual (Affymetrix GeneChip Expression Analysis Technical Manual, November 2004), using the GeneChip Expression 3′ Amplification One-Cycle Target Labeling and Control Reagents kit (#900493). Briefly, total RNA (approximately 3.5 ug per sample) was reverse transcribed to cDNA using a T7-oligo (dT) primer. Following second-strand cDNA synthesis, the double-stranded cDNA was purified as a template for the subsequent in vitro transcription (IVT) reaction. Linearly amplified biotin-labeled complementary RNA (cRNA) was synthesized in the presence of a biotinylated nucleotide analog/ribonucleic acid mix. The labeled cRNA was purified, fragmented, and hybridized to the arrays at 45° C. for 16 hours with constant rotational mixing at 60 rpm. Washing and staining of the arrays was performed using the Affymetrix GeneChip Fluidics Station 450. Arrays were scanned using an Affymetrix GeneChip Scanner 7G and GCOS software version 1.4. The Bovine Genome genechip contains 24,027 probe sets representing over 23,000 transcripts. The array was designed based on content from Bovine UniGene Build 57 (2004) and GenBank mRNAs. Each probe set on the array is represented by 11 pairs of perfect match and mismatch probes.

Total RNA for semi-quantitative real time PCR (qRT-PCR) was isolated from samples of whole blood preserved with Tri reagent BD for Blood Derivatives (Sigma-Aldrich, Saint Louis, Mo., USA). Briefly, total RNA was isolated with Tri reagent BD and purified using RNeasy MinElute Cleanup Kit (Qiagen Inc, Valencia, Calif., USA). Synthesis of cDNA was performed using iScript cDNA synthesis kit (Bio-Rad, Hercules, Calif., USA). Synthesized cDNA was diluted 5-fold with RNAse free water and used for the qRT-PCR reaction.

Microarray Analysis

1. Overview of Genome Wide Microarray Analysis

This analysis is distinct from the approach used in the prior examples. The pipeline (i.e., data-normalization-inference-computational validation-functional annotation-conversion to human homologs-pathway representation analysis-FDR-computational and/or experimental validation-prospective biomarkers and therapeutic targets) includes most of the standard analysis steps, but has a few important differences to maximize the advantage of pathway analysis. Standard normalization procedure was used. Inference of potentially differential genes was performed using relaxed criteria. The genes important for understanding the biological processes involved in immune response were selected not solely by the difference in signal emitted by microarray probes. Instead, the "group behavior" of genes was concentrated on, their ability to interact and pre-existing annotation placing the genes into the same biological pathway and linking to the same cellular function. Thus, the inference was done with very liberal selection criteria and not adjusted for multiple testing. A large list of potentially differential genes were selected, which may contain a large number of false-positives. Biological pathways were then selected, molecular function and Gene Ontology (GO) terms, which were over-represented in the initial intensity-based list. The benefits of using pathways and ontological analyses of microarray data are well known in the art. The significance of biological pathways was estimated through a variation of Fisher's exact test as implemented in GeneGo Metacore and adjusted for multiple testing using Benjamini-Hochberg FDR analysis (a build-in function of GeneGo Metacore software). Single genes that did not map into any statistically significant pathway (i.e. missing all regulators, downstream targets, ligands and other components necessary for a functional molecular mechanism) may still be considered significant if reproducible and independently validated in additional experiments. This approach relies on collective effects of the groups of genes interlinked by functional relationships, which may be inapplicable to some genes lacking information on function, regulation and interaction with other genes. Specific biomarkers are selected among the members of statistically significant pathways and independently verified by additional RT-PCR experiments.

2. Normalization

The data were normalized using a quantile algorithm, applying C++ software for normalization.

3. Preliminary Selection of Differentially Expressed Genes

A set of differentially expressed genes was selected using University of Pittsburgh Gene Expression Data Analysis suite (GEDA, available on the world wide web at: bioinformatics.upmc.edu/GE2/GEDA.html). For selection, the standard J5 metric with threshold 4 and optional 4 iteration of Jackknife procedure was applied to reduce the number of false-positive differential genes. Both J5 metric and threshold parameter are standard pre-set values recommended by the developers. No attempts were made to estimate the confidence level of individual genes and J5 was used, not as a statistical test, but as a selection procedure providing a shortlist of genes deviating from the expected average value and enriched with differential genes. Application of selection procedures biased away from highly expressed genes may reveal truly differential genes, but fewer suitable biomarker candidates. DAVID web-based tools were applied to perform functional annotation of all potentially differential genes selected by GEDA. The complete annotated lists for analyzed data sets are given in the GEO database (provisional accession number GSE11835).

4. Conversion to the Nearest Human Homolog

Current versions of commercial pathway analysis software do not support bovine transcriptome data. It is presumed that human biological pathways are sufficiently similar to those of *Bos taurus*. Affymetrix support website (on the world wide web at: affymetrix.com/support) offers tables delineating the nearest homologs between target sequences used to derive sets of probes for different expression arrays. The table of nearest homologs between bovine and human expression arrays was used to convert the bovine list of genes to the list of human homologous genes. Since expression arrays are biased towards less evolutionary conservative 3' UTR of expressed genes the conversion procedure looses a considerable number of genes lacking strong similarity between corresponding human and bovine target sequences. However, the remaining list of genes was sufficient to identify statistically overrepresented pathways.

5. Functional Annotation and Pathway Analysis

Analysis of biological pathways was performed using MetaCore software (GeneGo Inc.) licensed through the Colorado State University Center for Bioinformatics and free DAVID tools.

qRT-PCR Procedure and Primers qRT-PCR reactions were performed with IQ SYBR green supermix (Bio-Rad, USA) on the LightCycler480 (Roche, Basel, Switzerland) using the 384-well plate format. qRT-PCR reaction, performed in duplicate, contained 2 µl of cDNA, 5 µl of Supermix, and 1.5 µl of 7.5 nM solution of each primer. The qRT-PCR reaction was conducted at 95° C. for 3 min, followed by 40 cycles of 95° C. for 30 sec, 61° C. for 30 sec and 72° C. for 15 sec. Upon completion of qRT-PCR amplification, melting curve analysis was performed to evaluate the quality of amplification. The qRT-PCR results were analyzed with the Comparative Ct ($\Delta\Delta$Ct) method, and data were presented as a relative expression. The housekeeping gene glyceraldehyde-3-phosphate dehydrogenase (GAPDH) was used as endogenous control gene for normalization of data. Target genes and primers for qRT-PCR are:

```
CBL (AV594776)
F: CGGGTCACATACACATCAA      (SEQ ID NO: 1)
R: AGGAGGCGGTTGTCATACAC     (SEQ ID NO: 2)

CD45 (BC148881)
F: ACGGAGATCAGGATCAAAC      (SEQ ID NO: 3)
R: AGTCTCATCCCTGGGACCTT     (SEQ ID NO: 4)

CXCR4 (NM_174301.2)
F: AAGGCTCAGAAGCGCAAG       (SEQ ID NO: 5)
R: GAGTCGATGCTGATCCCAAT     (SEQ ID NO: 6)

GAPDH (AV610889)
F: TGACCCCTTCATTGACCTTC     (SEQ ID NO: 7)
R: CGTTCTCTGCCTTGACTGTG     (SEQ ID NO: 8)

IFIT-2 (BT025389)
F: AAAGAGCTTCCTCCCGTAGC     (SEQ ID NO: 9)
R: GGATGGCCTTGTCTTCACAC     (SEQ ID NO: 10)

MDA-5 (XM_615590)
F: TGGGACTAACAGCTTCACCA     (SEQ ID NO: 11)
R: ACTGCATCAAGATTGGCACA     (SEQ ID NO: 12)

OAS-1 (CK960499.1)
F: AAGGGTGGCTCCTCAGGCAA     (SEQ ID NO: 13)
R: GTCAACTGACCCAGGGCATC     (SEQ ID NO: 14)

RIG-I (DQ471980)
F: ACGTGGCAGAACAAATCAGA     (SEQ ID NO: 15)
R: TCTGGTTGAACCCTGACTGA     (SEQ ID NO: 16)

ZAP-70 (CB451376)
F: CTGCAAAGATTGACAGCAG      (SEQ ID NO: 17)
R: AGTGGCTGCACAAAATGACA     (SEQ ID NO: 18)

TCR β (BC149560)
F: GAGGAGCAGAACAGGACCAA     (SEQ ID NO: 19)
R: GACAGGACCCCTTGCTGATA     (SEQ ID NO: 20)

TCR γ (BC142018.1)
F: TAGACGGTGCCCTAAAATGG     (SEQ ID NO: 21)
R: AACTGTTTGCCCAGTGGTTT     (SEQ ID NO: 22)

CD3 ζ (NM_174012.2)
F: ACATAGCGGTGTCATTGCAG     (SEQ ID NO: 23)
R: CTCATTCCATGAGGTGAGCA     (SEQ ID NO: 24)

MEK1/2 (CK772376)
F: GCATGCTTTGCTGCTATAAAAA   (SEQ ID NO: 25)
R: AAGGGCTCTGGCTAGATTTTG    (SEQ ID NO: 26)

CD8 (NM_174015.1)
F: TGAGCAACCTGACCTCTGAA     (SEQ ID NO: 27)
R: GGTGGCCTCTCCTCTTTCAT     (SEQ ID NO: 28)
```

Primers were designed using Primer3 software to generate 90-110 bp amplicons and optimized for melting point as well as lack of self-annealing or folding at high temperatures. All amplicons were sequenced to confirm identity to the target genes.

Statistical Analysis

Comparison of the gene expression in TI and PI groups of heifers versus control group and comparison of the gene expression for each group of heifers between multiple time points (days 75-190 of gestation) was performed by applying the unstructured covariance matrix design for longitudinal raw data for relative expression for all time points. Differences of $P<0.05$ were considered statistically significant.

Results

Up-Regulation of Chemokine Ligand 4, and Down-Regulation of Chemokine Receptor 4

Microarray analysis of blood immune cell RNA of pregnant heifers on day 160 of gestation and J5 statistical analysis, applied to the Affymetrix microarray screen of blood cell mRNA from pregnant heifers of PI (n=5) and uninfected control (n=4) groups, revealed differential expression of ~1000 genes from numerous pathways. Several members of type I IFN pathway and members of chemokine family and chemokine receptors were differentially expressed in blood of PI heifers. The two most differentially expressed genes after bovine Affymetrix microarray screening of blood cell mRNA from pregnant heifers with PI compared to control fetuses were: (1) chemokine C—X—C motif ligand 4 (CXCL4, also known as Platelet factor 4)—and it is highly up-regulated in PI mothers, while (2) Chemokine C—X—C motif receptor 4 (CXCR4)—is significantly downregulated in PI mothers. CXCL4 corresponds to Bt.11581.1.S1_at; gb|CK847910; |DB_XREF=970602; RT-PCR primer design nucleotide sequence NM_001101062 and CXCR4 corresponds to Bt.8957.1.S1_at; gb|; RT-PCR primer design nucleotide sequence NM_174301.2, also corresponding to NM_174301).

Figure 5:
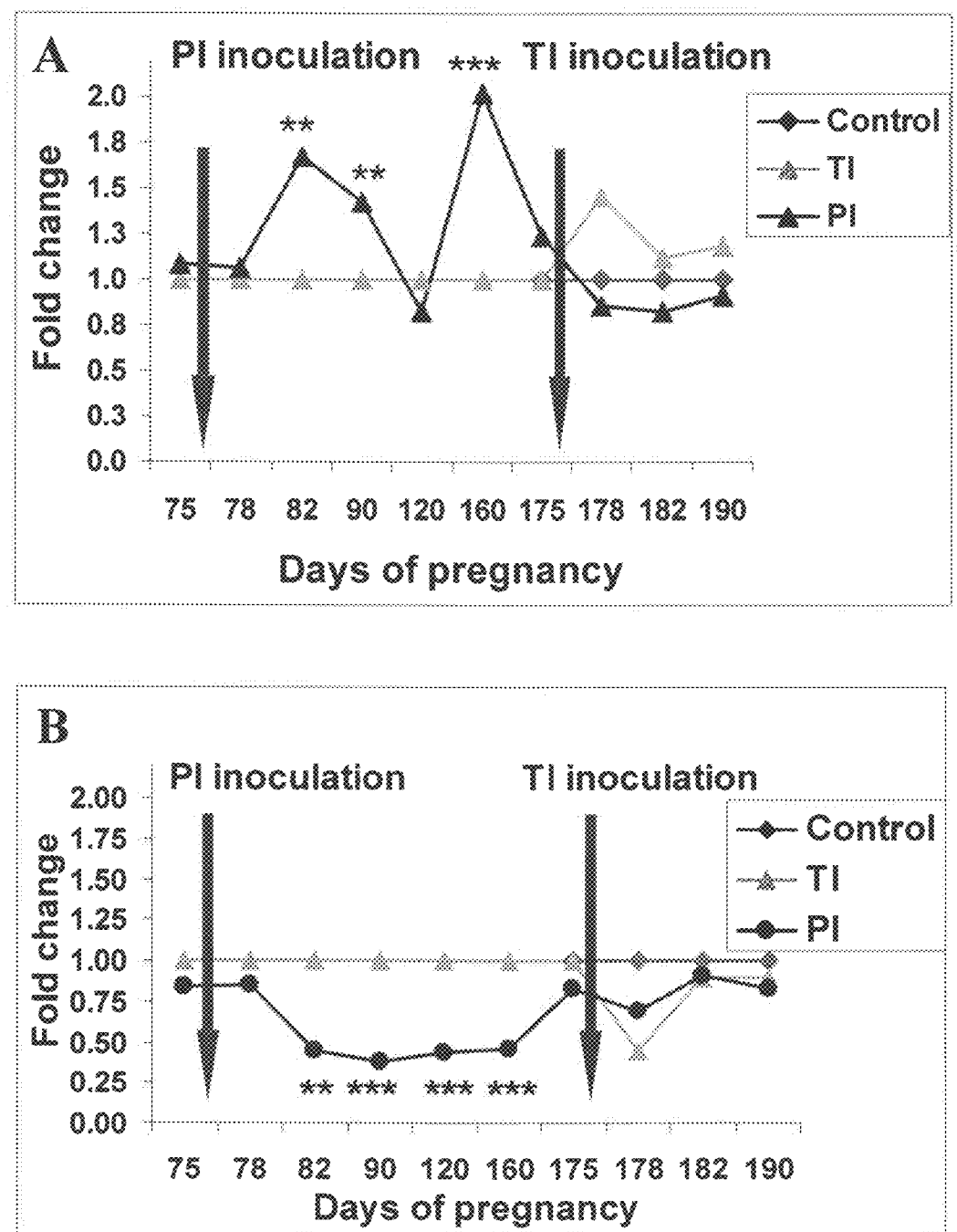
FIG. 5 shows CXCL4 (A) and CXCR4 (B) mRNA expression in blood of pregnant heifers carrying control, TI or PI fetuses (fold change). Expression of CXCL4 and CXCR4 in the control group was considered to be at level 1, and relative expression for infected groups has been normalized against level of uninfected animals. Note the increase in CXCL4 at two times of gestation following PI inoculation in blood cells from mothers carrying PI fetuses. Also note the downregulation of CXCR4 for 90 days of gestation following PI inoculation in blood cells from mothers carrying PI fetuses.

These targets were confirmed to be differentially regulated by using RT-PCR in blood on day 160 of gestation, and through examining blood mRNA profiles for the duration of the in vivo experiment (FIG. 5; example shown for CXCL4 and CXCR4). CXCR4 was the most consistently down-regulated gene in maternal blood immune cells when carrying PI fetuses.

By way of background, the CXCR4 receptor is a G-protein coupled 7-transmembrane receptor that is expressed on immune cells, platelets and the cells of the central nervous system. It has a unique specific endogenous ligand called stromal derived factor 1 (SDF-1; also known as CXCL12). Disruption of SDF-1/CXCR4 interaction impacts multiple biological processes, such as hematopoiesis, cardiogenesis, vasculogenesis, neuronal development and immune cell trafficking. It can also lead to embryonic lethality due to the serious developmental defects and defects in B cell lymphopoeisis, bone marrow colonization and cardiac septum formation. CXCR4 expression is suppressed in response to several viral infections, including late stage HIV and human herpervirus 6 infection (reviewed by (9)).

Significant down-regulation of CXCR4 mRNA expression was detected in blood of heifers 7 days after BVDV inoculation of PI group. CXCR4 expression remained suppressed for 90 days and then returned to baseline expression level by d. 175 of gestation. The trend for transient CXCR4 down-regulation 3 days post inoculation in TI heifers was not statistically significant.

Based on the data in FIG. 5, mothers that are carrying PI fetuses are readily identified based on immune blood cell gene expression. RT-PCR revealed that down-regulation of CXCR4 (fold change ~0.5) occurs by the time of viremia in infected heifers (day 7 PI), and expression remains down-regulated for about 3 months after inoculation (FIG. 5). Notably, CXCR7, also known as RDC1, can also serve as a SDF-1 receptor. Thus, without being bound by theory, CXCR7 (GenBank Accession NM_001098381) may optionally be another gene of interest to detect BVDV in PI animals.

Figure 6:
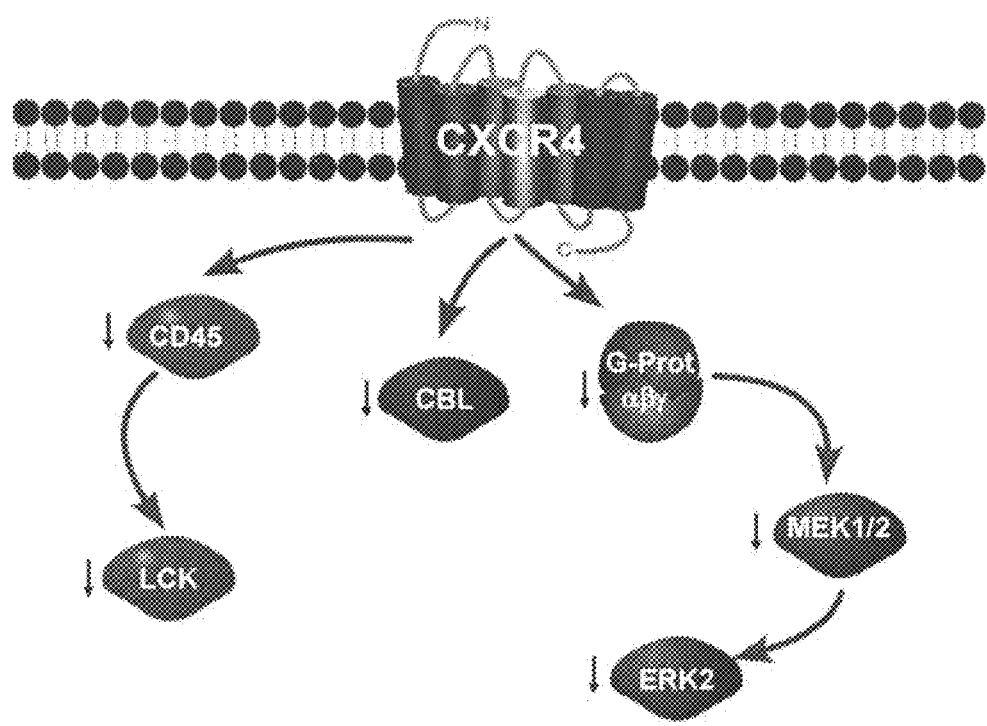
FIG. 6 shows that down-regulation of CXCR4 and associated signal transduction in maternal immune cells with PI fetuses. Green arrows represent activation when CXCR4 is activated. Black arrows represent downregulated targets on the microarray.

Several signal transduction and transcription factors that are downstream from CXCR4 activation also were down-regulated. As shown in FIGS. 6 and 7A, these proteins include: Guanine nucleotide binding protein (G-protein; NM_00109756.1, NM_001024523.1, NM_174811.3); Leukocyte common antigen precursor, tyrosine phosphatase (CD45; BC148881) (required for T-cell activation through the antigen receptor); Proto-oncogene tyrosine-protein kinase LCK (NM_001034334.1; essential for the selection and maturation of developing T-cell in the thymus and in mature T-cell function, which plays a key role in TCR-linked signaling pathways); Tyrosine-protein kinase ZAP70 (CB451376; initiator of cell signaling, which associates with T-cell CD3Z chain, which is associated with TCRγ; BC142018.1), T-cell antigen receptor CD3-Zeta chain (NM_174012.2), E3 ubiquitin-protein ligase CBL (AV594776; negative regulator of signaling pathways); dual-specificity protein kinases MEK1/2 (CK772376; plays a critical role in mitogen growth factor signal transduction), and mitogen-activated protein kinase 1 ERK2 (NM_175793.2; required for initiation of translation) are downregulated in maternal blood with PI fetuses.

The components of the CXCL4/CXCR4 signaling pathway were downregulated in heifers carrying PI fetuses when compared to control uninfected pregnant heifers (FIG. 7A). Direction and ratio of the changes in gene expression on microarray screen (FIG. 7, A) are shown for the genes, used for the confirmation with qRT-PCR (FIG. 7, B). qRT-PCR confirmed significant down regulation of expression of ZAP-70 and MEK1/2 in blood of heifers of the PI group compared to the control group. Expression of CBL and CD45 mRNA was not different in experimental groups in qRT-PCR. Processes affected by changes in CXCR4 signaling are summarized in Table 10.

TABLE 10

Processes affected by changed in CXCR4 signaling in blood of heifers carrying PI fetuses, day 160.

| Processes, affected by changes in CXCR4 signaling | % | p-value |
|---|---|---|
| Ras protein signal transduction | 15.38 | 1.62E−07 |
| Integrin-mediated signaling pathway | 12.82 | 6.98E−07 |
| Cell motility | 17.95 | 7.76E−06 |
| Signal complex formation | 7.69 | 1.40E−05 |
| T-cell proliferation | 7.69 | 2.43E−05 |
| Protein amino acid phosphorylation | 23.08 | 2.87E−05 |
| Intracellular signaling cascade | 15.38 | 2.88E−05 |
| T cell differentiation | 7.69 | 5.77E−05 |
| Nerve growth factor receptor signaling pathway | 5.13 | 8.20E−05 |
| Protein kinase cascade | 12.82 | 1.04E−04 |

Protein amino acid phosphorylation, intracellular signaling cascade, Ras protein signaling transduction, integrin-mediated signaling pathway, protein kinase cascade, and T cell proliferation and differentiation show the highest changes in gene expression.

TCR and CD3 zeta chain, the main members of the TCR pathway, were also down-regulated on the microarray (FIG. 7, A). qRT-PCR confirmed down-regulation of CD34 chain expression (FIG. 7B) and revealed a tendency to down-regulation of TCRγ cluster expression (P=0.058). Expression of surface marker of cytotoxic T cells CD8 was significantly lower in heifers of the PI group both on microarray (ratio 0.79) and in qRT-PCR (FIG. 7, B). Processes affected by the TCR signaling changes in heifers of the PI group are presented in Table 11.

TABLE 11

Processes affected by changes in CXCR4 and TCR signaling in blood of heifers carrying PI fetuses, day 160.

| Processes, affected by changes in TCR signaling | % | p-value |
|---|---|---|
| Positive regulation of T cell activation | 13.79 | 4.53E−30 |
| TCR signaling pathway | 14.66 | 7.95E−27 |
| Regulation of TCR signaling pathway | 7.76 | 3.58E−19 |
| Activation of NF-kappaB transcription factor | 13.79 | 7.37E−19 |
| T cell differentiation | 10.34 | 2.25E−16 |
| Intracellular signaling cascade | 24.14 | 3.16E−14 |
| Positive regulation of calcium-mediated signaling | 7.76 | 1.63E−13 |
| Ras protein signal transduction | 10.34 | 1.02E−12 |
| I-kappaB kinase/NF-kappaB cascade | 7.76 | 1.55E−10 |
| Response to molecule of bacterial origin | 5.17 | 2.43E−10 |
| Regulation of cell cycle | 12.93 | 2.43E−10 |
| Positive regulation of T cell proliferation | 6.90 | 1.15E−08 |
| Cell surface receptor linked signal transduction | 12.93 | 4.03E−08 |
| Cellular defense response | 7.76 | 8.21E−08 |
| Immune response | 15.52 | 1.55E−05 |
| Protein modification process | 7.76 | 1.69E−05 |
| MAPK kinase cascade | 5.17 | 5.20E−05 |
| Caspase activation | 5.17 | 8.77E−05 |

Intracellular signaling cascade, T cell differentiation and activation, regulation of TCR signaling pathway, IκB kinase/NF-κB cascade, MAPK kinase cascade, and immune response, specifically cellular defense response and response to molecule of bacterial origin, were affected the most.

Furthermore, a number of additional candidate diagnostic targets have been identified and are provided in Table 12. Table 12 includes reference sequence information which corresponds to the information on the "Entrez cross-database search page" found on the world wide web at (ncbi.nlm.nih-.gov/gquery). The column of the table with "Bt" numbers corresponds to *bos Taurus* (i.e., the bovine gene chip) from Affymetrix. Sequence and gene information is available through Affymetrix in the world wide web at: (affymetrix- .com). For example, the corresponding reference located in Table 12 closest to the Y-axis of the graph can be entered into the Entrez database search box, and sequence information can be obtained that corresponds with the differentially regulated gene for BVDV diagnostic purposes.

As one of ordinary skill in the art will recognize, up- and down-regulation can be detected in any number of manners include: via ma CXCR4 antibody is used in a lateral flow device to produce a visible signal, or CXCR4 as the capture and an immune cell marker as the detector. This is similar to human urine pregnancy test, only specifically detecting CXCR4; (3) radioimmunoassay; (4) RT-PCR; and (5) standard production of monoclonal antibodies and polyclonal antibodies against the identified receptors for use detection assays.

In the case of an exemplary chemokine, CXCL4 ligand, the diagnostic assay would entail detection of a soluble circulating protein in the serum, plasma, via any method for identifying proteins in blood including: (1) ELISA using polyclonal capture antibody against CXCL4 and monoclonal anti-CXCL4 coupled to biotin for detection or use of a third detecting antibody; or (2) radioimmunoassay. Additional differentially expressed serum proteins in mothers carrying PI fetuses by using proteomic and antibody-based approaches have been identified. Microarray results confirm that PI mothers have differential gene expression and hence differential protein expression from all affected cells, not only immune system cells. The differential protein expression in the blood that may or may not be released from the immune cells will be useful in the ultimate optimization of a robust testing protocol.

The antibodies listed below recognize specific markers other than CXCR4 on the surface of blood immune cells. One of these antibodies could be used to capture the cells and then the anti-CXCR4 could be used on these captured cells as the detecting antibody (i.e., couple to gold or blue latex in a lateral flow device). Antibodies against surface immune cell markers that could be used with CXCR4 in a "sandwich" ELISA are: antibodies for CD3 (T-cells), CD4, CD8 (cytotoxic T-cells), CD14 (macrophages), CD45, CD69 (T-cell activation marker), NKp46 (bovine NK cells), CD11c (dendritic cells) and CD11b (macrophages), B-cell IgG, CD41/61 and (platelets) (all antibodies from VMRD, USA). Though the preceding antibodies are commercially available, these and alternate antibodies can be produced.

The observation that the CXCR4 blood cell marker was chronically and significantly downregulated, provides the basis for diagnostic test that would be useful in identifying and eliminating seroconverted pregnant heifers that have PI fetuses.

Example 4

In addition to the CXCR4 maternal marker for fetal PI infection, the inventors have identified a low-grade and chronic type I IFN response in PI fetuses and steers. The chronic nature of the type I IFN response in PI fetuses and steers offers additional detection opportunities for infected animals.

The classical mechanism of PI BVDV is an evasion of the adaptive immune system which reflects the presence of the virus during immune education and consequent incorporation of the viral antigen into the immune repertoire of host antigens (10, 11). The lack of recognition of the virus by the adaptive immune system results in a failure to clear the infection and a persistent viremia. More recently, numerous studies have implicated a potential role for an evasion of the innate immune system in persistent BVDV infection, in particular the antiviral IFN alpha and beta response (12-18). In contrast to the adaptive immune system, which acts on specific pathogenic antigens, the innate immune system is triggered by the recognition of pathogen associated molecular patterns (PAMP) such as viral RNA (19). Activation of the type I IFN pathway in response to viral infection stimulates an autocrine and paracrine signal transduction cascade resulting in an antiviral state in the host cells and the triggering of an adaptive immune response (20). Type I IFN production is activated by pattern recognition receptors such as Toll-like receptors and RNA helicases which signal the presence of PAMPs and initiate downstream signaling leading to the induction of cytokines (21).

Two classes of receptors serve to detect viral RNA and initiate the antiviral response; Toll-like receptors are located on the cellular membranes of immune cells whereas the RNA helicases retinoic acid inducible protein I (RIG-I) and melanoma differentiation protein 5 (MDA5) are located in the cytosol (22, 23). RIG-I and MDA5 are ubiquitously expressed, and their binding to double stranded RNA (dsRNA) results in activation of the receptor and the initiation of a signaling cascade. A third RNA helicase, LGP2, is induced by type I IFN and seems to serve as a negative feedback by binding to both RIG-I and IFN-β promoter stimulator, and inhibiting their action (24). Members of the type I IFN pathway serve a variety of roles that contribute to the immune defense including growth suppressive and apoptotic effects, which promote cell survival during a viral infection. IFN stimulated genes (ISGs) produced in response to the recognition of viral infection include IFN stimulated gene 15 kD (ISG15), double-stranded RNA (dsRNA) dependent protein kinase (PKR), oligoadenylate synthetase (OAS-1), and myxovirus resistance factor 2 (MX2). ISG15 has been a molecule of particular interest due to its intense pregulation in maternal blood during BVDV infection (25). ISG15 is a ubiquitin-like protein with the ability to conjugate to a variety of intracellular proteins and thus influence their activity through posttranslational modification and enhancing the antiviral response, including regulation of interferon regulator factor (IRF)-3 and PKR (26, 27).

Many viruses have evolved ways to either evade or interfere with specific members of the type I IFN cascade, and several in vitro studies have indicated that BVDV may have the ability to interrupt the type I IFN response by either actively interfering with or failing to induce the IFN regulatory factors 3 and 7 (12, 13, 28). Evidence also exists that BVDV may be able to inhibit the effects of PKR by preventing the molecule's activation by dsRNA (15). A viral interference with the type I IFN pathway, in conjunction with the adaptive immunotolerance of PI, would allow the virus to persist unchallenged by the host immune response. However, in contrast to in vitro studies which have shown a lack of type I IFN activity in ncpBVDV infection, the in vivo production of type I IFN in response to ncpBVDV infection has been demonstrated (25, 29, 30). This response has been identified in acutely infected animals, but has not yet been elucidated in PI animals. In fact, several groups have implicated viral interference with type I IFN signaling as a contributing factor to the ability of the virus to establish PI (17, 31). Without being bound by theory, it is probable that PI animals would exhibit differential gene expression and a type I IFN response as a reflection of the persisting infection. To test this hypothesis, gene expression was studied in the blood of PI steers in comparison to uninfected controls by microarray and RT-PCR. In addition, to compare the amplitude of the type I IFN response in PI animals versus acutely infected animals, members of the type I IFN pathway in TI, PI, and uninfected control fetuses were examined. By studying both adult animals and immature fetuses, it is possible to make inferences concerning the long-term adverse effects of BVDV PI on gene expression. The data provides evidence that BVDV PI induces a low but stable type I IFN response in the blood of both PI steers and fetuses. A long term stimulation of the type I IFN pathway may contribute to the numerous negative consequences of PI including growth and immuno-suppression.

Results

Type I IFN Pathway Genes are Up-Regulated in Blood of PI Steers and in TI and PI Fetuses.

Total blood cell RNA was collected from naturally infected PI steers (n=2; confirmed to be PI with BVDV2 by virus isolation) and age-matched control uninfected steers (n=3). Microarray analysis of blood cell mRNA revealed 294 genes that were differentially regulated in PI vs. control steers ($P<0.05$, >1.5 fold). Type I IFN pathway genes such as ISG15, MX2, OAS1 and PKR, cytosolic dsRNA sensor genes such as RIG-I and MDA5, recently implicated in type I IFN gene regulation upon cytoplasmic dsRNA stimulation (22, 23), and negative regulator of RIG-I function RNA helicase LGP2, were significantly up-regulated in blood from PI steers.

Figure 8:
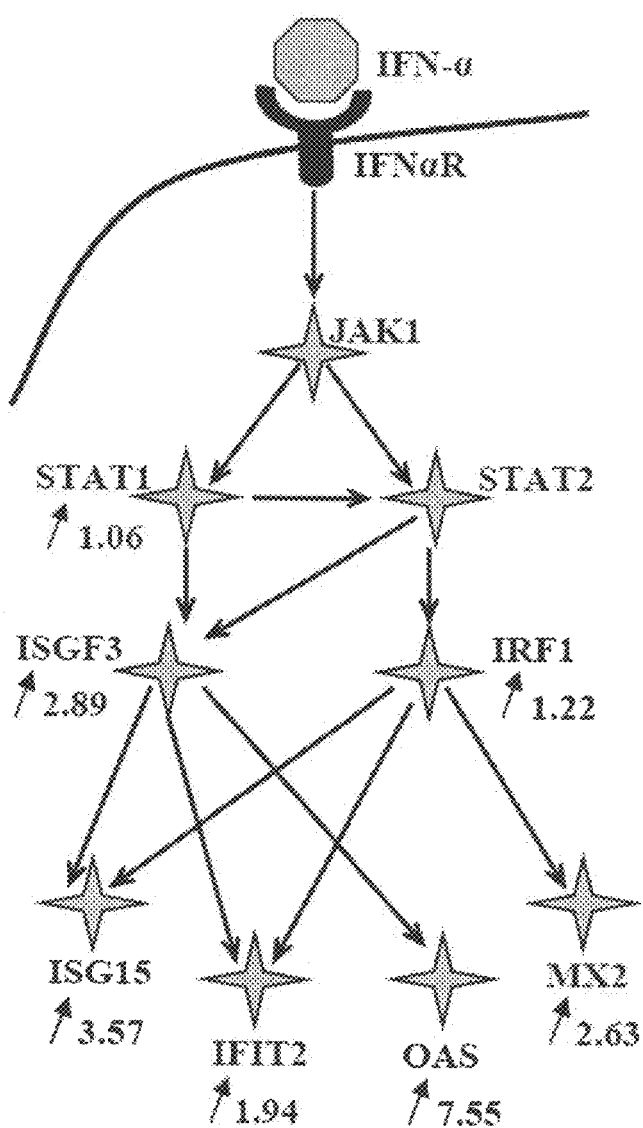
FIG. 8 shows the Type I IFN pathway genes affected by acute ncpBVDV infection and by the presence of a TI fetus in pregnant heifers of the TI group, as detected with the microarray screen on day 190 of gestation. Arrows show direction of the change in gene expression, number shows the ratio of mRNA abundance in blood of heifers of the TI group when compared with the blood of heifers of the control group (microarray data, day 190, P<0.01).
Figure 9:
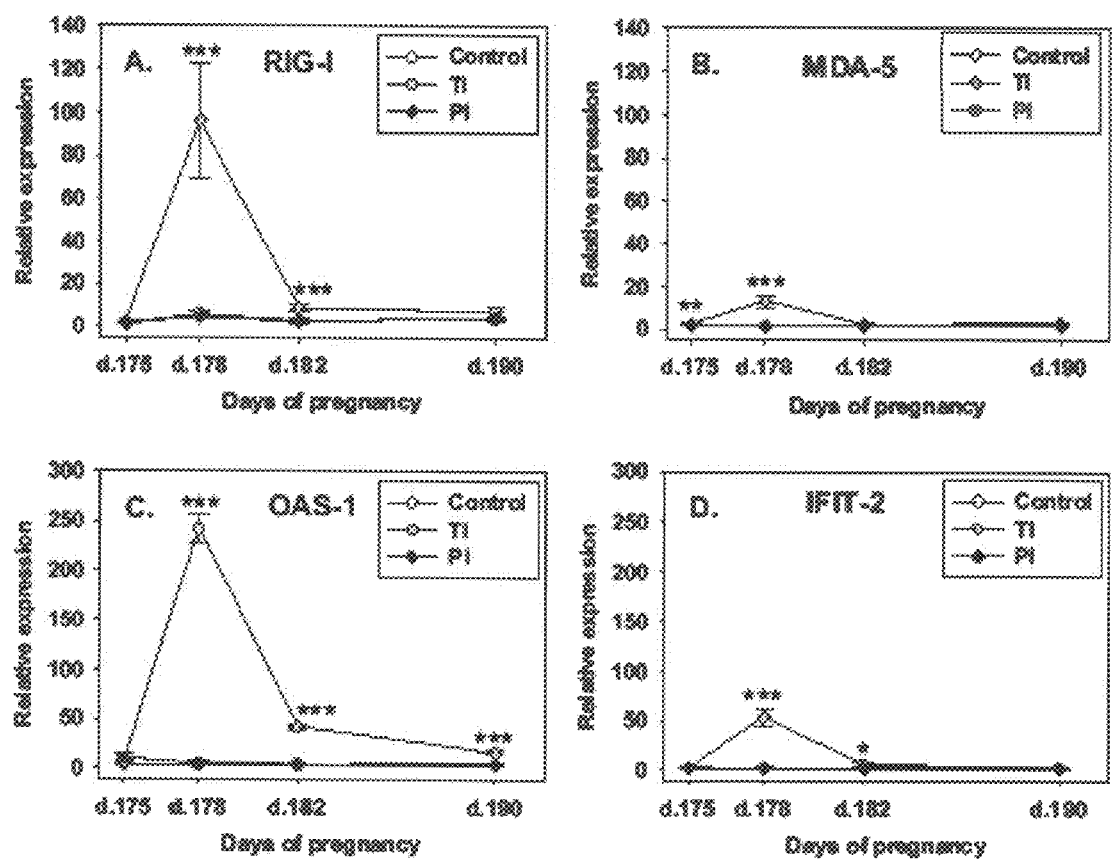
FIG. 9 shows the relative expression of mRNA for cytosolic dsRNA sensors—RIG-I (A) and MDA-5 (B), and for ISGs—OAS-1 (C) and IFIT2 (D) in blood of heifers carrying control, TI, or PI fetuses, detected with qRT-PCR. Data are presented as mean±SE. *—P<0.05, —P<0.1, *—P<0.001. Please note the scale differences between top panel (A, B) and bottom panel (C, D) graphs.

Regarding transient BVDV infection, analysis of the microarray data set for day 190 of gestation revealed strong and evident up-regulation of the type I IFN pathway in blood of heifers of the TI group. Expression of 14 cytosolic sensors for dsRNA—RIG-I and MDA-5—was significantly (2.19 and 1.46 times, respectively) higher in TI heifers compared to control heifers. Multiple genes, including the STAT1/STAT2, IRF1 and ISGF3, as well as several ISGs, have been up-regulated in blood of heifers of the TI group when compared to both control and PI group 15 days post TI challenge. FIG. 8 shows some of the significantly up-regulated genes within the type I IFN pathway. Both cytosolic sensors—RIG-I and MDA-5, and three ISGs—OAS-1, IFN induced protein with tetratricopeptide repeats (IFIT2) from the ISG56 gene family, and ISG15—were selected for the confirmation of the differential expression with the qRT-PCR approach. FIG. 9 shows the relative expression of RIG-I, MDA-5, OAS-1 and IFIT2 in blood of heifers of the PI, TI and control groups of heifers. RIG-I expression (FIG. 9, A) in blood of heifers of the PI and TI groups on day 175 (prior to BVDV challenge) did not differ from the control heifers, while baseline MDA-5 (FIG. 9, B) expression was slightly (1.3 times) higher in blood of TI heifers compared to both control and PI groups. Three days post BVDV challenge of the TI heifers (day 178 of gestation) both RIG-I and MDA-5 demonstrated up-regulation, although with different amplitude. MDA-5 was not up-regulated as much as RIG-I, and returned to the baseline level by day 7 p.i. (day 182 of gestation). Up-regulation of RIG-I was more pronounced and lasted longer, with the return to the baseline by 15 days p.i. (day 190 of gestation). qRT-PCR also confirmed rapid and very significant up-regulation of OAS-1 and IFIT-2 by three and seven days p.i. (d. 178 and 182 of gestation, respectively; FIG. 9, C-D). IFIT-2 expression returned to baseline level by day 15 p.i., while OAS-1 expression remained greater in comparison to the control, but was evidently returning to the baseline. The complete profile of ISG15 relative expression during the course of the infection (days 75-190) has been published previously (25). Briefly, a rapid and dramatic up regulation of ISG15 was observed during acute 15 BVDV infection (days 3-7 p.i.) followed by a return to baseline levels 15 days after both PI and TI challenge of heifers.

Figure 10:
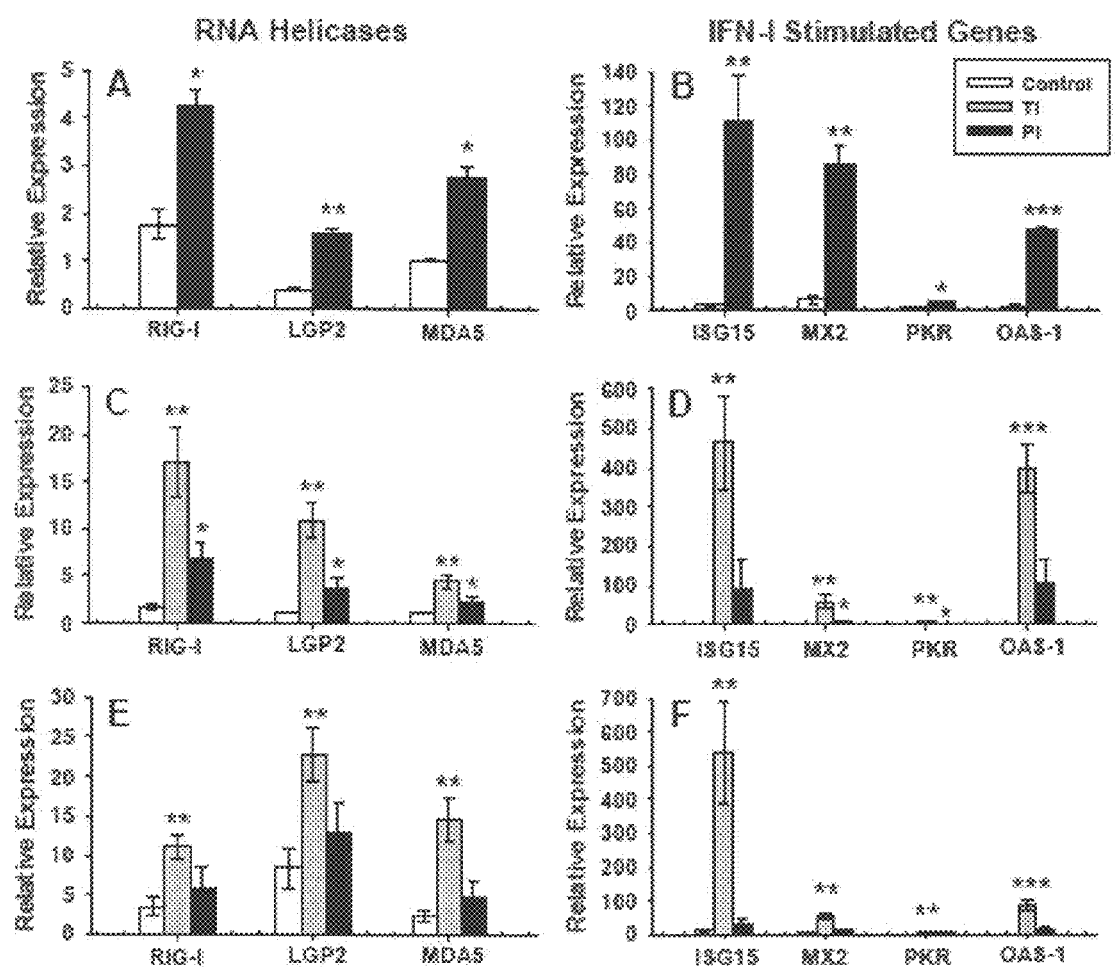
FIG. 10 shows RT-PCR amplification of mRNA for IFN pathway genes. Relative expression of type I IFN pathway genes (RT-PCR) in blood of steers (A, B) and in fetal blood (C, D) and spleen (E, F). The upregulation of RNA helicases would induce production of type I IFN and consequent stimulation of ISGs. This is consistent with finding increased antiviral activity in bloods from TI fetuses and with the interpretation that infection with ncp BVDV induces robust type I IFN antiviral response in acutely infected animals, including developing fetuses. The finding that the type I IFN response is up-regulated in PI fetuses and steers has not been previously reported.

Along the same lines of experimentation, RT-PCR was used to confirm differential expression of targets that were identified from the microarray analysis of PI vs control steer blood. A summary of the RT-PCR amplification of mRNA for RIG-I, MDA5, ISG15, MX2, PKR, OAS1, and LGP2 from fetal blood and spleen on day 190 of gestation, as well as from PI steer blood, is presented in FIG. 10. Expression of cytosolic dsRNA sensors, RIG-I and MDA-5, that activate production of type I IFN was highly up-regulated in blood of TI fetuses ($P<0.01$) 15 days p.i., and, to a lesser degree, in blood of PI fetuses 115 days p.i., as well as in blood of PI steers ($P<0.05$). LGP2 was also significantly upregulated in TI fetuses, and PI fetuses and steers (blood). All four ISGs tested (ISG15, MX2, PKR and OAS1) were highly up-regulated in PI steer blood and in blood of TI fetuses. Expression of MX2 and PKR was significantly up-regulated in blood of PI fetuses; however, while ISG15 and OAS1 expression showed the same trend, the difference between PI and control fetal blood was not significant due to high variation between animals. Analysis of the gene expression in fetal spleen with RT-PCR demonstrated high up-regulation of all tested genes mRNA in TI fetuses. A similar trend was not apparent in PI spleen tissue, when compared to control fetuses.

Figure 11:
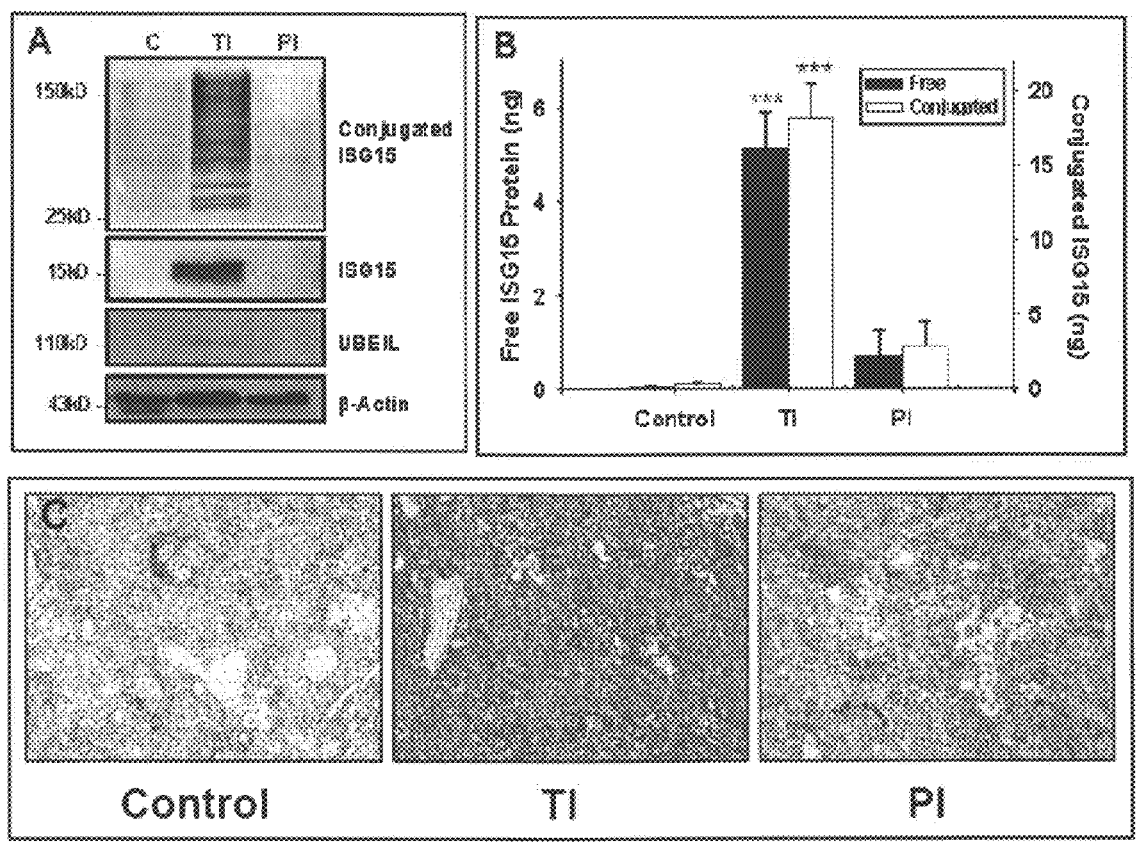
FIG. 11 shows ISG15 and conjugation to targeted proteins is up-regulated in spleens from TI when compared to PI and control fetuses. A. Western blot analysis of ISG15 and UBE1L protein in fetal spleen. B. Quantitative analysis of free and conjugated ISG15 and UBE1L in spleen of infected fetuses. Black columns—free ISG15, white columns—conjugated ISG15. Recombinant bovine ISG15 (rboISG15) served as a positive control. Image Quant 5.2 software was used to quantify the intensity of protein bands. C. Immunohistochemical localization of ISG15 in fetal spleen. Control fetal spleen reflects a very basal expression of ISG15 in reticular cells. Massive upregulation of ISG15 was observed in fetal spleen following TI. Also a very localized and significant upregulation of ISG15 in PI fetal spleen endothelial and macrophage-like cells was evident.

Western blot analysis of proteins from fetal spleen revealed high amount of both conjugated and free ISG15 protein in TI fetuses (FIG. 11), while low ISG15 was detected in PI or control fetuses. Western blot for ubiquitin-like activating enzyme, E1 like (UBE1L), known to act as ISG15 conjugating enzyme, revealed UBE1L expression in the spleen of TI fetuses (FIG. 11), while no significant amount of UBE1L was detected in control or PI fetuses. Quantitative analysis of the western blot performed with StormImager (Amersham, GE Healthsciences) confirmed significant and very high up-regulation of ISG15 protein, both free and conjugated, in spleen of TI fetuses (FIG. 11).

Immunohistochemical localization of ISG15 in control spleens was discretely limited to reticular and macrophage-like cells. A much more diffuse pattern of ISG15 antigen was detected in the PI and TI spleens, with strong signals localized to endothelial cells of the sinusoids and blood vessels, reticular cells, and macrophage-like cells. Notably, the intensity of ISG15 staining in the TI spleen was much stronger than in the PI.

PI fetuses, whose dams were infected with ncp BVDV at day 75 of gestation, are able to mount type I IFN response to the infecting virus, but because of insufficient development of immune system and consequent lack of BVDV antigen recognition they are not able to clear the virus. Persistence of the virus causes prolonged stimulation of type I IFN pathway genes. For example, up-regulation of ISGs occurred to varying degrees even 115 days p.i. (in PI fetuses) and after birth (PI steers). Activation of LGP2 would provide the negative feedback to inhibit the type I IFN pathway. This, coupled with the induction of ISGs, might provide the mechanism that controls the type I IFN response to viral infection. In adult animals and, probably, immunocompetent fetuses the type I IFN response is transient, and returns to basal level after the clearance of the virus. However, in PI fetuses with developing adaptive immunity the persisting virus is not recognized as a foreign, which leads to lifelong PI, and, as shown, to chronic up-regulation of type I IFN. Because type I IFN can act as a growth-suppressive cytokine (32), a long-term up-regulation of ISGs may contribute to the IUGR, seen in animals with persistent BVDV infection.

REFERENCES

1. Andrejeva J, Childs K S, Young D F, Carlos T S, Stock N, Goodbourn S, and Randall R E. The V proteins of paramyxoviruses bind the IFN-inducible RNA helicase, mda-5, and inhibit its activation of the IFN-beta promoter. *Proceedings of the National Academy of Sciences of the United States of America* 101: 17264-17269, 2004.
2. Baigent S J, Goodbourn S, and McCauley J W. Differential activation of interferon regulatory factors-3 and -7 by noncytopathogenic and cytopathogenic bovine viral diarrhea virus. *Veterinary immunology and immunopathology* 100: 135-144, 2004.
3. Baigent S J, Zhang G, Fray M D, Flick-Smith H, Goodbourn S, and McCauley J W. Inhibition of beta interferon transcription by noncytopathogenic bovine viral diarrhea virus is through an interferon regulatory factor 3-dependent mechanism. *Journal of virology* 76: 8979-8988, 2002.
4. Balabanian K, Lagane B, Infantino S, Chow K Y, Harriague J, Moepps B, Arenzana-Seisdedos F, Thelen M, and Bachelerie F. The chemokine SDF-1/CXCL12 binds to and signals through the orphan receptor RDC1 in T lymphocytes. *The Journal of biological chemistry* 280: 35760-35766, 2005.
5. Bielefeldt-Ohmann H. The pathologies of bovine viral diarrhea virus infection. A window on the pathogenesis. *The Veterinary clinics of North America* 11: 447-476, 1995.
6. Bolstad B M, Irizarry R A, Astrand M, and Speed T P. A comparison of normalization methods for high density oligonucleotide array data based on variance and bias. *Bioinformatics* 19: 185-193, 2003.
7. Brackenbury L S, Carr B V, and Charleston B. Aspects of the innate and adaptive immune responses to acute infections with BVDV. *Veterinary microbiology* 96: 337-344, 2003.
8. Brown G B, Bolin S R, Frank D E, and Roth J A. Defective function of leukocytes from cattle persistently infected with bovine viral diarrhea virus, and the influence of recombinant cytokines. *American journal of veterinary research* 52: 381-387, 1991.
9. von Hundelshausen P, Weber C. Platelets as immune cells: bridging inflammation and cardiovascular disease. Circ Res 2007; 100: 27-40.
10. Peterhans E, Jungi T W, Schweizer M. BVDV and innate immunity. Biologicals 2003; 31: 107-112.
11. Potgieter L N. Immunology of bovine viral diarrhea virus. Vet. Clin. North Am. Food Anim. Pract. 1995; 11: 501-520.
12. Baigent S J, Zhang G, Fray M D, Flick-Smith H, Goodbourn S, McCauley J W. Inhibition of beta interferon transcription by noncytopathogenic bovine viral diarrhea virus is through an interferon regulatory factor 3-dependent mechanism. J Virol 2002; 76: 8979-8988.
13. Chen Z, Rijnbrand R, Jangra R K, Devaraj S G, Qu L, Ma Y, Lemon S M, Li K. Ubiquitination and proteasomal degradation of interferon regulatory factor-3 induced by Npro from a cytopathic bovine viral diarrhea virus. Virology 2007; 366: 277-292.
14. Gil L H, Ansari I H, Vassilev V, Liang D, Lai V C, Zhong W, Hong Z, Dubovi E J, Donis R O. The amino-terminal domain of bovine viral diarrhea virus Npro protein is necessary for alpha/beta interferon antagonism. J Virol 2006; 80: 900-911.
15. Gil L H, van Olphen A L, Mittal S K, Donis R O. Modulation of PKR activity in cells infected by bovine viral diarrhea virus. Virus Res 2006; 116: 69-77.
16. Iqbal M, Poole E, Goodbourn S, McCauley J W. Role for bovine viral diarrhea virus Erns glycoprotein in the control of activation of beta interferon by double-stranded RNA. J Virol 2004; 78: 136-145.
17. Schweizer M, Matzener P, Pfaffen G, Stalder H, Peterhans E. "Self" and "nonself" manipulation of interferon defense during persistent infection: bovine viral diarrhea virus resists alpha/beta interferon without blocking antiviral activity against unrelated viruses replicating in its host cells. J Virol 2006; 80: 6926-6935.
18. Schweizer M, Peterhans E. Noncytopathic bovine viral diarrhea virus inhibits double-stranded RNA-induced apoptosis and interferon synthesis. J Virol 2001; 75: 4692-4698.
19. Saito T, Gale M, Jr. Principles of intracellular viral recognition. Curr Opin Immunol 2007; 19: 17-23.
20. Samuel C E. Antiviral actions of interferons. Clin Microbiol Rev 2001; 14: 778-809, table of contents.
21. Alexopoulou L, Holt A C, Medzhitov R, Flavell R A. Recognition of double-stranded RNA and activation of NF-kappaB by Toll-like receptor 3. Nature 2001; 413: 732-738.
22. Kang D C, Gopalkrishnan R V, Wu Q, Jankowsky E, Pyle A M, Fisher P B. mda-5: An interferoninducible putative RNA helicase with double-stranded RNA-dependent ATPase activity and melanoma growth-suppressive properties. Proc Natl Acad Sci USA 2002; 99: 637-642.
23. Yoneyama M, Kikuchi M, Natsukawa T, Shinobu N, Imaizumi T, Miyagishi M, Taira K, Akira S, Fujita T. The RNA helicase RIG-I has an essential function in double-stranded RNA-induced innate antiviral responses. Nat Immunol 2004; 5: 730-737.
24. Komuro A, Horvath C M. RNA- and virus-independent inhibition of antiviral signaling by RNA helicase LGP2. J Virol 2006; 80: 12332-12342.
25. Smirnova N P, Bielefeldt-Ohmann H, Van Campen H, Austin K J, Han H, Montgomery D L, Shoemaker M L, van Olphen A L, Hansen T R. Acute non-cytopathic bovine viral diarrhea virus infection induces pronounced type I interferon response in pregnant cows and fetuses. *Virus research* 132: 49-58, 2008.
26. Zhao C, Denison C, Huibregtse J M, Gygi S, Krug R M. Human ISG15 conjugation targets both IFN-induced and constitutively expressed proteins functioning in diverse cellular pathways. Proc Natl Acad Sci USA 2005; 102: 10200-10205.
27. Lu G, Reinert J T, Pitha-Rowe I, Okumura A, Kellum M, Knobeloch K P, Hassel B, Pitha P M. ISG15 enhances the innate antiviral response by inhibition of IRF-3 degradation. Cell Mol Biol (Noisy-le-grand) 2006; 52: 29-41.
28. Hilton L, Moganeradj K, Zhang G, Chen Y H, Randall R E, McCauley J W, Goodbourn S. The NPro product of bovine viral diarrhea virus inhibits DNA binding by interferon regulatory factor 3 and targets it for proteasomal degradation. J Virol 2006; 80: 11723-11732.
29. Brackenbury L S, Carr B V, Stamataki Z, Prentice H, Lefevre E A, Howard C J, Charleston B. Identification of a cell population that produces alpha/beta interferon in vitro and in vivo in response to noncytopathic bovine viral diarrhea virus. J Virol 2005; 79: 7738-7744.
30. Charleston B, Brackenbury L S, Carr B V, Fray M D, Hope J C, Howard C J, Morrison W I. Alpha/beta and gamma interferons are induced by infection with noncytopathic bovine viral diarrhea virus in vivo. J Virol 2002; 76: 923-927.
31. Charleston B, Fray M D, Baigent S, Carr B V, Morrison W I. Establishment of persistent infection with non-cytopathic bovine viral diarrhoea virus in cattle is associated with a failure to induce type I interferon. J Gen Virol 2001; 82: 1893-1897.
32. Iwase S, Furukawa Y, Kikuchi J, Nagai M, Terui Y, Nakamura M, Yamada H. Modulation of E2F activity is linked to interferon-induced growth suppression of hematopoietic cells. J Biol Chem 1997; 272: 12406-12414.
33. Cole T J, Henson G L, Tremble J M, Colley N V. Birthweight for length: ponderal index, body mass index or Benn index. Ann Hum Biol 1997; 24: 289-298.

34. Nuss K, Spiess A, Hilbe M, Sterr K, Reiser M, Matis U. Transient benign osteopetrosis in a calf persistently infected with bovine virus diarrhoea virus. Vet Comp Orthop Traumatol 2005; 18: 100-104.

35. Bielefeldt-Ohmann H, Tolnay A-E, Reisenhauer C E, Hansen T R, Smirnova N, Van Campen H. Transplacental Infection with Non-Cytopathic Bovine Viral Diarrhoea Virus Type 1 and 2: Viral Spread and Molecular Neuropathology. J Comp Pathol 2007; In Press.

36. Ohmann H B. Experimental fetal infection with bovine viral diarrhea virus. II. Morphological reactions and distribution of viral antigen. Can J Comp Med 1982; 46: 363-369.

While certain of the preferred embodiments of the present invention have been described and specifically exemplified above, it is not intended that the invention be limited to such embodiments. Various modifications may be made thereto without departing from the scope of the present invention, as set forth in the following claims.

What is claimed is:

1. A method for diagnosing BVDV in a persistently infected ruminant test animal comprising:
   a) obtaining a biological sample from a test animal and from a control animal seronegative for BVDV;
   b) contacting said sample with an agent having affinity for a differentially expressed CXCR4 marker comprising SEQ ID NO: 58; and
   c) diagnosing the presence of BVDV via detection of said differentially expressed BVDV marker, wherein an alteration in the expression level of said BVDV marker obtained from said test animal relative to that obtained from said seronegative control animal indicates said test animal is persistently infected with BVDV, and wherein said alteration is CXCR4 down-regulation.

2. The method of claim 1, wherein said ruminant test animal is pregnant or is a fetus.

3. The method of claim 2, wherein said biological sample from said test animal is obtained between day 82 and day 160 of gestation.

4. The method of claim 1, wherein said at least one BVDV marker is a nucleic acid and said detection is performed using PCR.

5. The method of claim 1, wherein said detection of said marker is via qRT-PCR.

6. The method of claim 1, wherein said at least one BVDV marker is a nucleic acid and affixed to a solid support.

7. The method of claim 1, wherein said biological sample is selected from the group consisting of blood, urine, skin, serum, milk, sputum, saliva, and tears.

8. The method of claim 7 wherein said biological sample comprises blood cells or skin cells which are lysed to release nucleic acids therein.

9. The method of claim 1, wherein said marker is involved in chemokine signaling.

10. The method of claim 9, wherein said marker involved in cytokine signaling is a nucleic acid or polypeptide.

11. The method of claim 10, wherein said BVDV marker is a polypeptide and said expression level is down-regulated in response to persistent BVDV infection.

12. The method of claim 1, wherein said at least one BVDV marker is a polypeptide immobilized on a solid support.

13. The method of claim 1, wherein said test animal is a persistently infected steer.

14. The method of claim 1, wherein said test animal is selected from the group consisting of a bovine, a steer, a pregnant bovine, a bovine fetus and a bovine calf.

15. The method of claim 1, wherein said agent having affinity for said BVDV marker is selected from the group consisting of at least one nucleic acid which specifically hybridizes with a CXCR4 encoding nucleic acid comprising SEQ ID NO: 58, and an antibody immunologically specific for the polypeptide encoded by SEQ ID NO: 58.

16. The method of claim 1, further comprising the step of euthanizing test animals diagnosed with BVDV.

* * * * *